US011963983B2

(12) United States Patent
Chaudhry

(10) Patent No.: US 11,963,983 B2
(45) Date of Patent: Apr. 23, 2024

(54) METHODS OF CARDIAC REPAIR

(71) Applicant: Icahn School of Medicine at Mount Sinai, New York, NY (US)

(72) Inventor: Hina W. Chaudhry, New York, NY (US)

(73) Assignee: Icahn School of Medicine at Mount Sinai, New York, NY (US)

(*) Notice: Subject to any disclaimer, the term of this patent is extended or adjusted under 35 U.S.C. 154(b) by 0 days.

(21) Appl. No.: 16/693,998

(22) Filed: Nov. 25, 2019

(65) Prior Publication Data

US 2020/0101117 A1    Apr. 2, 2020

Related U.S. Application Data

(60) Continuation of application No. 15/662,755, filed on Jul. 28, 2017, now abandoned, which is a division of application No. 13/671,396, filed on Nov. 7, 2012, now abandoned.

(60) Provisional application No. 61/556,700, filed on Nov. 7, 2011.

(51) Int. Cl.
 A61K 35/50    (2015.01)
 A61K 35/12    (2015.01)

(52) U.S. Cl.
 CPC .............. *A61K 35/50* (2013.01); *A61K 35/12* (2013.01)

(58) Field of Classification Search
 None
 See application file for complete search history.

(56) References Cited

U.S. PATENT DOCUMENTS

| | | | |
|---|---|---|---|
| 5,079,160 A | 1/1992 | Lacy et al. | |
| 5,322,790 A | 6/1994 | Scharp et al. | |
| 5,422,261 A | 6/1995 | Lee et al. | |
| 5,424,208 A | 6/1995 | Lee et al. | |
| 6,589,728 B2 | 7/2003 | Csete et al. | |
| 6,911,201 B1 | 6/2005 | Merchav et al. | |
| 7,534,609 B2 | 5/2009 | Merchav et al. | |
| 7,678,573 B2 | 3/2010 | Merchav et al. | |
| 7,893,315 B2 | 2/2011 | Chung et al. | |
| 2004/0247564 A1 | 12/2004 | Itescu | |
| 2005/0180958 A1 | 8/2005 | Merchav et al. | |
| 2006/0160733 A1 | 7/2006 | Chaudhry et al. | |
| 2007/0178075 A1 | 8/2007 | Chaudhry et al. | |
| 2008/0260704 A1 | 10/2008 | Riordan et al. | |
| 2009/0263361 A1* | 10/2009 | Lee ..................... | C12N 5/0605 435/366 |
| 2010/0209403 A1 | 8/2010 | Meiron et al. | |
| 2010/0233130 A1 | 9/2010 | Meretzki | |
| 2011/0129447 A1 | 6/2011 | Meretzki et al. | |
| 2011/0129486 A1 | 6/2011 | Meiron | |
| 2011/0171182 A1 | 7/2011 | Abelman | |
| 2011/0256108 A1 | 10/2011 | Meiron et al. | |
| 2011/0256159 A1 | 10/2011 | Meiron et al. | |
| 2011/0256160 A1 | 10/2011 | Meiron et al. | |
| 2011/0293583 A1 | 12/2011 | Aberman | |
| 2013/0004465 A1 | 1/2013 | Aberman | |
| 2013/0039892 A1 | 2/2013 | Aberman | |
| 2013/0142762 A1 | 6/2013 | Chaudhry | |

FOREIGN PATENT DOCUMENTS

| | | | |
|---|---|---|---|
| WO | 2006052646 A2 | 5/2006 | |
| WO | 2006052925 A2 | 5/2006 | |
| WO | 2008002250 A1 | 1/2008 | |
| WO | 2010031006 A1 | 3/2010 | |
| WO | 2010083466 A1 | 7/2010 | |
| WO | WO-2010083466 A1 * | 7/2010 | ................ A61P 9/00 |
| WO | 2010091051 A2 | 8/2010 | |

OTHER PUBLICATIONS

Hemberger et al. "ELF5-enforced transcriptional networks define and epigenetically regulated trophoblast stem cell compartment in the human placenta", Human Molecular Genetics 19(12): 2456-67, Mar. 2010 (Year: 2010).*
Ottersbach et al. "The Murine placenta contains hematopoietic stem cells within the vascular labyrinth region", Developmental Cell 8: 377-87, 2005 (Year: 2005).*
Kara et al. "Fetal cells traffic to injured maternal myocardium and undergo cardiac differentiation." Circulation research 110.1 (2012): 82-93. (Year: 2012).*
Ozawa et al. "A novel method for purification of inner cell mass and trophectoderm cells from blastocysts using magnetic activated cell sorting", Fertility and Sterility 95(2): 799-802, Feb. 2011, published online Nov. 5, 2010 (Year: 2010).*
Kara et al. "Fetal cells traffic to injured maternal myocardium and undergo cardiac differentiation." Circulation research 110.1: 82-93, 2012 (Year: 2012).
Albelda, et al. Molecular and Cellular Properties ofPECAM-1 (endoCAM/CD31) :A Novel Vascular Cell-Cell Adhesion Molecule. J Cell Biol 114:1059-1068, 1991.
Amado et al., Cardiac repair with intramyocardial injection of allogeneic mesenchymal stem cells after myocardial infarction. Proc Natl Acad Sci USA. 102:11474-11479, 2005.
Assmus, B. et al., "Transplantation of progenitor cells and regeneration enhancement in acute myocardial infarction (TOPCARE-AMI)," Circulation, 106(24):3009-3017, Nov. 2002.

(Continued)

*Primary Examiner* — Emily A Cordas
(74) *Attorney, Agent, or Firm* — Fox Rothschild LLP

(57) ABSTRACT

Provided herein is a new method to isolate and expand cardiac progenitor/stem cells from a placenta, which produces a cell population enriched in multipotent functional progenitor/stem cells. Cardiac progenitor/stem cells isolated by this method maintain their self-renewal character in vitro and differentiate into normal cells in myocardium, including cardiomyocytes, endothelial cells, and smooth muscle cells, after transplantation into ischemic hearts. Also provided in this application are substantially pure populations of multipotent cardiac progenitor/stem cells, and their use to treat and prevent diseases and injuries, including those resulting from myocardial infarction. A model for assessing the potential of cardiac stem cells for treatment of myocardial infarction is also provided.

12 Claims, 21 Drawing Sheets
Specification includes a Sequence Listing.

(56) References Cited

OTHER PUBLICATIONS

Bayes-Genis et al., Identification of male cardiomyocytes of extracardiac origin in the hearts of women with male progeny: male fetal cell microchimerism of the heart. J Heart Lung Transplant 24:2179-2183, 2005.
Beck, F., and Stringer, E.J. (2010). The role of Cdx genes in the gut and in axial development. Biochem Soc Trans 38, 353-357.
Beltrami, et al., Adult cardiac stem cells are multipotent and support myocardial regeneration. Cell 114:763-776, 2003.
Bianchi, et al., Male fetal progenitor cells persist in maternal blood for as long as 27 years postpartum. Proc Natl Acad Sci US A 93:705-708, 1996.
Bolli, P., and Chaudhry, H.W. (2010). Molecular physiology of cardiac regeneration. Ann NY Acad Sci 1211 :113-126.
Boyd et al., Genome-wide analysis of cdx2 binding in intestinal epithelial cells (caco-2). J Biol Chem. 285: 25115-25125, 2010.
Campagnoli, et al., Identification of mesenchymal stem/progenitor cells in human first-trimester fetal blood, liver, and bone marrow. Blood 98, 2396-2402, 2001.
Chawengsaksophak, K., de Graaff, W., Rossant, J., Deschamps, J., and Beck, F. (2004). Cdx2 is essential for axial elongation in mouse development. Proc Natl Acad Sci USA 101, 7641-7645.
Chawengsaksophak, K., James, R., Hammond, V.E., Kontgen, F., and Beck, F. (1997). Homeosis and intestinal tumours in Cdx2 mutant mice. Nature 386, 84-87.
Chen, J., Sanberg, P.R., Li, Y., Wang, L., Lu, M., Willing, A.E., Sanchez-Ramos, J., and Chopp, M. (2001). Intravenous administration of human umbilical cord blood reduces behavioral deficits after stroke in rats. Stroke 32, 2682-2688.
Cheng, et al., Cyclin A2 induces cardiac regeneration after myocardial infarction and prevents heart failure. Circ Res 100, 1741-1748, 2007.
Civin, et al., Sustained, retransplantable, multilineage engraftment of highly purified adult human bone marrow stem cells in vivo. Blood 88:4102-4109, 1996.
Dawe et al., Cell migration from baby to mother. Cell Adhesion & Migration. 1(1):19-27, 2007.
Ekelund et al., Intravenous allopurinol decreases myocardial oxygen consumption and increases mechanical efficiency in dogs with pacing-induced heart failure. Circ Res. 85:437-445, 1999.
EP Application No. 12847330.3 Partial Supplementary European Search Report dated Apr. 9, 2015.
Felker, et al., Underlying causes and long-term survival in patients with initially unexplained cardiomyopathy. N Engl J Med 342:1077-1084, 2000.
Fujiki, et al., Fetal cells in the pregnant mouse are diverse and express a variety of progenitor and differentiated cell markers. Biol Reprod 81 :26-32, 2009.
Fujiki et al., Fetomaternal trafficking in the mouse increases as delivery approaches and is highest in the maternal lung. Biol Reprod. 79(5):841-848, 2008.
Gekas, C., Dictorlcn-Licvrc, F., Orkin, S.H., and Mikkola, H.K. The placenta is a niche for hematopoictic stem cells. Dev Cell 8, 365-375, 2005.
Hare JM, Kass DA, Stamler JS. The physiological response to cardiovascular 'orphan' g proteincoupled receptor agonists. Nat Med. 5: 1241-1242, 1999.
Hassink et al., Stem cell therapy for ischemic heart disease Trends in Molecular Medicine, 9(10):436-441, 2003.
Hayase et al. Heart Cir. Physiol. 288: H2995-H3000, 2005.
He, et al., Human embryonic stem cells develop into multiple types of cardiac myocytes: action potential characterization. Circ Res 93,:32-39, 2003.
Iancheran et al., Human fetal mechanics: A source of stem cells for tissue regeneration and repair? Placenta. 30:2-10, 2009.
James, P.R. A review of peripartum cardiomyopathy. Int J Clin Pract 58, 363-365, 2004.
Joshi M, Keith Pittman H, Haisch C, Verbanac K. Real-time PCR to determine transgene copy number and to quantitate the biolocalization of adoptively transferred cells from EGFPtransgenic mice. BioTechniques. 45(3):247-258, 2008.
Kara et al., Fetal cells traffic to injured maternal myocardium and undergo cardiac differentiation. Circ. Res., 110:82-93. 2012.
Kara RJ, Bolli P, Karakikes I, Matsunaga I, Tripodi J, Tanweer 0, Altman P, Shachter NS, Nakano A, Najfeld V, Chaudhry HW. Fetal cells traffic to injured maternal myocardium and undergo cardiac differentiation. Circ Res. 110:82-93, 2012.
Kawamoto A, Murayama T, Kusano K, Ii M, Tkebuchava T, Shintani S, Iwakura A, Johnson I, von Samson P, Hanley A, Gavin M, Curry C, Silver M, Ma H, Kearney M, Losardo DW. Synergistic effect of bone marrow mobilization and vascular endothelial growth factor-2 gene therapy in myocardial ischemia. Circulation. 110: 1398-1405, 2004.
Kelley et al., "Restraining Infarct Expansion Preserves Left Ventricular Geometry and Function After Acute Anteroapical Infarction," Circulation 99:135-142, 1999.
Kelly RP, Ting CT, Yang TM, Liu CP, Maughan WL, Chang MS, Kass DA. Effective arterial elastance as index of arterial vascular load in humans. Circulation. 86: 513-521, 1992.
Khosrotehrani, K., Johnson, K.L., Cha, D.H., Salomon, R.N., and Bianchi, D.W. Transfer of fetal cells with multilineage potential to maternal tissue. JAMA 292:75-80, 2004.
Khosrotehrani, K., Leduc, M., Bachy, V., Nguyen Huu, S., Oster, M., Abbas, A., Uzan, S., and Aractingi, S. Pregnancy allows the transfer and differentiation of fetal lymphoid progenitors into functional T and B cells in mothers. J Immunol 180, 889-89, 2008.
Kiberstis. Young at heart. Science, 334(6061):1324, 2011.
Kleeberger, W., Versmold, A., Rothamel, T., Glockner, S., Bredt, M., Haverich, A., Lehmann, U., and Kreipe, H. (2003). Increased chimerism of bronchial and alveolar epithelium in human lung allografts undergoing chronic injury. Am J Pathol 162, 1487-1494.
Klonisch, T., and Drouin, R. (2009). Fetal-maternal exchange of multipotent stem/progenitor cells: microchimerism in diagnosis and disease. Trends Mol Med 15, 510-518.
Komuro, I., and Izumo, S. (1993). Csx: a murine homeobox-containing gene specifically expressed in the developing heart. Proc Nati Acad Sci USA 90, 8145-8149.
Laugwitz, K.L., Moretti, A., Lam, J., Gruber, P., Chen, Y., Woodard, S., Lin, L.Z., Cai, C.L., Lu, M.M., Reth, M., et al. (2005b). Postnatal isll+ cardioblasts enter fully differentiated cardiomyocytes lineages. Nature 433, 647-653.
Liegeois, A., Escourrou, J., Ouvre, E., and Charreire, J. (1977). Microchimerism: a stable state of low-ratio proliferation of allogeneic bone marrow. Transplant Proc 9, 273-276.
Lim. Stem cells: Do fetal cells repair maternal hearts? Nature Reviews Cardiology, 9:67, 2012.
Martin, C.M., Meeson, A.P., Robertson, S.M., Hawke, T.J., Richardson, J.A., Bates, S., Goetsch, S.C., Gallardo, T.D., and Garry, D.J. (2004). Persistent expression of the ATP-binding cassette transporter, Abcg2, identifies cardiac SP cells in the developing and adult heart. Dev Biol 265, 262-275.
Mehta, N.J., Mehta, R.N., and Khan, 1.A. (2001). Pcripartum cardiomyopathy: clinical and therapeutic aspects. Angiology 52, 759-762.
Mikhail, M.A., M'Hamdi, H., Welsh, J., Levicar, N., Marley, S.B., Nicholls, J.P., Habib, N.A., Louis, L.S., Fisk, N.M., and Gordon, M.Y. (2008). High frequency of fetal cells within a primitive stem cell population in maternal blood. Hum Reprod 23, 928-933.
Newman, P.J., Berndt, M.C., Gorski, J., White, G.C., 2nd, Lyman, S., Paddock, C., and Muller, W.A. (1990). PECAM-1 (CD31) cloning and relation to adhesion molecules of the immunoglobulin gene superfamily. Science 247, 1219-1222.
Nguyen Huu, S., Dubernard, G., Aractingi, S., and Khosrotehrani, K. (2006). Feta-maternal cell trafficking: a transfer of pregnancy associated progenitor cells. Stem Cell Rev 2, 111-116.
Nguyen Huu, S., Oster, M., Uzan, S., Chareyre, F., Aractingi, S., and Khosrotehrani, K. (2007). Maternal neoangiogenesis during pregnancy partly derives from fetal endothelial progenitor cells. Proc Natl Acad Sci USA 104, 1871-1876.

(56) References Cited

OTHER PUBLICATIONS

Niwa, H., Toyooka, Y., Shimosato, D., Strumpf, D., Takahashi, K., Yagi, R., and Rossant, J. (2005). Interaction between Oct3/4 and Cdx2 determines trophectoderm differentiation. Cell 123, 917-929.
Nussbaum, J., Minami, E., Laflamme, M.A., Virag, J.A., Ware, C.B., Masino, A., Muskheli, V., Pabon, L., Reinecke, H., and Murry, C.E. (2007). Transplantation of undifferentiated murine embryonic stem cells in the heart: teratoma formation and immune response. FASEB J 21, 1345-1357.
O'Donoghue, K., Choolani, M., Chan, J., de la Fuente, J., Kumar, S., Campagnoli, C., Bennett, P.R., Roberts, I.A., and Fisk, N.M. (2003). Identification of fetal mesenchymal stem cells in maternal blood: implications for non-invasive prenatal diagnosis. Mol Hum Reprod 9, 497-502.
Oh, H., Bradfute, S.B., Gallardo, T.D., Nakamura, T., Gaussin, V., Mishina, Y., Pocius, J., Michael, L.H., Behringer, R. R., Garry, D.J., et al. (2003). Cardiac progenitor cells from adult myocardium: homing, differentiation, and fusion after infarction. Proc Natl Acad Sci USA 100, 12313-12318.
Oh, H., Chi, X., Bradfute, S.B., Mishina, Y., Pocius, J., Michael, L.H., Behringer, R.R., Schwartz, R.J., Entman, M.L., and Schneider, M.D. (2004). Cardiac muscle plasticity in adult and embryo by heart-derived progenitor cells. Ann NY Acad Sci 1015, 182-189.
Orlic, D., Kajstura, J., Chimenti, S., Jakoniuk, 1., Anderson, S.M., Li, B., Pickel, J., McKay, R., NadalGinard, B., Bodine, D.M., et al. (2001). Bone marrow cells regenerate infarcted myocardium. Nature 410, 701-705.
Osada, H., Doi, S., Fukushima, T., Nakauchi, H., Seki, K., and Sekiya, S. (2001). Detection of fetal HPCs in maternal circulation after delivery. Transfusion 41, 499-503.
Ottersbach et al., The Murine placenta contains hematopoietic stem cells within the vascular labyrinth region. Developmental Cell, 8:377-387, 2005.
Ozawa et al., A novel method for purification of inner cell mass and trophectoderm cells from blastocysts using magnetic activated cell sorting. Fertility and Sterility, 95(2):799-802, 2011.
Parolini et al., Concise review: Isolation and characterization of cells from human term placdenta: Outcome of the first international workshop on placenta dervied stem cells. Stem Cells, 26:300-311, 2008.
PCT/US2012/063908 International Search Report and Written Opinion dated Apr. 23, 2013.
Perin. Evolving standards in cardiovascular care: Stem cell therapy for cardiovascular disease. Texas Heart Institute Journal, 33(2): 204-208, 2006.
Pfaffl MW. A new mathematical model for relative quantification in real-time RT-PCR. Nucleic Acids Res. 29(9):e45, 2001.
Pritchard and Bianchi, Fetal cell microchimerism in the maternal heart: Baby gives back. Circ. Res., 110(1):3-5, 2012.
Ralston, A., and Rossant, J. (2005). Genetic regulation of stem cell origins in the mouse embryo. Clin Genet 68, 106-112.
Ralston, A., Cox, B.J., Nishioka, N., Sasaki, H., Chea, E., Rugg-Gunn, P., Guo, G., Robson, P., Draper, J.S., and Rossant, J. (2010). Gata3 regulates trophoblast development downstream of Tead4 and in parallel to Cdx2. Development 137, 395-403.
Ridgway. The others inside you. New Scientist, 27-29, Jan. 9, 2016.
Ro, A., and Frishman, W.H. (2006). Peripartum cardiomyopathy. Cardiol Rev 14, 35-42.
Saavedra WF, Paolocci N, St John ME, Skat MW, Stewart GC, Xie JS, Harrison RW, Zeichner J, Mudrick D, Marban E, Kass DA, Hare JM. Imbalance between xanthine oxidase and nitric oxide synthase signaling pathways underlies mechanoenergetic uncoupling in the failing heart. CircRes.2002; 90:297-304.
Shake JG, Gruber PJ, Baumgartner WA, Senechal G, Meyers J, Redmond JM, Pittenger MF, Martin BJ. Mesenchymal stem cell implantation in a swine myocardial infarct model: Engraftment and functional effects. Ann Thorac Surg. 2002;73: 1919-1925; discussion 1926.
Shute. Beyond birth: A child's cells may help or harm the mother long after delivery. Scientific American. Retrieved from the Internet: URL:http://www.scientificamerican.com/article/fetalcells-microchimerism/?print=true. Retrieved Mar. 23, 2015.
Sperger, J.M., Chen, X., Draper, U.S., Antosiewicz, J.E., Chon, C.H., Jones, S.B., Brooks, J.D., Andrews, P.W., Brown, P.O., and Thomson, J.A. (2003). Gene expression patterns in human embryonic stem cells and human pluripotent germ cell tumors. Proc Natl Acad Sci USA 100, 13350-13355.
Stayton et al. (2005) Orthod. Craniofacial. Res., 8: 219-225.
Strumpf, et al., Cdx2 is required for correct cell fate specification and differentiation of trophectoderm in the mouse blastocyst. Development 132, 2093-2102, 2005.
Su, et al., Murine maternal cell microchimerism: analysis using real-time PCR and in vivo imaging. Biology of reproduction. 78(5): 883-887, 2008.
Tan, et al., Fetal microchimerism in the maternal mouse brain: a novel population of fetal progenitor or stem cells able to cross the blood-brain barrier? Stem Cells 23, 1443-1452, 2005.
Tanaka, et al., Promotion oftrophoblast stem cell proliferation by FGF4. Science 282, 2072-2075, 1998.
Terstappen, et al., Sequential generations of hematopoietic colonies derived from single non lineage-committed CD34+CD38– progenitor cells. Blood 77, 1218-1227, 1991.
Ueyama, T., Kasahara, H., Ishiwata, T., Nie, Q., and Izumo, S. (2003). Myocardin expression is regulated by Nkx2.5, and its function is required for cardiomyogenesis. Mol Cell Biol, 23, 9222-9232.
Ungerleider. Stem cells from placentas show potential in treating heart disease, multiple sclerosis, and more. Fast Company, Business and Innovation. Retrieved from the internet: URL:http://www.fastcom pany. com/17 43248/stem-cells-placentas-show-potential-treating-heartdisease-multiple-sclerosis-and-more. Retrieved on Mar. 23, 2015.
U.S. Appl. No. 13/671,396 Non Final Office Action dated Oct. 8, 2014.
U.S. Appl. No. 13/671,396 Office Action dated Feb. 13, 2017.
U.S. Appl. No. 13/671,396 Office Action dated May 17, 2016.
U.S. Appl. No. 13/671,396 Office Action dated Jun. 29, 2015.
Van Laake, et al., Human embryonic stem cell-derived cardiomyocytes survive and mature in the mouse heart and transiently improve function after myocardial infarction. Stem Cell Res 1, 9-24, 2007.
Wang, et al., Fetal cells in mother rats contribute to the remodeling of liver and kidney after injury. Biochem Biophys Res Commun 325, 961-967, 2004.
Weisman and Healy, "Myocardial Infarct Expansion, Infarct Extension, and Reinfarction: Pathophysiological Concepts", Progress in Cardiovascular Disease 30:73-110, 1987.
Williams. Circulation research "In this issue" anthology. Circulation Research, 113:e125-e156, 2013.
Woo et al., Therapeutic delivery of cyclin a2 induces myocardial regeneration and enhances cardiac function in ischemic heart failure. Circulation. 114:1206-1213, 2006.
Wu, et al., Origins and fates of cardiovascular progenitor cells. Cell 132, 537-543, 2008.
Xu, et al., Characterization and enrichment of cardiomyocytes derived from human embryonic stem cells. Circ Res 91, 501-508, 2002.
Yang, et al., Human cardiovascular progenitor cells develop from a KDR+ embryonic-stem-cell-derived population. Nature 453, 524-528, 2008.
Zimmer. The Blog: Mending broken hearts: Using embryonic stem cells to repair damage caused by heart attacks. published at: www.huffingtonpost.com/marc-zimmer/mending-brokenhearts-usi_b_5269288.html, 5 pages, Aug. 10, 2016.

* cited by examiner

| A | B | C | D | E | F | G | H | I | J |
|---|---|---|---|---|---|---|---|---|---|
| Time point | Sample | CT | $X_{GFP}$=Y-35.867/- | $X_{ApoB}$=Y-30.541/- | XApoB/XGFP{log DNA | DNA (ng) | DNA (pg) | Cell #s (6.25pg) | %Cell #s/heart |
| 2 wks post | No MI | 33.6 | 0.877321981 | -0.819579895 | -0.9341837 | 0.116363372 | 116.3633725 | 19.39389542 | 0.121211846 |
|  | Sham | 32.5 | 1.303018576 | -0.524863359 | -0.402805738 | 0.395543509 | 395.5435093 | 65.92391821 | 0.412024489 |
|  | MI | 28 | 3.044504644 | 0.680795199 | 0.223614439 | 1.673456544 | 1673.456544 | 278.9094241 | 1.7431839 |
|  |  |  |  |  |  |  |  |  |  |
| 1 wk post | No MI | 35.00 | 0.335526316 | -1.194673668 | -3.560596031 | 0.000275045 | 0.275045136 | 0.045840856 | 0.000286505 |
|  | Sham | 33.45 | 0.935371517 | -0.779391276 | -0.833242473 | 0.146810638 | 146.8106382 | 24.4684397 | 0.152927748 |
|  | MI | 29.67 | 2.398219814 | 0.233361912 | 0.097306306 | 1.251141144 | 1251.141144 | 208.5235241 | 1.303272025 |
|  |  |  | GFP Standard | ApoB Standard |  |  |  |  |  |
|  |  |  | y = -2.584x + 35.867 | y = -3.7324x + |  |  |  |  |  |
|  |  |  | $R^2$ = 0.994 | $R^2$ = 0.9867 |  |  |  |  |  |

FIG. 8

| Sample | CT | Average CT | STDEV | SEM | Average normalizer | Delta Ct | Delta Delta Ct | Fold change |
|---|---|---|---|---|---|---|---|---|
| Placenta-GAPDH | 22.83313 | 22.699232 | 0.124194105 | 0.0717035 | 22.699232 | | | |
| Placenta-GAPDH | 22.587812 | | | | | | | |
| Placenta-GAPDH | 22.676754 | | | | | | | |
| Heart-GAPDH | 16.958006 | 16.905454 | 0.074624554 | 0.043084507 | 16.905454 | | | |
| Heart-GAPDH | 16.938318 | | | | | | | |
| Heart-GAPDH | 16.820038 | | | | | | | |
| Placenta-Nkx2.5 | 39.856915 | 39.769009 | 0.124317857 | 0.071774948 | | 17.069777 | 11.484933 | 0.00034889 |
| Placenta-Nkx2.5 | Undetermined | | | | | | | 2 |
| Placenta-Nkx2.5 | 39.681103 | | | | | | | |
| Heart-Nkx2.5 | 22.515194 | 22.490298 | 0.037273612 | 0.02151993 | | 5.584844 | 0 | 1 |
| Heart-Nkx2.5 | 22.447445 | | | | | | | |
| Heart-Nkx2.5 | 22.508255 | | | | | | | |

FIG. 9

SEQUENCE LISTING

```
<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: RT-PCR primer

<400> SEQUENCE: 1
catcgagctg aagggcatc                                                  19

<210> SEQ ID NO 2
<211> LENGTH: 20
<212> TYPE: DNA
<213> ORGANISM: Artificial Sequence
<220> FEATURE:
<223> OTHER INFORMATION: RT-PCR primer

<400> SEQUENCE: 2
```

```
tgttgtggcg gatcttgaag                                              20

<210> SEQ ID NO 3
<211> LENGTH: 22
<212> TYPE: DNA
<213> ORGANISM: Artificial Sequence
<220> FEATURE:
<223> OTHER INFORMATION: RT-PCR primer

<400> SEQUENCE: 3
aaggctcatt ttcaacaatt cc                                           22

<210> SEQ ID NO 4
<211> LENGTH: 20
<212> TYPE: DNA
<213> ORGANISM: Artificial Sequence
<220> FEATURE:
<223> OTHER INFORMATION: RT-PCR primer

<400> SEQUENCE: 4
ggacacagac agaccagaac                                              20

<210> SEQ ID NO 5
<211> LENGTH: 20
<212> TYPE: DNA
<213> ORGANISM: Artificial Sequence
<220> FEATURE:
<223> OTHER INFORMATION: RT-PCR primer

<400> SEQUENCE: 5
gacaggtacc gctgttgctt                                              20

<210> SEQ ID NO 6
<211> LENGTH: 19
<212> TYPE: DNA
<213> ORGANISM: Artificial Sequence
<220> FEATURE:
<223> OTHER INFORMATION: RT-PCR primer

<400> SEQUENCE: 6
agcctacggt gaccctgac                                               19

<210> SEQ ID NO 7
<211> LENGTH: 19
<212> TYPE: DNA
<213> ORGANISM: Artificial Sequence
<220> FEATURE:
<223> OTHER INFORMATION: RT-PCR primer

<400> SEQUENCE: 7
cagcaacagg gtggtggac                                               19

<210> SEQ ID NO 8
<211> LENGTH: 23
<212> TYPE: DNA
<213> ORGANISM: Artificial Sequence
<220> FEATURE:
<223> OTHER INFORMATION: RT-PCR primer

<400> SEQUENCE: 8
ggatggaaat tgtgagggag atg                                          23
```

METHODS OF CARDIAC REPAIR

CROSS-REFERENCE

This application is a continuation of U.S. application Ser. No. 15/662,755, filed Jul. 28, 2017, which is a divisional of U.S. application Ser. No. 13/671,396, filed Nov. 7, 2012, which claims the benefit of U.S. Provisional Application No. 61/556,700, filed Nov. 7, 2011, which applications are incorporated herein by reference in their entirety.

SEQUENCE LISTING

The sequence listing of the present application is submitted electronically as an ST.25 formatted txt file with a file name "084284-00189_ST25.txt," creation date of Jan. 5, 2025, and a size of 1,83 bytes. This sequence listing submitted is part of the specification and is hereby incorporated by reference in its entirety.

STATEMENT OF FEDERAL FUNDING

Embodiments of the present application were made, in part, with U.S. government support under NHLBI (R01-HL 088255) awarded by the National Institutes of Health. The government has certain rights in the invention.

BACKGROUND OF THE INVENTION

Heart failure is the leading cause of hospitalization in the US and heart disease remains the number one killer in the industrialized world. Each year over 1.1 million Americans have a myocardial infarction ("MI"), typically caused by a heart attack, with median survival after onset only 1.7 years in men and 3.2 years in women. Typically, 225,000 people suffering MI die before reaching the hospital.

Myocardial infarctions result in an immediate depression in ventricular function and the infarctions may expand, thereby causing ventricular remodeling. In many patients, progressive myocardial infarct expansion and ventricular remodeling leads to deterioration of ventricular function and heart failure.

A myocardial infarction (MI) occurs when a coronary artery becomes occluded and can no longer supply blood to the myocardial tissue. When a MI occurs, the myocardial tissue that is no longer receiving adequate blood flow dies and is replaced with scar tissue. Within seconds of a myocardial infarction, the under-perfused myocardial cells no longer contract, leading to abnormal wall motion, high wall stresses within and surrounding the infarct, and depressed ventricular function. The infarct expansion and ventricular remodeling are caused by these high stresses at the junction between the infarcted tissue and the normal myocardium. These high stresses eventually kill or severely depress function in the still viable myocardial cells. Thus, a wave of dysfunctional tissue expands from the original myocardial infarct region.

The consequences of MI may be often severe and disabling. In addition to immediate hemodynamic effects, the infarcted tissue and the myocardium or cardiac tissue undergo three major processes: infarct expansion, infarct extension, and ventricular remodeling. The magnitude of the responses and the clinical significance relates to the size and location of the myocardial infarction (Weisman and Healy, "Myocardial Infarct Expansion, Infarct Extension, and Reinfarction: Pathophysiological Concepts", *Progress in Cardiovascular Disease* 1987; 30:73-110; Kelley et al., "Restraining Infarct Expansion Preserves Left Ventricular Geometry and Function After Acute Anteroapical Infarction," *Circulation* 1999, 99: 135-142). Myocardial infarctions that destroy a higher percentage of the normal myocardium, and myocardial infarctions that are located anteriorly on the heart generally become clinically significant.

SUMMARY OF THE INVENTION

Disclosed herein is a new approach towards the regeneration and repair of cardiac myocytes. The disclosed compositions and methods can be used in various clinical applications.

Provided herein is a composition comprising a population of cells and a pharmaceutically acceptable carrier for increasing cardiomyocyte formation, increase cardiomyocyte proliferation, increase cardiomyocyte cell cycle activation, increase mitotic index of cardiomyocytes, increase myofilament density, increase borderzone wall thickness, or a combination thereof, wherein said cells express one or more markers identified in Table 2 or in FIG. 5C. In one embodiment, the cells are derived from placenta. In another embodiment, the cells are progenitor cells or stem cells. In another embodiment, the cells express Cdx2, Cd9, Eomes, CD34, CD31, c-kit, or a combination thereof. In another embodiment, the cells express Cdx2 and Cd9.

Also provided herein is a composition comprising a population of cells and a pharmaceutically acceptable carrier for treating myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy, wherein said cells express one or more markers identified in Table 2 or in FIG. 5C. In one embodiment, the cells are derived from placenta. In another embodiment, the cells are progenitor cells or stem cells. In another embodiment, the cells express Cdx2, Cd9, Eomes, CD34, CD31, c-kit, or a combination thereof. In another embodiment, the cells express Cdx2 and Cd9.

Also provided herein is a composition comprising a population of cells and a pharmaceutically acceptable carrier for inducing cardiac regeneration, wherein said cells express one or more markers identified in Table 2 or in FIG. 5C. In one embodiment, the cells are derived from placenta. In another embodiment, the cells are progenitor cells or stem cells. In another embodiment, the cells express Cdx2, Cd9, Eomes, CD34, CD31, c-kit, or a combination thereof. In another embodiment, the cells express Cdx2 and Cd9. In another embodiment, the composition increases cardiomyocyte formation, increase cardiomyocyte proliferation, increase cardiomyocyte cell cycle activation, increase mitotic index of cardiomyocytes, increase myofilament density, increase borderzone wall thickness, or a combination thereof, when administered to a subject. In another embodiment, the composition treats myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy when administered to a subject.

One aspect of the invention is directed to a method for restoring cardiac function. In such methods an effective amount of a composition that includes Cdx2 stem cells and/or Cdx2 progenitor cells is introduced into the heart of a subject in need thereof. The Cdx2 cells can be an isolated Cdx2 cell population. In one embodiment, such cells are isolated from placental tissue. In addition to Cdx2 cells, the composition may also include various pharmaceutically acceptable carriers and/or adjuvants as described herein.

Another aspect provided herein is a method for restoring cardiac function comprising introducing an effective amount of a composition cells and a pharmaceutically acceptable carrier into a heart of a subject in need thereof, wherein said cells express one or more markers identified in Table 2 or in FIG. 5C. Also provided herein is a method of inducing cardiomyocyte regeneration, cardiac repair, vasculogenesis or cardiomyocyte differentiation, comprising contacting cells with injured heart tissue, wherein said cells express one or more markers identified in Table 2 or in FIG. 5C.

In one embodiment, the cells are derived from placenta. In another embodiment, the cells are progenitor cells or stem cells. In another embodiment, the cells express Cdx2, Cd9, Eomes, CD34, CD31, c-kit, or a combination thereof. In another embodiment, the cells express Cdx2 and Cd9.

Generally, a subject upon which the methods of the invention are to be performed will have been diagnosed with myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy. Alternatively, it will have been determined that a subject upon which the methods of the invention are performed is at risk for myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy based on assessment of the heart tissue and/or family history. In one embodiment, a subject has been diagnosed with myocardial infarction or at risk for heart failure.

Compositions described herein may be implanted into cardiac tissue of the subject. Alternatively, implantation can be via injection delivery or catheter-delivery.

The cardiac tissue into which the composition is introduced can be myocardium, endocardium, epicardium, connective tissue in the heart, or nervous tissue in the heart.

In various embodiments, the subject is an animal (e.g., a mammal) such as, for example, a human, a rodent (e.g., mice, rats, etc.), a primate (e.g., a gorilla, a chimpanzee, an orangutan, a monkey, etc.), a veterinary animal (e.g., a horse, a bull, a cow, a sheep, a pig, etc.), a domestic animal (e.g., a dog, a cat, etc.), a reptile, avians (e.g., chickens or turkeys, etc.), or any other animal in need of such treatment.

In various embodiments, the cell population increases cardiomyocyte formation, increases cardiomyocyte proliferation, increases cardiomyocyte cell cycle activation, increases mitotic index of cardiomyocytes, increases myofilament density, increases borderzone wall thickness, or a combination thereof.

Provided herein is a composition including a population of Cdx2 cells and a pharmaceutically acceptable carrier for the preparation of a medicament for inducing cardiac regeneration. In one embodiment, the cells are derived from placenta. In another embodiment, the cells are progenitor cells or stem cells. In another embodiment, the cells express Cdx2, and further express Cd9, Eomes, CD34, CD31, c-kit, or a combination thereof. In another embodiment, the cells express Cdx2 and Cd9.

In one embodiment, the composition increases cardiomyocyte formation, increase cardiomyocyte proliferation, increase cardiomyocyte cell cycle activation, increase mitotic index of cardiomyocytes, increase myofilament density, increase borderzone wall thickness, or a combination thereof, when administered to a subject.

In another embodiment, the composition treats myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy when administered to a subject.

Provided herein is a composition including a population of Cdx2 cells and a pharmaceutically acceptable carrier for the preparation of a medicament to increase cardiomyocyte formation, increase cardiomyocyte proliferation, increase cardiomyocyte cell cycle activation, increase mitotic index of cardiomyocytes, increase myofilament density, increase borderzone wall thickness, or a combination thereof. In one embodiment, the cells are derived from placenta. In another embodiment, the cells are progenitor cells or stem cells. In another embodiment, the cells express Cdx2, and further express Cd9, Eomes, CD34, CD31, c-kit or a combination thereof. In another embodiment, the cells express Cdx2 and Cd9.

Provided herein is a composition including a population of Cdx2 cells and a pharmaceutically acceptable carrier for the preparation of a medicament for treating myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy.

Provided herein is a composition including a population of Cdx2 cells and a pharmaceutically acceptable carrier for inducing cardiac regeneration. In one embodiment, the cells are derived from placenta. In another embodiment, the cells are progenitor cells or stem cells. In another embodiment, the cells express Cdx2, and further express Cd9, Eomes, CD34, CD31, c-kit, or a combination thereof. In another embodiment, the cells express Cdx2 and Cd9.

In one embodiment, the composition increases cardiomyocyte formation, increases cardiomyocyte proliferation, increases cardiomyocyte cell cycle activation, increases mitotic index of cardiomyocytes, increases myofilament density, increases borderzone wall thickness, or a combination thereof, when administered to a subject.

In another embodiment, the composition treats myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy when administered to a subject.

A composition including a population of Cdx2 cells and a pharmaceutically acceptable carrier to increase cardiomyocyte formation, increase cardiomyocyte proliferation, increase cardiomyocyte cell cycle activation, increase mitotic index of cardiomyocytes, increase myofilament density, increase borderzone wall thickness, or a combination thereof. In one embodiment, the cells are derived from placenta. In another embodiment, the cells are progenitor cells or stem cells. In another embodiment, the cells express Cdx2, and further express Cd9, Eomes, CD34, CD31, c-kit, or a combination thereof. In another embodiment, the cells express Cdx2 and Cd9.

A composition including a population of Cdx2 cells and a pharmaceutically acceptable carrier for treating myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy. In one embodiment, the cells are derived from placenta. In another embodiment, the cells are progenitor cells or stem cells. In another embodiment, the cells express Cdx2, and further express Cd9, Eomes, CD34, CD31, c-kit, or a combination thereof. In another embodiment, the cells express Cdx2 and Cd9.

One would understand that one or more additional excipients, carriers, adjuvants, cells, etc., may be added to the compositions described herein.

Compositions described herein may contain, for example, from about $1\times10^8$ to about $1\times10^2$ cells. Compositions may also contain, for example, from about $1\times10^6$ to about $1\times10^5$ cells. In one embodiment where additional cells are present in the composition, the amount of cells in the composition will generally contain about $1\times10^8$ to about $1\times10^2$ Cdx2 cells. In another embodiment, where additional cells are present in the composition, the composition will generally contain about $1\times10^6$ to about $1\times10^5$ Cdx2 cells.

Provided herein is a mouse model to study myocardial infarction and the role of fetal cells in treatment of cardiac injury. The model comprises (1) mating wild-type female mice with eGFP positive male mice to form eGFP positive fetuses; (2) inducing myocardial infarction in the pregnant mice at E12 days; (3) assessing maternal hearts for eGFP positive cells, wherein the presence of eGFP positive cells indicates migration of fetal cells to the material heart and/or assessing one or more symptoms of myocardial infarction. In one embodiment eGFP positive cells have differentiated and have formed endothelial cells, smooth muscle cells and/or cardiomyocytes.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the compositions and methods are set forth with particularity in the appended claims. A better understanding of the features and advantages of the present embodiments will be obtained by reference to the following detailed description that sets forth illustrative examples, in which the principles of the compositions and methods are utilized, and the accompanying drawings of which:

FIG. 1A) Schematic of the experimental protocol. FIG. 1B) Mice were sacrificed at several time points for molecular and cellular analyses to track eGFP+ cells in maternal hearts and assess their differentiation pathways. FIGS. 1C-D) Quantitative PCR demonstrates significantly greater levels of eGFP expression in pregnant mice subjected to cardiac injury {(1 week: 120.0±17.0; FIG. 1C) (2 weeks: 12.0±1.6; FIG. 1D), n=3} compared to shams {(1 week: 6.0±1.7) (2 weeks: 1.6±0.4), n=3} and non-infarcted controls {(1 week: 1.0±0.6) (2 weeks: 1.0±0.7), n=3}, error bars are standard error of the mean (s.e.m.).

FIG. 3A) Single cell sorting of eGFP+ fetal cells from maternal hearts into 96-well plates demonstrates clonal expansion with a clonal efficiency of ~8.3% on feeder cell layers made with WT neonatal cardiomyocytes. FIG. 3B) The number of cells on each day after initial plating is provided for each sample.

FIG. 4A) eGFP+ cells were sorted from cell suspensions prepared from various organs and tissues. FIG. 4B) Fetal cell numbers in injured heart and blood increased immediately after delivery. Representative FACS profiles are shown for eGFP+ cell sorting from injured heart, blood and non-injured organs with mean percentages of eGFP+ cells (minimum n=3). FIG. 4C) Mean percentages of fetal cells plus s.e.m. plotted for each organ as follows: MI Heart-1.10±0.90 before delivery (n=10), 6.32±0.90 after delivery (n=19), p=0.001; Blood-1.34±0.81 before delivery (n=10), 3.59±2.30 after delivery (n=15), p=NS; Placenta-35.6±11.47 after delivery (n=3). Very low to undetectable numbers are found for all other organs.

FIG. 5A) eGFP+ fetal cells were sorted from maternal hearts one week after injury. Percentages of eGFP+ cells expressing various stem/progenitor cell surface markers and transcription factors were quantitated using FACS analysis. FIG. 5B) Quantitation for each marker above was performed in triplicate and mean percentage plus s.e.m. was plotted as follows: Nkx2.5 79.69±8.08; CD31 46.40±8.77; Cdx2 38.39±5.70; Sca-1 20.73±0.80; c-Kit 25.39±2.99; Islet1 2.99±0.97; Pou5f1 1.97±0.82; Nanog 2.72±0.49; Sox2 23.52±1.85; CD34 14.90±2.97. FIG. 5C) eGFP+ cells were sorted from end-gestation placentas from three pregnant mice subjected to myocardial injury. RNA expression array of 92 pluripotency genes was performed; gene expression relative to GAPDH was plotted for genes with the highest expression levels. Of note, TS cell markers Cdx2 and Eomes are amongst genes with highest expression.

FIG. 8. Absolute quantification of GFP cells in whole hearts of pregnant female mice mated with GFP-transgenic males is shown. Standard curves were generated for both GFP and ApoB by plotting CT values for different quantities of known amounts of DNA from GFP transgenic mice versus the DNA quantity in nanograms (ng). In the first row, data for the 2 weeks time point are presented; in the second row, data for the 1 week time point are presented. Column A represents time point; Column B represents sample type; Column C depicts CT value (in triplicate averaged over 3 mice) for each sample; Column D represents the DNA quantity as extrapolated from the GFP standard curve for each experimental CT value; Column E is the DNA quantity as extrapolated from the ApoB standard curve; Column F is the ratio of values in E/values in D (normalizing to ApoB expression levels as described in learn.appliedbiosystems.com); Column G represents the inverse log of values in F to derive 'normalized' DNA quantity; Column H is the DNA quantity converted to pg; Column I is the number of GFP cells in that sample of DNA utilizing the mouse genome conversion factor for this strain of mouse as referred to in Fujiki et al., *Biol. Reprod*, 2008 and Column J represents the absolute percentage of GFP cells in the whole heart-1.3% cells of whole heart are GFP-positive at 1 week post-injury and 1.7% cells of whole heart are GFP-positive at 2 weeks post-injury.

FIG. 9. The results of Real time q-PCR. Nkx2. 5 gene expression in late term placenta of mouse with cardiac injury are shown relative to the positive control (E16.5 mouse heart).

FIG. 10A) illustrates a lentivirus with murine Cdx2 promoter driving expression of tdTomato that will be used for selecting Cdx2 cells from placenta tissues. FIG. 10B) illustrates a control lentivirus having the same backbone as in 10A, but utilizing a CMV promter to drive expression of tdTomato. FIG. 10C) illustrates flow cytometric analysis of lentiviral transduction in CT26. Wild type (WT) murine colon carcinoma cell line.

DETAILED DESCRIPTION OF THE INVENTION

Figure 1A:
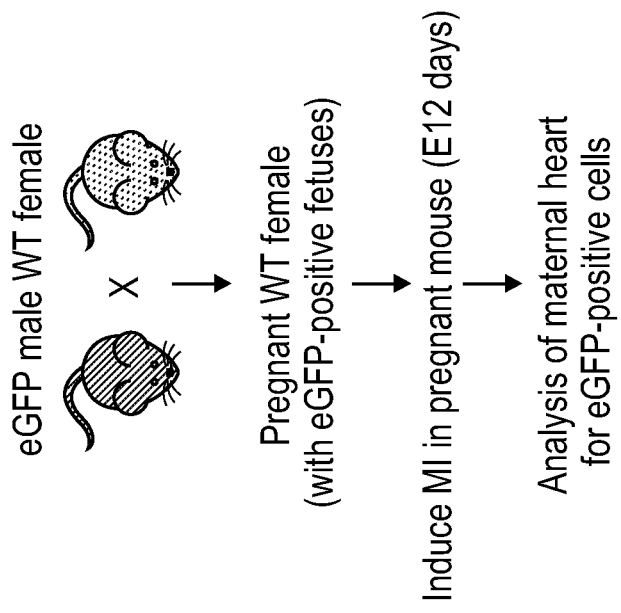
FIGS. 1A-D. Experimental model and tracking of eGFP+ fetal cells in maternal heart.

The studies described herein were inspired by the clinical observation that women with peripartum cardiomyopathy exhibit the highest rate of recovery amongst all known etiologies of heart failure. The present inventors postulated that fetal cells may contribute to this recovery and, therefore, created a new mouse model of experimental cardiac injury in pregnant females carrying eGFP-tagged fetuses.

Fetal cells enter the maternal circulation during pregnancy and may persist in maternal tissue for decades as microchimeras. Fetal maternal transfer of cells can involve multiple cell types, some with regenerative properties, but this phenomenon had not been previously explored in acute cardiac injury.

The present inventors determined for the first time that fetal cells selectively home (migrate) to injured maternal hearts and undergo differentiation into diverse cardiac lineages. Utilizing enhanced green fluorescent protein (eGFP)-tagged fetuses, engraftment of multipotent fetal cells in injury zones of maternal hearts was demonstrated. In vivo, eGFP+ fetal cells were found to form endothelial cells, smooth muscle cells, and cardiomyocytes. In vitro, cells isolated from maternal hearts recapitulate these differentiation pathways, additionally forming vascular tubes and beating cardiomyocytes in a fusion-independent manner. About 40% of fetal cells in the maternal heart were found to express Caudal-related homeobox2 (Cdx2).

Fetal maternal stem cell transfer was found to have an effect on maternal response to cardiac injury. Furthermore, Cdx2 cells were identified as a novel cell type for cardiovascular regenerative therapy.

The presently disclosed findings demonstrate for the first time that fetal cells selectively home to injured heart tissue and undergo differentiation into diverse cardiac lineages in vivo and in vitro. When fetal cells are isolated from the maternal heart, they form beating cardiomyocytes in vitro, in addition to forming vascular tubes, smooth muscle cells, and endothelial cells. Approximately 40% of the fetal cells entering the maternal heart are Cdx2-positive. Cdx2 has previously been known as a marker of trophoblast stem (TS) cells that give rise to placenta but not other organs.

The results of the studies described herein provide several new discoveries. Firstly, the phenomenon of fetal-maternal stem cell transfer has never previously been explored in the realm of acute cardiovascular disease. The present inventors determined that the fetal cells "sense" injury to the mother's heart and selectively home to the injury zone. Secondly, there has been a great deal of controversy in the stem cell field whether stem cells other than embryonic stem (ES) cells, can give rise to functional, beating cardiomyocytes. Live imaging (data not shown) by the present inventors using the new model described herein demonstrated that this is possible. Thirdly, Cdx2 cells can home to the injured heart and, in some embodiments, participate in cardiac differentiation in this injury model.

The present inventors were inspired by clinical observations that women with peripartum cardiomyopathy enjoy a high rate (~50%) of spontaneous recovery. This prompted the inventors to consider whether there may be a fetal or placental contribution to maternal cardiac repair. Although the new mouse injury model presented herein cannot precisely represent peripartum cardiomyopathy, it is a model of fetal maternal cell transfer which is believed to have identified appropriate cell types for cardiac regeneration. Briefly, mid-gestation myocardial infarction was induced in pregnant female mice and they were sacrificed at various time points. Cells of fetal origin, marked by green fluorescent protein, homed to the injured areas of the heart, but not to non-injured areas. They did not home to non-injured organs within the mouse either, and this suggests that precise signals are 'sensed' by the fetal cells which enable them to target diseased tissue specifically. Upon homing to the heart, they differentiated into diverse cardiac lineages, including endothelial cells, smooth muscle cells, and cardiomyocytes. In vitro analysis of fetal cells isolated from maternal hearts demonstrated that they can recapitulate these differentiation pathways, forming vascular tubes in a 3D collagen matrix and spontaneously beating cardiomyocytes when co-cultured with neonatal cardiomyocytes. Although fetal cells isolated from maternal heart express a variety of pluripotency markers, a notable new finding was the finding that ~40% expressed Caudal-related homeobox2 (Cdxc2), previously associated with trophoblast stem (TS) cells and other aspects of non-cardiac development. This knowledge will spur further investigations into a potential role for TS cells in cardiac regeneration and further studies of the signaling mechanisms of cells that 'naturally' home to the diseased heart.

With regards to impact, the data presented herein implicate isolating Cdx2 cells from placenta for therapeutic use in heart disease. This represents a significant advance in the field because isolation of cells from placenta avoids ethical concerns associated with ES cells as placenta is routinely discarded in labor and delivery rooms throughout the world. These concepts have far-reaching applications in the fields of stem cell research and regenerative therapy.

Microchimerism results when two genetically disparate populations of cells appear in the same tissue, organ, or individual. This can be due to transfusion of blood products, organ transplantation, or pregnancy. In this study, we refer to microchimerism derived from the bidirectional trafficking and stable long-term persistence of allogeneic fetal cells in the maternal host, a phenomenon that is common to many Eutheria. Microchimeric cells can modify immunological recognition or tolerance, affect the course and outcome of various diseases, and demonstrate stem cell-like or regenerative properties.

Fetal-maternal transfer of nucleated cells during pregnancy involves multiple cell types, some possessing multi-lineage potential and these cells may appear transiently or persist for decades after delivery in some women The long-term survival of fetal CD34+ hematopoietic stem/ progenitor cells, CD34+ and CD38+ lymphoid progenitors, CD3+ and CD14+ mononuclear cells, CD19+ and IgM+B lymphocyte precursor cells, CD45+ cells, desmin+ and mesenchymal stem cells have been reported in maternal blood and tissues (Bianchi et al., 1996; Campagnoli et al., 2001; Fujiki et al., 2009; Khosrotehrani et al., 2008; Mikhail et al., 2008; Nguyen Huu et al., 2006; O'Donoghue et al., 2003; Osada et al., 2001). The rodent brain contains fetal chimeric progenitor cells (Tan et al., 2005) and fetal cells with regenerative potential have been found in brain, liver, kidney, and lung injuries (Chen et al., 2001; Kleeberger et al., 2003; Wang et al., 2004). Fetal cells have also been found to participate in maternal neoangiogenesis during pregnancy at sites of skin inflammation (Nguyen Huu et al., 2007).

To the best of our knowledge, the phenomenon of fetal maternal stem cell transfer has never been explored in the realm of acute cardiac disease. One group has reported that cells of male fetus origin could be found in explanted hearts of two women with idiopathic dilated cardiomyopathy many years after a previous pregnancy (Bayes-Genis et al., 2005). This observational study did not determine whether the fetal cells contributed to the development of cardiomyopathy or if their presence represented an attempt at cardiac regeneration.

These clinical observations led the present inventors to consider that fetal or placental cells that enter the maternal circulation may be recruited to the sites of myocardial disease or injury to assist in repair. Further, identification of the cell types implicated in this process could be used for development of novel cell therapies for a broader spectrum of cardiovascular disease states. Significant controversy exists in the field of stem cell biology as to whether a variety of stem cell types other than embryonic stem (ES) cells can give rise to beating cardiomyocytes. The present studies illustrate for the first time that experimental myocardial injury, induced in a pregnant mouse, triggers the flux of fetal cells via the maternal circulation into the injured heart where they undergo differentiation into diverse cardiac cell fates. Fetal cells isolated from the maternal heart undergo clonal expansion and can differentiate into beating cardiomyocytes in vitro. A significant proportion of the fetal cells homing to the heart express Cdx2, thus, trophoblast stem cells may participate in organ repair after acute injury.

Fetal-maternal transfer of nucleated cells during pregnancy involves multiple cell types, some possessing multilineage potential, and these cells appear transiently or may persist for decades after delivery in some women. The long-term survival of fetal CD34+ hematopoietic stem/progenitor cells, CD34+ and CD38+ lymphoid progenitors, CD3+ and CD14+ mononuclear cells, CD19+ and IgM+B lymphocyte precursor cells, CD45+ cells, desmin+ and mesenchymal stem cells have been reported in maternal blood and tissues. Fetal chimeric progenitor cells have been found in rodent brain and additionally, fetal cells with regenerative potential have been found in brain, liver, kidney, and lung injuries. Fetal cells have also been found to participate in maternal neoangiogenesis during pregnancy at sites of skin inflammation.

Figure 5A:
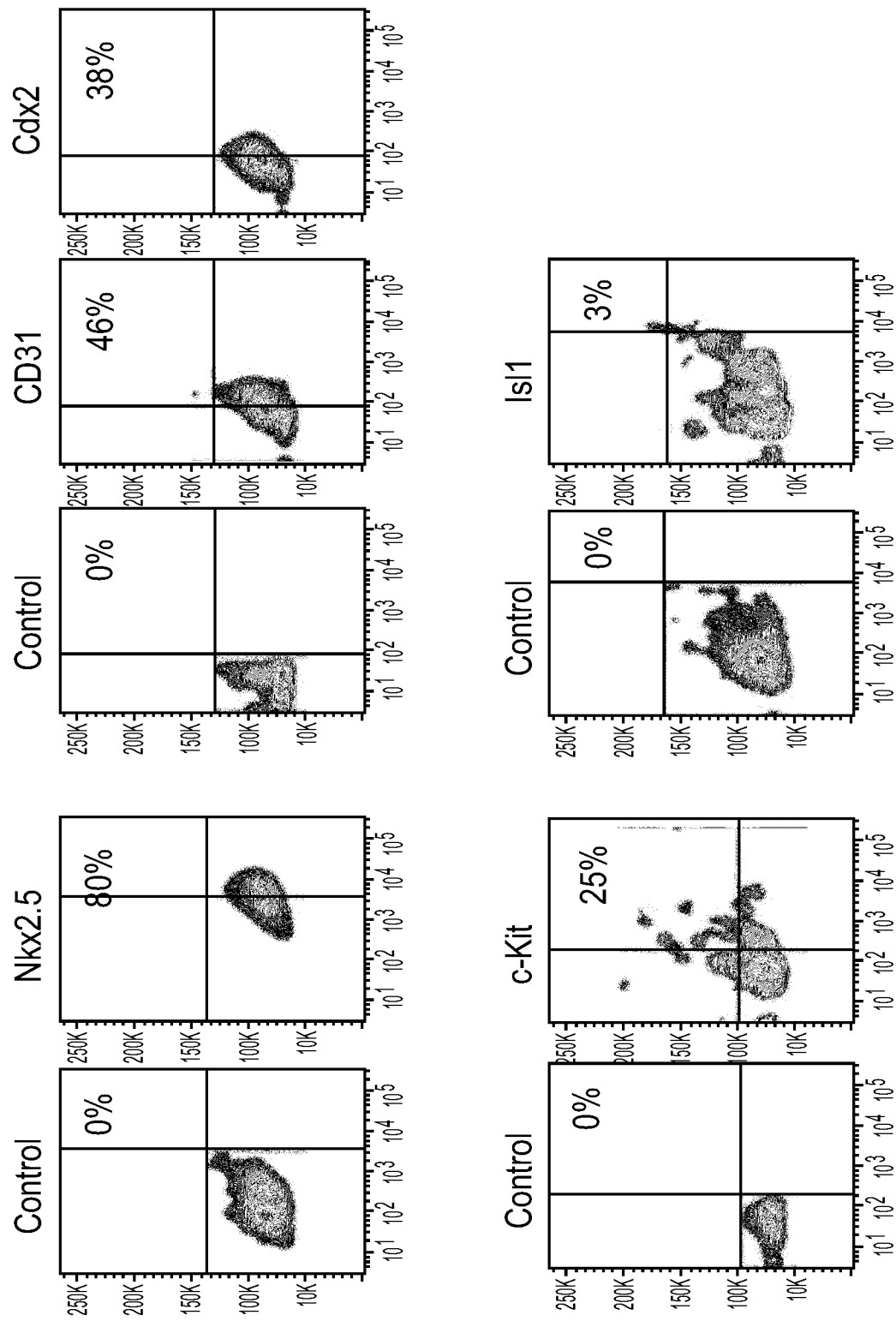
FIGS. 5A-C. Fetal cells selectively homing to injured maternal hearts express various stem cell markers, including Cdx2.
Figure 5A:
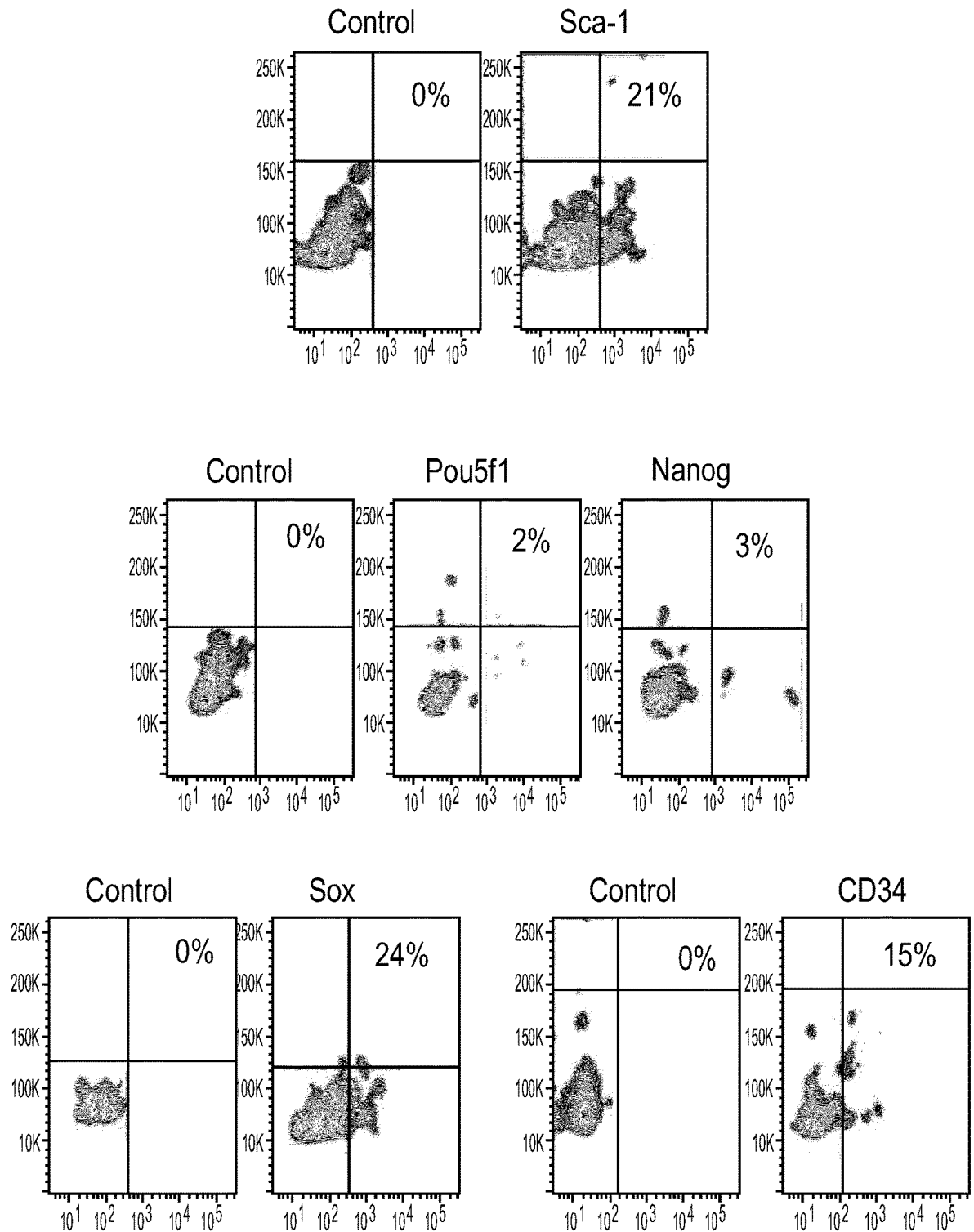

The selective homing of eGFP+ cells in the model presented herein to the site of maternal cardiac injury with lack of such homing to non-injured tissues points to the presence of precise signals sensed by cells of fetal origin that enable them to target diseased myocardium specifically, and to differentiate into diverse cardiac lineages (FIG. 5A). Most notable is their differentiation into functional cardiomyocytes that are able to beat in syncytium with neighboring cardiomyocytes (movie not shown), thus uncovering an evolutionary mechanism whereby a fetus may assist in protecting the mother's heart during and after pregnancy.

This observation led the present inventors to consider that there may be a fetal or placental contribution to counteract maternal cardiac injury. While the mouse injury model presented herein is not an absolutely precise representation of peripartum cardiomyopathy, it does provide a sound model system of murine fetomaternal microchimerism to identify appropriate cell types for cardiac regeneration.

To this end, a far greater spectrum of potential applications to the field of heart disease emerges from these studies. Prior to the present work described herein, the consensus in the field of cardiac regenerative medicine was that the ability of bone marrow-derived stem cells to differentiate into cardiomyocytes was questionable.

Several groups have demonstrated that ES cells (Nussbaum et al., 2007; van Laake et al., 2007; Xu et al., 2002; Yang et al., 2008) and endogenous populations of cardiac stem cells (Beltrami et al., 2003; Laugwitz et al., 2005a; Martin et al., 2004; Oh et al., 2003; Wu et al., 2008) have replicative and potentially regenerative capacities.

Notably, however, despite promising results with ES cells, there are ethical issues regarding the use of embryonic material as well as the tendency of ES cells to form teratomas (Nussbaum et al., 2007). Native cardiac progenitors, left in their natural milieu at their naturally occurring frequency, are clearly inadequate in reversing the downward spiral of events culminating in heart failure. Many of these progenitor types have not been reported to differentiate to functional beating cardiomyocytes when tested ex vivo.

In contrast, utilizing live imaging, the present inventors demonstrated herein for the first time that fetal cells differentiate into spontaneously beating cardiomyocytes after homing to the heart.

Figure 5B:
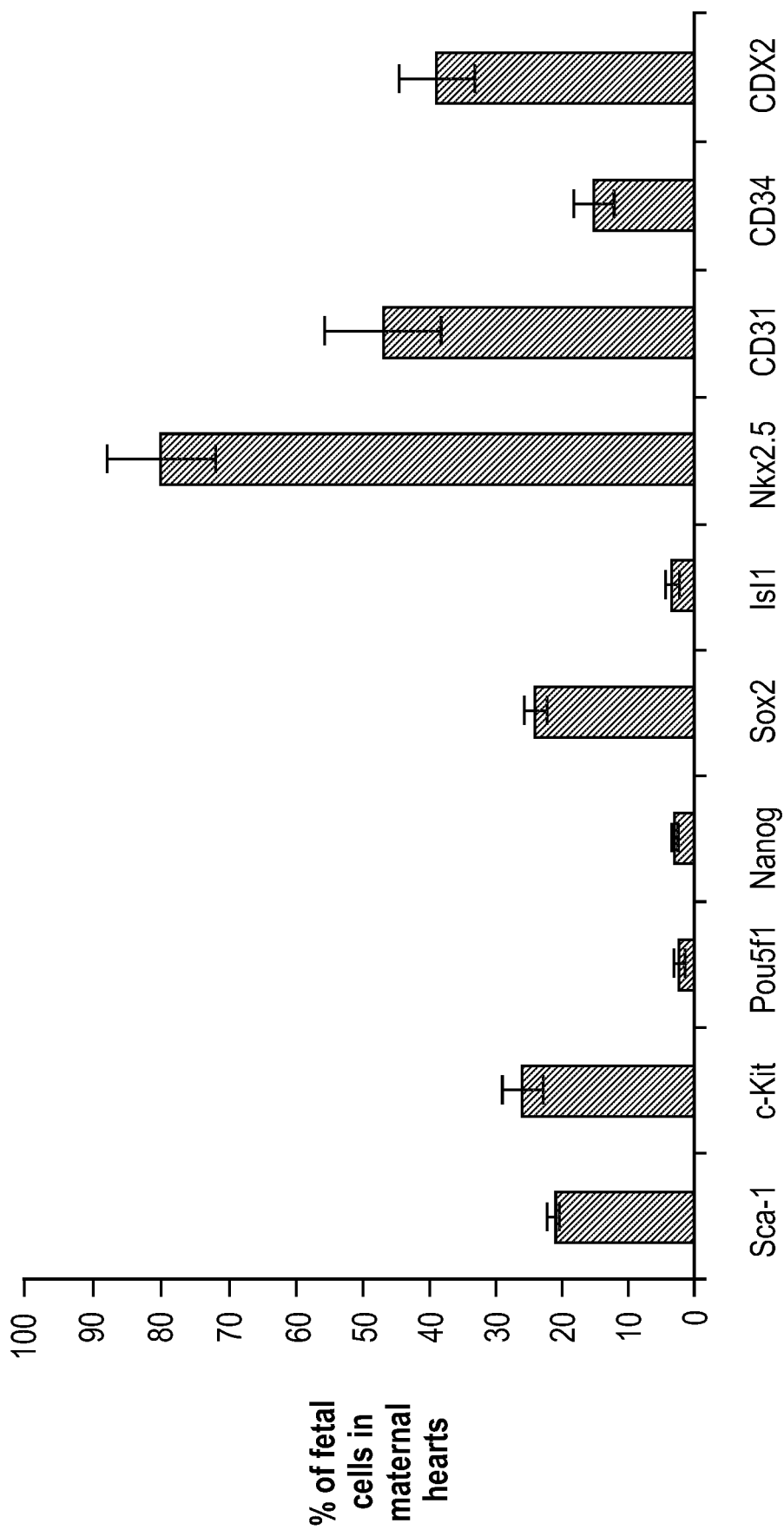

The identification of Cdx2 by the present inventors as a unique and highly prevalent marker expressed on fetal cells in the maternal myocardium offers a new perspective regarding the appropriate cell type to achieve these aims. The Cdx family of transcription factors consist of three mouse homologues (Cdx 1, 2, and 4) of the *Drosophila* caudal homeobox genes, which are involved in specifying cell position along the anteroposterior axis, with similar functions in the later developmental stages of the mouse embryo (Chawengsaksophak et al., 2004; Strumpf et al., 2005) as well as morphological specification of murine gut endoderm (Beck and Stringer, 2010; Chawengsaksophak et al., 1997). Cdx2 is also required for trophectoderm fate commitment in the developing blastocyst (Niwa et al., 2005; Ralston and Rossant, 2005; Strumpf et al., 2005) (FIG. 5B). The trophectoderm gives rise to the trophoblast stem cells which have previously been associated solely with differentiation to the placenta lineage (Ralston et al., 2010; Tanaka et al., 1998).

Bianchi and colleagues found that fetal cells that traffic to maternal blood and organs comprise a mixed population of progenitor and differentiated cells, with different relative proportions in different maternal organs (Fujiki et al., 2009) in a study that was performed in the non-injured state. The results presented herein point towards the transfer of several populations of progenitor cells. The present finding of Cdx2 cells of fetal or placental origin in the heart presents a cell type that is capable of cardiac differentiation under injury conditions that can be readily isolated from placenta.

Microchimerism results when two genetically disparate populations of cells appear in the same tissue, organ, or individual. This can be due to transfusion of blood products, organ transplantation, or pregnancy. As used herein, the term "microchimerism" refers to bidirectional trafficking and stable long-term persistence of allogeneic fetal cells in the maternal host. Microchimeric cells can modify immunological recognition or tolerance, affect the course and outcome of various diseases, and demonstrate stem cell-like or regenerative properties.

As use herein, the term "stem cell" refers to an undifferentiated, multipotent, self-renewing, cell. A stem cell is able to divide and, under appropriate conditions, has self-renewal capability and can include in its progeny daughter cells that can terminally differentiate into any of a variety of different cell types. Hence, the stem cell is "multipotent" because stem cell progeny have multiple differentiation pathways. A stem cell is capable of self maintenance, meaning that with each cell division, one daughter cell will also be on average a stem cell.

Non-stem cell progeny of a stem cell are typically referred to as "progenitor" cells, which are capable of giving rise to various cell types within one or more lineages. As used herein, the term "progenitor cell" refers to an undifferentiated cell derived from a stem cell, and is not itself a stem cell. Some progenitor cells can produce progeny that are capable of differentiating into more than one cell type. A distinguishing feature of a progenitor cell is that, unlike a stem cell, it does not exhibit self maintenance, and typically is thought to be committed to a particular path of differentiation and will, under appropriate conditions, eventually differentiate along this pathway.

Stem cells and progenitor cells derived from a particular tissue are referred to herein by reference to the tissue from which they were obtained. For example, stem cells and progenitor cells obtained from fetal tissue are referred to as "fetal stem cells" and "fetal progenitor cells," respectively. Fetal tissue includes, but is not limited to, placenta used to feed a fetus during pregnancy, and which is expelled following birth.

A "clonogenic population" refers to a population of cells derived from the same stem cell. A clonogenic population may include stem cells, progenitor cells, precursor cells, differentiated cells, or any combination thereof.

The terms, "isolated," "purified" and "enriched" indicate that the cells are removed from their normal tissue environment and are present at a higher concentration as compared to the normal tissue environment. Accordingly, an "isolated," "purified" or "enriched" cell population may further include cell types in addition to stem cells and/or progenitor cells and may include additional tissue components, and the terms "isolated," "purified" and "enriched" do not necessarily indicate the presence of only stem cells and progenitor cells. In one embodiment, an "isolated," "purified" or "enriched" cell population contains greater than about 75% of the stem cells and/or progenitor cells. For example, an "isolated," "purified" or "enriched" cell population contains greater than about 75%, about 80%, about 85%, about 90%, about 95%, about 97%, about 98% or more of the stem cells and/or progenitor cells.

Isolated tissue samples may be placed into culture without further processing, or they may be processed to release cells from other tissue components by any of a variety of different means or combinations thereof known in the art. Tissue may be physically processed, e.g., by cutting or mincing a tissue sample into smaller pieces. Cutting may be performed by any conventional means available, including, e.g., the use of scissors, scalpels, razor blades, needles, and other sharp instruments.

Tissue samples may be cultured in any of a variety of culture media capable of supporting cell viability, growth and/or attachment, such as serum-supplemented DMEM. In one embodiment, explant media (Iscove's Modified Dulbecco's IMDM with 10% fetal calf serum (FBS), 100 U/ml penicillin G, 100 µg/ml streptomycin, 2 mmol/L L-glutamine, and 0.1 mmol/L beta-mercaptoethanol) is used. Tissue samples may be cultured under standard environmental conditions such as 37° C. and 5% $CO_2$. Tissue samples may be cultured for a time sufficient for adherent cells to adhere and stem cells to migrate above the adherent cell layer, which may be, e.g., approximately one week, two weeks, three weeks or more. Generally, the age of donor tissue determines the time for culture: the older the tissue, the longer the time it takes for the stem cells to migrate out from the explant. Non-limiting representative examples of tissue and cell culture techniques useful for the present compositions and methods of use thereof are provided in the Examples below.

Tissue may also be processed by exposure to an enzyme preparation that facilitates the release of cells from other tissue components. Examples of such enzymes include, but are not limited to, matrix metalloproteinases, pronase, clostripain, trypsin-like, pepsin-like, neutral protease-type and collagenases. Suitable proteolytic enzymes are commercially available and are also described, for example, in U.S. Pat. Nos. 5,079,160; 6,589,728; 5,422,261; 5,424,208; and 5,322,790. In one embodiment, the enzyme preparation is a collagenase preparation or comprises collagenase. In other embodiments, the enzyme preparation comprises one or more of trypsin-like, pepsin-like, clostripain, and neutral protease-type enzymes. For example, one suitable enzyme preparation may include a mixture of 0.2% trypsin and 0.1% collagenase IV.

Stem cells and progenitor cells may be purified from other tissue components after, or concurrent with, the processing of a tissue sample. In one embodiment, stem cells and progenitor cells may be purified from other cells and tissue components after the tissue sample has been cultured under conditions suitable for cell growth and for a time sufficient to allow cells to adhere to the culture dish. Purification of cells may include, for example, obtaining cells that migrate from the tissue sample during culture and may be present in the culture media or loosely adhered to the adherent fibroblast layer. The cells may be obtained by routine methods, such as removing and centrifuging the media to pellet cells therein, and washing the cells remaining in the culture dish with a solution such as phosphate-buffered saline (PBS) or D-Hanks to remove those cells loosely attached to the adherent cell layer. This wash solution may then also be centrifuged to obtain cells.

Following isolation, a purified cell population may include at least 75%, at least 80%, at least 85%, at least 90%, at least 95%, at least 96%, at least 97%, at least 98%, at least 99%, or 100% of Cdx-2 bearing stem cells or progenitor cells. The cells may also, in some embodiments, be characterized by the presence of one or more of the following cell markers: CD31, Sca-1, c-Kit, Pou5F1, Nanog, Isil, Sox2, Nkx2.5, CD23 and Cdx2.

Cdx2 cells obtained from fetal placenta have been found by the present inventors to have stem cell characteristics as they contribute to multiple cell lineages. Cdx2 cells have been newly identified as progenitors for endothelial cells, smooth muscle cells and/or cardiomyocytes. Provided herein is a composition comprising Cdx2 cells or and one or more pharmaceutically acceptable carriers and/or adjuvants. The composition for delivery of cells includes the cells and can comprise a pharmaceutical carrier, preferably an aqueous carrier. A variety of aqueous carriers can be used, e.g., buffered saline and the like. These solutions are sterile and generally free of undesirable matter. These compositions can be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, albumin, anticoagulants such as CPD (citrate, phosphate, and dextrose), dextran, DMSO, combinations thereof, and the like. Biologically compatible carriers or excipients also include, but are not limited to, such as 5-azacytidine, cardiogenol C, or ascorbic acid. The concentration of active agent in these formulations can vary widely, and can be selected primarily based on fluid volumes, viscosities, body weight, and the like, in accordance with the particular mode of administration selected and the subject's needs.

In one aspect, purified cell populations are present within a composition adapted for, or suitable for, freezing and/or storage. For example, such a composition may further comprise fetal bovine serum and/or dimethylsulfoxide (DMSO).

In some embodiments, at least 75%, at least 80%, at least 85%, at least 90%, at least 95%, at least 96%, at least 97%, at least 98%, at least 99%, or 100% of the cells in a cell population described herein have the capacity to undergo differentiation into specialized cell types. For example, the cells are capable of forming endothelial cells, smooth muscle cells and/or cardiomyocytes.

Provided herein is a composition including a population of Cdx2 cells and a pharmaceutically acceptable carrier for the preparation of a medicament for inducing cardiac regeneration.

In one embodiment, the composition increases cardiomyocyte formation, increase cardiomyocyte proliferation, increase cardiomyocyte cell cycle activation, increase mitotic index of cardiomyocytes, increase myofilament density, increase borderzone wall thickness, or a combination thereof, when administered to a subject.

In another embodiment, the composition treats myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy when administered to a subject.

Provided herein is a composition including a population of Cdx2 cells and a pharmaceutically acceptable carrier for the preparation of a medicament for increasing cardiomyocyte formation, increase cardiomyocyte proliferation, increase cardiomyocyte cell cycle activation, increase mitotic index of cardiomyocytes, increase myofilament density, increase borderzone wall thickness, or a combination thereof.

Provided herein is a composition including a population of Cdx2 cells and a pharmaceutically acceptable carrier for the preparation of a medicament for treating myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy.

Provided herein is a composition including a population of Cdx2 cells and a pharmaceutically acceptable carrier for inducing cardiac regeneration.

In one embodiment, the composition increases cardiomyocyte formation, increase cardiomyocyte proliferation, increase cardiomyocyte cell cycle activation, increase mitotic index of cardiomyocytes, increase myofilament density, increase borderzone wall thickness, or a combination thereof, when administered to a subject.

In another embodiment, the composition treats myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy when administered to a subject.

A composition including a population of Cdx2 cells and a pharmaceutically acceptable carrier for increasing cardiomyocyte formation, increase cardiomyocyte proliferation, increase cardiomyocyte cell cycle activation, increase mitotic index of cardiomyocytes, increase myofilament density, increase borderzone wall thickness, or a combination thereof.

A composition including a population of Cdx2 cells and a pharmaceutically acceptable carrier for treating myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy.

Figure 5C:
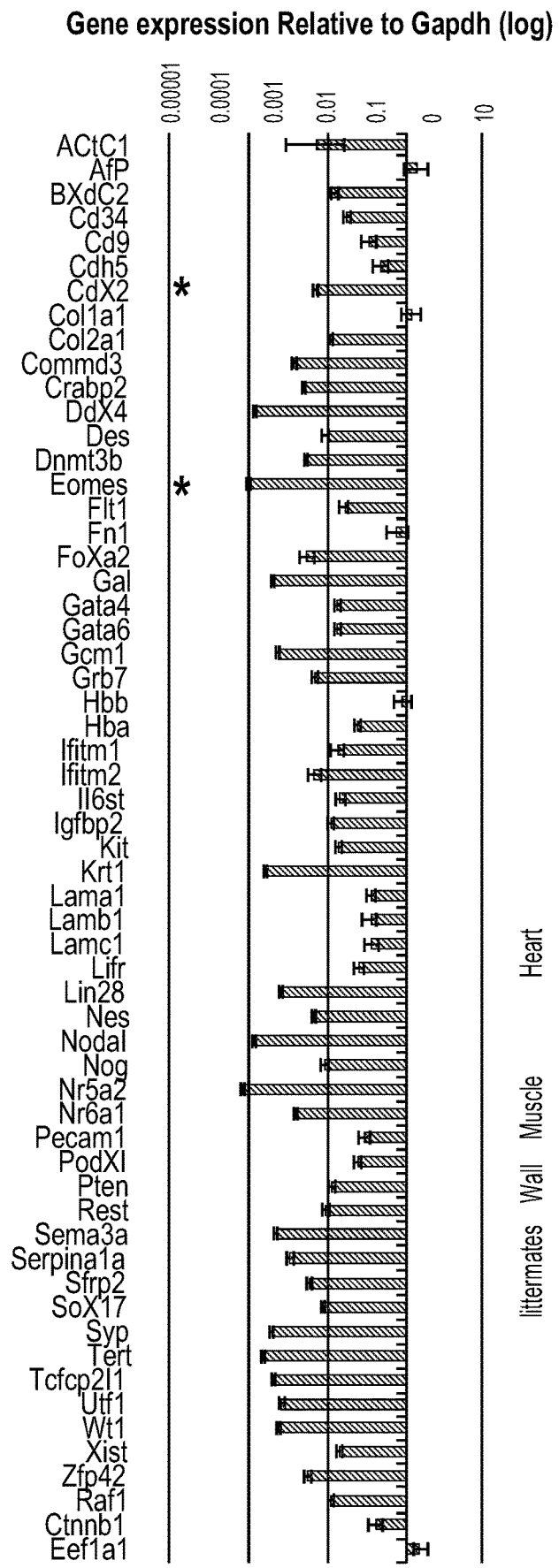

Provided herein is a composition comprising a population of cells and a pharmaceutically acceptable carrier for increasing cardiomyocyte formation, increase cardiomyocyte proliferation, increase cardiomyocyte cell cycle activation, increase mitotic index of cardiomyocytes, increase myofilament density, increase borderzone wall thickness, or a combination thereof, wherein said cells express one or more markers identified in Table 2 or in FIG. 5C. In one embodiment, the cells are derived from placenta. In another embodiment, the cells are progenitor cells or stem cells. In another embodiment, the cells express Cdx2, Cd9, Eomes, CD34, CD31, c-kit or a combination thereof. In another embodiment, the cells express Cdx2 and Cd9.

Also provided herein is a composition comprising a population of cells and a pharmaceutically acceptable carrier for treating myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy, wherein said cells express one or more markers identified in Table 2 or in FIG. 5C. In one embodiment, the cells are derived from placenta. In another embodiment, the cells are progenitor cells or stem cells. In another embodiment, the cells express Cdx2, Cd9, Eomes, CD34, CD31, c-kit or a combination thereof. In another embodiment, the cells express Cdx2 and Cd9.

Also provided herein is a composition comprising a population of cells and a pharmaceutically acceptable carrier for inducing cardiac regeneration, wherein said cells express one or more markers identified in Table 2 or in FIG. 5C. In one embodiment, the cells are derived from placenta. In another embodiment, the cells are progenitor cells or stem cells. In another embodiment, the cells express Cdx2, Cd9, Eomes, CD34, CD31, c-kit or a combination thereof. In another embodiment, the cells express Cdx2 and Cd9. In another embodiment, the composition increases cardiomyocyte formation, increase cardiomyocyte proliferation, increase cardiomyocyte cell cycle activation, increase mitotic index of cardiomyocytes, increase myofilament density, increase borderzone wall thickness, or a combination thereof, when administered to a subject. In another embodiment, the composition treats myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy when administered to a subject.

Provided herein is a composition comprising a population of cells and a pharmaceutically acceptable carrier for increasing cardiomyocyte formation, increase cardiomyocyte proliferation, increase cardiomyocyte cell cycle activation, increase mitotic index of cardiomyocytes, increase myofilament density, increase borderzone wall thickness, or a combination thereof, wherein said cells express one or more markers identified in Table 2 or in FIG. 5C. In one embodiment, the cells are derived from placenta. In another embodiment, the cells are progenitor cells or stem cells. In another embodiment, the cells express Cdx2, Cd9, Eomes, CD34, CD31, c-kit or a combination thereof. In another embodiment, the cells express Cdx2 and Cd9.

Also provided herein is a composition comprising a population of cells and a pharmaceutically acceptable carrier for treating myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy, wherein said cells express one or more markers identified in Table 2 or in FIG. 5C. In one embodiment, the cells are derived from placenta. In another embodiment, the cells are progenitor cells or stem cells. In another embodiment, the cells express Cdx2, Cd9, Eomes, CD34, CD31, c-kit, or a combination thereof. In another embodiment, the cells express Cdx2 and Cd9.

Also provided herein is a composition comprising a population of cells and a pharmaceutically acceptable carrier for inducing cardiac regeneration, wherein said cells express one or more markers identified in Table 2 or in FIG. 5C. In one embodiment, the cells are derived from placenta. In another embodiment, the cells are progenitor cells or stem cells. In another embodiment, the cells express Cdx2, Cd9, Eomes, CD34, CD31, c-kit or a combination thereof. In another embodiment, the cells express Cdx2 and Cd9. In another embodiment, the composition increases cardiomyocyte formation, increase cardiomyocyte proliferation, increase cardiomyocyte cell cycle activation, increase mitotic index of cardiomyocytes, increase myofilament density, increase borderzone wall thickness, or a combination thereof, when administered to a subject. In another embodiment, the composition treats myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy when administered to a subject.

One would understand that one or more additional excipients, carriers, adjuvants, cells, etc., may be added to the compositions described herein.

Compositions described herein may contain, for example, from about $1\times10^8$ to about $1\times10^2$ cells. Compositions may also contain, for example, from about $1\times10^6$ to about $1\times10^5$ cells. In one embodiment where additional cells are present in the composition, the amount of cells in the composition will generally contain about $1\times10^8$ to about $1\times10^2$ Cdx2 cells. In another embodiment, where additional cells are present in the composition, the composition will generally contain about $1\times10^6$ to about $1\times10^5$ Cdx2 cells.

One would understand that the amount of cells to be formulated in a composition or medicament for administration to a subject will depend upon the subject to be treated and the optimal dose or doses (in the case of repeat therapy) can be empirically determined by the treating doctor. For example, height, weight, age, gender, and overall physical condition may be considered by a doctor in determining a therapeutically effective amount of cells to administer. A therapeutically effective amount of cells is one which is capable of partially or fully restoring cardiac function and/or treating a heart condition. In one embodiment, the amount of composition comprises about from $1\times10^8$ to about $1\times10^2$ cells. In another embodiment, the amount of introduced composition comprises from about $1\times10^6$ to about $1\times10^5$ cells.

Given the pervasiveness of cardiac disease, there exists a need for therapeutic cell replacement strategies utilizing transplantation of autologous and/or exogenous cells for the treatment or prevention of heart disease. There also exists a need for mouse models that mimic myocardial infarction and which can be used to study the effect of cell transplantation therapies.

The present inventors determined for the first time that fetal cells selectively home (migrate) to injured maternal hearts and undergo differentiation into diverse cardiac lineages. Utilizing enhanced green fluorescent protein (eGFP) tagged fetuses, engraftment of multipotent fetal cells in injury zones of maternal hearts was demonstrated.

In vivo, eGFP+ fetal cells were found to form endothelial cells, smooth muscle cells, and cardiomyocytes. In vitro, fetal cells isolated from maternal hearts recapitulate these differentiation pathways, additionally forming vascular tubes and beating cardiomyocytes in a fusion-independent manner. Fetal maternal stem cell transfer was found to have an effect on maternal response to cardiac injury. Furthermore, Cdx2 cells were identified as a novel cell type for cardiovascular regenerative therapy.

The results of the studies described herein represent a significant advance in the field because isolation of cells from placenta avoids ethical concerns associated with ES cells as placenta is routinely discarded in labor and delivery rooms throughout the world. These concepts have far-reaching applications in the fields of stem cell research and regenerative therapy.

Provided herein is an isolated population of Cdx2 stem cells use in a composition or medicament for prevention or treatment of myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy. In one embodiment, the Cdx-2 bearing stem cells are derived from placenta. Provided herein is an isolated population of Cdx2 cells capable of restoring heart function and of forming endothelial cells, smooth muscle cells and/or cardiomyocytes. The approaches described herein are based, in part, upon application of the discovery of the ability of Cdx2 cells to home to the maternal heart and treat myocardial infarction in the model provided in the Examples below.

The present cells provide a novel cellular therapeutic agent for tissue repair. Such therapeutic tissue repair utilizes Cdx2 cells, which may be isolated from placental tissue and can be transplanted in an autologous manner. Methods and compositions described herein can be directed to, for example, cardiac repair.

Cdx2 cells introduced into the peri-infarct zone of infarcted mouse hearts can form endothelial cells, smooth muscle cells and/or cardiomyocytes and may induce myocardial repair, prevent heart failure, and induce cardiac remodeling. Thus, Cdx2 cells obtained from, for example, placental tissue, may be administered to a patient with, or at risk for, myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy.

Fetal stem cells naturally home to sites of maternal cardiac injury during pregnancy. The fetal cells are capable of differentiating into diverse cardiac lineages in vivo, including endothelial and smooth muscle cells and cardiomyocytes. They recapitulate these differentiation pathways in vitro, forming vascular tubes and spontaneously beating cardiomyocytes.

Cdx2 has been identified herein as a unique and highly prevalent marker expressed in fetal cells isolated from maternal myocardium, offering a new perspective regarding the appropriate cell type best suited for cardiovascular cell therapy. Cdx2 is required for trophectoderm fate commitment in the developing blastocyst. The trophectoderm gives rise to the trophoblast stem (TS) cells which have previously been associated solely with differentiation to the placenta lineage. Cdx2 cells may be isolated from end-gestation placentas and be utilized for allogeneic stem cell transplantation. These studies may be used for clinical testing and use of placenta-derived Cdx2 cells in the treatment of heart disease.

The present inventor is the first to propose isolation of Cdx2 cells and a heterogeneous mix of fetal-derived placenta cells from end-gestation mouse and human placentas, testing their differentiation properties in vitro, and identifying cell surface markers that may be used to facilitate further sorting.

A lentivirus has been constructed in which the murine Cdx2 promoter drives expression of the reporter gene tdTomato. The control lentivirus employs a cytomegalovirus promoter driving tdTomato. Cdx2 cells are isolated from murine and human placentas based on the red fluorescence of tdTomato. Single cell sorting into 96-well plates is performed to confirm clonality. These cells are then cultured on cardiac mesenchymal fibroblasts and neonatal cardiomyocytes to test for their ability to differentiate into endothelial cells, smooth muscle cells, and cardiomyocytes. Live-imaging microscopy is utilized to assess spontaneous beating of Cdx2 cell-derived cardiomyocytes. A heterogeneous mix of fetal-derived placenta cells that are mononuclear will also be tested in 96-well plates for clonality and in cell culture to examine their differentiation pathways. Murine fetal cells will be isolated using green-fluorescent protein (GFP) after wild-type virgin female mice are mated with transgenic GFP mice as described in the examples. Fetal-derived cells will also be isolated from human placentas by separating the fetal portion of placentas of first-time mothers who have given birth to males according to established techniques and confirming fetal identity with Y-chromosome FISH as described in the examples. Cdx2 cells will be isolated from human placenta tissues and proteomic approaches employed to search for novel cell surface markers that may be utilized for FACS sorting.

The present inventor also tested the ability of Cdx2 cells versus a heterogeneous mix of fetal-derived cells isolated from placenta to form cardiomyocytes and blood vessels in vivo and restore cardiac function via transplantation experiments in the post-myocardial infarction setting. Cdx2 cells versus heterogeneous fetal-derived placenta cells (hfpcs) cardiovascular differentiation potential in vivo and their ability to restore cardiac function in a rodent model.

Immunohistochemical approaches will be utilized to detect formation of endothelial cells, smooth muscle cells, and cardiomyocytes in the infarcted hearts. Cardiac function enhancement will be detected with magnetic resonance imaging (MRI).

The methods described herein involve intramyocardial transplantation of Cdx2 cells. Such therapeutic methods may repair and regenerate damaged myocardium and restore cardiac function after, for example, acute myocardial infarction and/or other ischemic or reperfusion related injuries. Methods generally include contacting a composition containing Cdx2 cells with cardiac tissue or cells. Contacting may occur via injection methods known in the art and described herein.

Provided herein is a method for restoring cardiac function comprising introducing an effective amount of a composition Cdx2 cells and a pharmaceutically acceptable carrier into a heart of a subject in need thereof. Restoration of cardiac function may include partial or complete restoration. In one embodiment, at least 50% of cardiac function is restored compared to a patient who does not receive such treatment. In another embodiment, about 50%, 60%, 70%, 75%, 80%, 85%, 90%, 95%, or 100% of cardiac function is restored. A subject receiving treatment may also be tested in various ways for cardiac health and have an improved result observed by echocardiography, multi-gated acquisition scan (MUGA) scan, nuclear stress test, radionuclide angiography, left ventricular angiography, MRI or ECG. In one embodiment, a patient's cardiac function does not worsen.

Provided herein is a method of inducing cardiomyocyte regeneration, cardiac repair, vasculogenesis or cardiomyocyte differentiation, including contacting a composition comprising Cdx2 cells with injured heart tissue. In one embodiment, Cdx2 cells are fetal stem cells which may be derived from placenta. The Cdx2 cells may be substantially isolated cells. In one embodiment, the Cdx2 cells represent at least about 75%, at least about 80%, at least about 85%, at least about 90%, at least about 95%, at least about 98%, at least about 99%, or 100% of the cells in the composition.

In such methods, a subject may be diagnosed with, or at risk for, myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy. In one embodiment, the subject is diagnosed with myocardial infarction. In another embodiment, the subject has, or is at risk for, heart failure.

Where compositions such as those described herein are utilized for treatment of a subject, introducing or contacting the composition with the heart of the subject can occur by implanting the composition into cardiac tissue of the subject. Alternatively, introducing or contacting the composition can occur via injecting the composition into the subject using conventional techniques in the art. Cardiac tissue to be treated according to the present methods includes, for example, myocardium, endocardium, epicardium, connective tissue in the heart, and nervous tissue in the heart. Animals such as mammals represent subjects to be treated with the presently disclosed compositions and methods. In one embodiment, the subject is a human, a veterinary animal, a primate, a domesticated animal, a reptile, or an avian. For example, a human subject may be treated with the disclosed compositions to restore cardiac function and to treat one or more heart-related conditions.

Provided herein is a method of preventing or treating a patient suffering from myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy comprising administering a composition comprising an isolated stem cell population comprising Cdx2 cells and a pharmaceutically acceptable carrier.

Another aspect provided herein is a method for restoring cardiac function comprising introducing an effective amount of a composition cells and a pharmaceutically acceptable carrier into a heart of a subject in need thereof, wherein said cells express one or more markers identified in Table 2 or in FIG. 5C. Also provided herein is a method of inducing cardiomyocyte regeneration, cardiac repair, vasculogenesis or cardiomyocyte differentiation, comprising contacting cells with injured heart tissue, wherein said cells express one or more markers identified in Table 2 or in FIG. 5C.

In one embodiment, the cells are derived from placenta. In another embodiment, the cells are progenitor cells or stem cells. In another embodiment, the cells express Cdx2, Cd9, Eomes, CD34, CD31, c-kit, or a combination thereof. In another embodiment, the cells express Cdx2 and Cd9.

Generally, a subject upon which the methods of the invention are to be performed will have been diagnosed with myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy. Alternatively, it will have been determined that a subject upon which the methods of the invention are performed is at risk for myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy based on assessment of the heart tissue and/or family history. In one embodiment, a subject has been diagnosed with myocardial infarction or at risk for heart failure.

One in this field of endeavor would understand that methods of prevention are intended for subjects that have a family history of heart attacks or may physically be predisposed to heart attacks. Thus, prevention encompasses administration of compositions described herein to a subject to prevent damage to the subject's heart and/or to prevent acute myocardial infarction. A subject that has been treated with such methods may experience an overall improvement in health. Additionally, cardiac function may be restored and/or improved as described above compared to lack of treatment.

In accordance with one embodiment, a composition containing Cdx2 cells is introduced into the cardiac tissue or cells a subject. Briefly, this method may be performed as follows: Cdx2 cells can be isolated from placenta using conventional means known in the art and described herein. Once isolated, the stem cells can be purified and/or expanded. The isolated cells can then be formulated as a composition (medicament) comprising the Cdx2 cells along with, for example, a pharmaceutically acceptable carrier. The composition (medicament) so formed can then be introduced into the heart tissue of a subject.

A subject to be treated with the disclosed compositions and methods will have been diagnosed as having, or being at risk for, a heart condition, disease, or disorder. Introduction of the composition can be according to methods described herein or known in the art. For example, the Cdx2 cell composition can be administered to a subject's heart by way of direct injection delivery or catheter delivery. Introduction of Cdx2 cells can be a single occurrence or can occur more than one time over a period of time selected by the attending physician.

The time course and number of occurrences of Cdx2 cell implantation into a subject's heart can be dictated by monitoring generation and/or regeneration of cardiac tissue, where such methods of assessment and devisement of treatment course is within the skill of the art of an attending physician.

Cardiac tissue into which Cdx2 cells can be introduced includes, but is not limited to, the myocardium of the heart (including cardiac muscle fibers, connective tissue (endomysium), nerve fibers, capillaries, and lymphatics); the endocardium of the heart (including endothelium, connective tissue, and fat cells); the epicardium of the heart (including fibroelastic connective tissue, blood vessels, lymphatics, nerve fibers, fat tissue, and a mesothelial membrane consisting of squamous epithelial cells); and any additional connective tissue (including the pericardium), blood vessels, lymphatics, fat cells, progenitor cells (e.g., side-population progenitor cells), and nervous tissue found in the heart. Cardiac muscle fibers are composed of chains of contiguous heart-muscle cells (cardiomyocytes), joined end to end at intercalated disks. These disks possess two kinds of cell junctions: expanded desmosomes extending along their transverse portions, and gap junctions, the largest of which lie along their longitudinal portions. Each of the above tissues can be selected as a target site for introduction of Cdx2 cells, either individually or in combination with other tissues.

A determination of the need for treatment will typically be assessed by a history and physical exam consistent with the myocardial defect, disorder, or injury at issue. Subjects with an identified need of therapy include those with diagnosed damaged or degenerated heart tissue (i.e., heart tissue which exhibits a pathological condition) or which are predisposed to damaged or degenerative heart tissue. Causes of heart tissue damage and/or degeneration include, but are not limited to, chronic heart damage, chronic heart failure, damage resulting from injury or trauma, damage resulting from a cardiotoxin, damage from radiation or oxidative free radicals, damage resulting from decreased blood flow, and myocardial infarction (such as a heart attack). In one embodiment, a subject in need of treatment according to the methods described herein has been diagnosed with degenerated heart tissue resulting from a myocardial infarction or heart failure.

It should be recognized that methods disclosed herein can be practiced in conjunction with existing myocardial therapies to effectively treat or prevent disease. The methods, compositions, and devices of the invention can include concurrent or sequential treatment with non-biologic and/or biologic drugs.

The subject receiving cardiac implantation of Cdx2 cells according to the methods described herein will usually have been diagnosed as having, or being at risk for, a heart condition, disease, or disorder. The methods of the invention can be useful to alleviate the symptoms of a variety of disorders, such as disorders associated with aberrant cell/tissue damage, ischemic disorders, and reperfusion related disorders. For example, the methods are useful in alleviating a symptom of myocardial infarction, chronic coronary ischemia, arteriosclerosis, congestive heart failure, dilated cardiomyopathy, restenosis, coronary artery disease, heart failure, arrhythmia, angina, atherosclerosis, hypertension, myocardial hypertrophy, or a combination thereof. The methods of the invention can also be useful to prevent the symptoms of a variety of disorders, such as disorders associated with aberrant cell/tissue damage, ischemic disorders, and reperfusion related disorders. For example, the methods are useful in preventing a symptom of myocardial infarction, chronic coronary ischemia, arteriosclerosis, congestive heart failure, dilated cardiomyopathy, restenosis, coronary artery disease, heart failure, arrhythmia, angina, atherosclerosis, hypertension, myocardial hypertrophy, or a combination thereof. The condition, disease, or disorder can be diagnosed and/or monitored, typically by a physician using standard methodologies.

Alleviation of one or more symptoms of the condition, disease, or disorder indicates that the composition confers a clinical benefit, such as a reduction in one or more of the following symptoms: shortness of breath, fluid retention, headaches, dizzy spells, chest pain, left shoulder or arm pain, and ventricular dysfunction. One would understand that a reduction of one more of the symptoms need not be 100% to provide therapeutic benefit to the subject being treated. Thus, in one embodiment, a reduction of about 50%, about 60%, about 70%, about 80%, about 90%, or more of one or more such symptoms may provide sufficient therapeutic relief to a patient.

With respect to methods of prevention, one would understand that prevention does not necessarily mean that a patient never experiences cardiac damage. Rather, prevention includes, but is not limited to, delay of onset of one or more symptoms compared to a lack of treatment. In one non-limiting example, a patient who has a family history of fatal heart attacks by 50 years of age may experience one or more symptoms described herein, but not experience a fatal heart attack or may experience a less severe heart attack compared to lack of treatment.

Cardiac cell/tissue damage is characterized, in part, by a loss of one or more cellular functions characteristic of the cardiac cell type which can lead to eventual cell death. For example, cell damage to a cardiomyocyte results in the loss of contractile function of the cell resulting in a loss of ventricular function of the heart tissue. An ischemic or reperfusion related injury results in tissue necrosis and scar formation. Injured myocardial tissue is defined for example by necrosis, scarring, or yellow softening of the myocardial tissue. Injured myocardial tissue leads to one or more of several mechanical complications of the heart, such as ventricular dysfunction, decreased forward cardiac output, as well as inflammation of the lining around the heart (i.e., pericarditis). Accordingly, regenerating injured myocardial tissue according to the methods described herein can result in histological and functional restoration of the tissue.

The methods described herein can promote generation and/or regeneration of heart tissue, and/or promote endogenous myocardial regeneration of heart tissue in a subject. Promoting generation of heart tissue generally includes, but is not limited to, activating, enhancing, facilitating, increasing, inducing, initiating, or stimulating the growth and/or proliferation of heart tissue, as well as activating, enhancing, facilitating, increasing, inducing, initiating, or stimulating the differentiation, growth, and/or proliferation of heart tissue cells. Thus, the methods include, for example, initiation of heart tissue generation, as well as facilitation or enhancement of heart tissue generation already in progress. Differentiation is generally understood as the cellular process by which cells become structurally and functionally specialized during development. Proliferation and growth, as used herein, generally refer to an increase in mass, volume, and/or thickness of heart tissue, as well as an increase in diameter, mass, or number of heart tissue cells. The term generation is understood to include the generation of new heart tissue and the regeneration of heart tissue where heart tissue previously existed.

Generation of new heart tissue and regeneration of heart tissue, resultant from the therapeutic methods described herein, can be detected and/or measured using conventional procedures in the art. Such procedures include, but are not limited to, Western blotting for heart-specific proteins, electron microscopy in conjunction with morphometry, simple assays to measure rate of cell proliferation (including trypan blue staining, the Cell Titer-Blue cell viability assay from Promega® (Madison, Wis.), the MTT cell proliferation assay from American Type Culture Collection (ATCC), differential staining with fluorescein diacetate and ethidium bromide/propidium iodide, estimation of ATP levels, flow-cytometry assays, etc.), and any of the methods, molecular procedures, and assays disclosed herein.

Cdx2 cells can be isolated from placental tissue, purified, and cultured as described in the present examples. Additional art-recognized methods of isolating, culturing, and differentiating stems cells are generally known in the art (see, e.g., Lanza et al., eds. (2004) Handbook of Stem Cells, Academic Press, ISBN 0124366430; Lanza et al., eds. (2005) Essentials of Stem Cell Biology, Academic Press, ISBN 0120884429; Saltzman (2004) Tissue Engineering: Engineering Principles for the Design of Replacement Organs and Tissues, Oxford ISBN 019514130X; Vunjak-Novakovic and Freshney, eds. (2006) Culture of Cells for Tissue Engineering, Wiley-Liss, ISBN 0471629359; Minuth et al. (2005) Tissue Engineering: From Cell Biology to Artificial Organs, John Wiley & Sons, ISBN 3527311866). Such methods can be utilized directly or adapted for use with the Cdx2 cells described herein.

It will be appreciated that the time between isolation, culture, expansion, and/or implantation may vary according to a particular application and/or a particular subject. Incubation (and subsequent replication and/or differentiation) of a composition containing Cdx2 cells can be, for example, at least in part in vitro, substantially in vitro, at least in part in vivo, or substantially in vivo. Determination of optimal culture time may be empirically determined.

Cdx2 cells can be derived from placenta of the same or different species as the transplant recipient. For example, progenitor cells can be derived from an animal, including but not limited to, mammals, reptiles, and avians such as, for example, horses, cows, dogs, cats, sheep, pigs, chickens, and humans. In one embodiment, Cdx2 cells are derived from human placenta. It is also contemplated that autologous Cdx2 cells may be obtained from the subject, into which the Cdx2 cells are re-introduced. Such autologous Cdx2 cells may be expanded and/or transformed, as described herein, before re-introduction to the host.

Cdx2 cells can be obtained by screening a plurality of cells from placental tissue. After screening, Cdx2 cells may be selected and prepared for transplantation. In one aspect, therapeutic Cdx2 cells may be expanded ex vivo (or in vitro) using, for example, standard methods used to culture Cdx2 cells and maintain stable cell lines. Alternatively, these cells can be expanded in vivo (i.e., after implantation). These cells can also be used for future transplantation procedures. The screened and isolated cells may, optionally, be further enriched for Cdx2 cells prior to transplantation. Methods to select for stem cells, for example Cdx2 cells, are well known in the art (e.g., MoFlow® Cell Sorter). For example, samples can be enriched by tagging cell-surface markers of undifferentiated Cdx2 cells with fluorescently labeled monoclonal antibodies and sorting via fluorescence-activated cell sorting (FACS). Alternatively, a sample of the Cdx2 cell-rich culture can be implanted without further enrichment.

Isolated Cdx2 cells can optionally be transformed with a heterologous nucleic acid so as to express a bioactive molecule or heterologous protein or to overexpress an endogenous protein. Transformation of stem cells, including Cdx2 cells, may be conducted using conventional methods in the art. In one non-limiting example, Cdx2 cells may be genetically modified to expresses a fluorescent protein marker (e.g., GFP, eGFP, BFP, CFP, YFP, RFP, etc.). Marker protein expression can be especially useful in implantation scenarios, as described herein, so as to monitor Cdx2 cell placement, retention, and replication in target tissue. As another example, Cdx2 cells may be transfected with one or more genetic sequences that are capable of reducing or eliminating an immune response in the host (e.g., expression of cell surface antigens such as class I and class II histocompatibility antigens may be suppressed). This may allow the transplanted cells to have reduced chance of rejection by the host, especially where the cells were from a different subject.

It may be desirable in some cases to increase levels of endogenous cell cycle regulators in Cdx2 cells and/or introduce exogenous cell cycle regulators into Cdx2 cells. For example, Cdx2 cells may be genetically engineered to express increased levels of cyclin A2 such that the cells have augmented and/or prolonged proliferative potential. The Cdx2 cells may be contacted with, or transformed to express or overexpress, a variety of cell cycle regulators so as to achieve similar results. Elevated levels of an active cell cycle regulator (e.g., a cyclin) in Cdx2 cells may be accomplished by, for example, contacting or transforming the Cdx2 cells with a cell cycle regulator protein, or a protein variant thereof, or a cell cycle regulator-associated agent. Cyclin proteins include, but are not necessarily limited to, cyclins A, B, C, D, and E. In one embodiment, the level of active cyclin A2 in the Cdx2 cell is elevated (see, e.g., U.S. Publication No. 2006/0160733 A1, which is incorporated by reference herein). Various transport agents and delivery systems may be employed so as to effect intracellular transport of the cyclin protein into Cdx2 cells (see, e.g., Stayton et al. (2005) Orthod. Craniofacial. Res., 8: 219-225). Isolated Cdx2 cells may be transduced with, for example, a lentiviral vector, retroviral vector, adenoviral vector, adeno-associated viral vector, or other vector system, overexpressing a cyclin gene. Several ways are available for increasing cyclin A2 expression including, but not limited to, transducing isolated Cdx2 cells with a lentiviral vector overexpressing a cyclin A2 gene, or providing cells with a nanoparticle that transfers cyclin A2, a protein composition or a small molecule that activates cyclin A2 in a cell. Any other method for inducing cyclin A2 using conventional means is also included herein.

In one embodiment, contact of Cdx2 cells with cyclin A2 may occur before, during, or after isolation and/or purification. Similarly, contact of Cdx2 cells with cyclin A2 may occur before, during, or after implantation into a subject. Cyclin A2 may be generated by synthesis of polypeptides in vitro, e.g., by chemical means, or in vitro translation of mRNA (see, e.g., U.S. Publication No. 2006/0160733). For example, a cyclin A2 may be synthesized by conventional methods in the art (see, e.g., Benoiton (2005) Chemistry of Peptide Synthesis, CRC, ISBN 1574444549; Goodman et al., eds. (2004) Synthesis Of Peptides And Peptidomimetics: Workbench Edition, Thieme Medical Pub, ISBN 1588903117).

Fetal Cdx2 cells may be cultured and/or implanted along with other progenitor cell types. For example, Cdx2 cells obtained from placenta may be cultured and/or implanted along with other stem cells, such as mesenchymal stem cells. Alternatively, or in addition, Cdx2 cells may be cultured and/or implanted along with cardiomyocytes.

Provided herein are methods for enhancing cardiac function in a subject in need thereof by introducing Cdx2 cells into the heart of a subject. Cdx2 cell compositions may be directly introduced into, or contacted with, cardiac tissue and/or cells. Introduction to the tissues or cells of a subject may occur ex vivo or in vivo. In one embodiment, compositions containing isolated cells are directly implanted into cardiac tissue of the subject, in vivo.

Therapeutic cells may be implanted into a subject using conventional methods (see, for example, the present Examples and Orlic et al. (2001) Nature, 410(6829): 701-705). For example, cells, or compositions comprising cells, may be introduced via direct injection (e.g., intermyocardial or intercoronary injection) or catheter-based delivery (e.g., intermyocardial, intercoronary, orcoronary sinus delivery). Intercoronary catheter delivery directly injects cells into heart tissue.

In one aspect, the cells may be transplanted along with a carrier material, such as collagen or fibrin glue or other scaffold materials. Such materials may improve cell retention and integration after implantation. Exemplary materials and methods for employing them are known in the art and are contemplated herein (see, e.g., Saltzman (2004) Tissue Engineering: Engineering Principles for the Design of Replacement Organs and Tissues, Oxford ISBN 019514130X; Vunjak-Novakovic and Freshney, eds. (2006) Culture of Cells for Tissue Engineering, Wiley-Liss, ISBN 0471629359; and Minuth et al. (2005) Tissue Engineering: From Cell Biology to Artificial Organs, John Wiley & Sons, ISBN 3527311866).

The amount of cells introduced into the heart tissue of the subject can be that amount sufficient to improve cardiac function, increase cardiomyocyte formation, and/or increase mitotic index of cardiomyocytes. For example, an effective amount may increase cardiomyocyte formation, increase cardiomyocyte proliferation, increase cardiomyocyte cell cycle activation, increased mitotic index of cardiomyocytes, increase myofilament density, increase borderzone wall thickness, or a combination thereof. An effective amount may form endothelial cells, smooth muscle cells, cardiomyocytes, or a combination thereof.

An effective amount of cells to be administered can be, for example, about $1\times10^8$ to about 100 cells. For example, about $1\times10^8$, about $1\times10^7$, about $1\times10^6$, about $1\times10^5$, about $1\times10^4$, about $1\times10^3$, about $1\times10^2$ cells can constitute an effective amount. In certain embodiments, about $1\times10^6$ to about $1\times10^5$ cells are introduced. The specific therapeutically effective dose level for any particular patient will depend upon a variety of factors including the disorder being treated and the severity of the disorder; activity of the specific cells employed; the specific composition employed; the age, body weight, general health, sex and diet of the patient; the time of administration; the route of administration; the duration of the treatment; drugs used in combination or coincidental with the specific composition employed and like factors well known in the medical arts. In certain instances, the total desired effective amount may be divided into multiple doses for purposes of administration. Consequently, single dose compositions may contain such amounts or submultiples thereof to make up the daily dose. It will be understood, however, that the total dosage of the compositions of the present invention will be decided by the attending physician within the scope of sound medical judgment.

Improving or enhancing cardiac function generally refers to improving, enhancing, augmenting, facilitating or increasing the performance, operation, or function of the heart and/or circulatory system of a subject. Improving or enhancing cardiac function may also refer to an improvement in one or more of the following symptoms: chest pain (typically radiating to the left arm or left side of the neck), shortness of breath, nausea, vomiting, palpitations, sweating, and anxiety. The amount of cells introduced into the heart tissue of the subject can be that amount sufficient to forming endothelial cells, smooth muscle cells and/cardiomyocytes. An improvement in cardiac function may be readily assessed and determined based on known procedures including, but limited to, an electrocardiogram (ECG), echocardiography, measuring volumetric ejection fraction using magnetic resonance imaging (MRI) and/or one or more blood tests. The most often used markers for blood tests are the creatine kinase-MB (CK-MB) fraction and the troponin levels.

Introduction of cell-containing compositions can occur as a single event or over a time course of treatment. For example, compositions can be administered daily, weekly, bi-weekly, or monthly. For treatment of acute conditions, the time course of treatment generally will be at least several days. Certain conditions may extend treatment from several days to several weeks. For example, treatment could extend over one week, two weeks, or three weeks. For chronic conditions or preventative treatments, treatment regimens may extend from several weeks to several months or even a year or more.

Provided herein is a mouse model to study myocardial infarction and the role of fetal cells in treatment of cardiac injury. The model comprises (1) mating wild-type female mice with eGFP positive male mice to form eGFP positive fetuses; (2) inducing myocardial infarction in the pregnant mice at E12 days; (3) assessing maternal hearts for eGFP positive cells, wherein the presence of eGFP positive cells indicates migration of fetal cells to the material heart and/or assessing one or more symptoms of myocardial infarction. In one embodiment eGFP positive cells have differentiated and have formed endothelial cells, smooth muscle cells and/or cardiomyocytes.

In order that those in the art may be better able to practice the compositions and methods described herein, the following examples are provided for illustration purposes.

EXAMPLES

Materials and Methods
Animals
Wild type (WT) B6CBA virgin female mice and enhanced green fluorescent protein (eGPF) transgenic male mice (C57Bl/6tg(ACTbeGFP)10 sb/J from Jackson Laboratories) were mated and pregnant females subjected to mid-gestation cardiac injury.). All mice used were between the ages of 3-6 months. All animal care was in compliance with the *Guide for the Care and Use of Laboratory Animals* published by the US National Institutes of Health, as well as institutional guidelines at Mount Sinai's School of Medicine. Initially, approximately 50 mice underwent LAD ligation surgery in order to determine the best time to induce injury. Embryonic day (E) 12 was chosen as an earlier time point would cause the mother to resorb the embryos due to the hypoxic insult. If the injury was induced later in gestation, the pregnant mouse dies due to the hemodynamic consequences of the volume overloaded state in late pregnancy. Once it was determined that E12 was the best time to induce injury, the survival rate was 70%. The deaths that did occur were likely due to the infarction surgery and this survival rate matches our previously published results in non-pregnant mice (Cheng et al., 2007).

DNA Extraction
Total DNA was extracted from whole maternal hearts utilizing the Blood and Tissue DNA extraction kit (Quiagen®, Valencia, CA).

RNA Extraction
Total RNA was extracted from cells/tissue using the RNeasy® RNA extraction micro kit (Quiagen®, Valencia, CA). cDNA was reverse transcribed from RNA using the SensiScript® RT kit (Quiagen®, Valencia, CA).

Real-Time Quantitative PCR
Quantitative PCR reactions were performed with iQ™ (SYBR® Green Supermix) on the iQ5 Real-Time PCR Detection System (Bio-Rad®, Hercules, CA). The PCR protocol consisted of one cycle at 95° C. (10 minutes) followed by 40 cycles of 95° C. (15 seconds) and 60° C. (1 minute). Fold changes in gene expression were determined using the comparative CT method (ΔΔCt method) (Pfaffl, 2001) with normalization to ApoB endogenous control.

Primers Used for RT-PCR Experiments are as Follow:

```
                                         (SEQ ID NO: 1)
GFP-forward       5'-CATCGAGCTGAAGGGCATC-3';

(SEQ ID NO: 2)
GFP-reverse       5'-TGTTGTGGCGGATCTTGAAG-3';

(SEQ ID NO: 3)
ApoB-forward      5'-AAGGCTCATTTTCAACAATTCC-3';

(SEQ ID NO: 4)
ApoB-reverse      5'-GGACACAGACAGACCAGAAC-3';

(SEQ ID NO: 5)
Nkx2.5-forward    5'-GACAGGTACCGCTGTTGCTT-3';

(SEQ ID NO: 6)
Nkx2.5-reverse    5'-AGCCTACGGTGACCCTGAC-3';

(SEQ ID NO: 7)
GAPDH-forward     5'-CAGCAACAGGGTGGTGGAC-3';
and (SEQ ID NO: 8)
GAPDH-reverse     5'-GGATGGAAATTGTGAGGGAGATG-3'.
```

Comparative CT Method (ΔΔCt Method)
Briefly, the threshold cycle number (CT) was obtained as the first cycle at which a statistically significant increase in fluorescence signal was detected. Data was normalized by subtracting the $C_T$ value of ApoB from that of the eGFP. Each reaction was done in triplicate and the CT values were averaged. The $\Delta\Delta C_T$ was calculated as the difference of the normalized $C_T$ values ($\Delta C_T$) of the treatment and control samples: $\Delta\Delta C_T = \Delta C_{T\ treatment} - \Delta C_{T\ control}$. $\Delta\Delta C_T$ was converted to fold of change by the following formula: fold of change=$2^{-\Delta\Delta C_T}$ (Pfaffl, 2001). The fold differences in gene expression are represented as the mean±SD. A minimum of three samples were run for each group at each time point (n=8 for experimental group at 1 week, n=5 at 2 weeks; n=3 for shams at 1 and 2 weeks; n=4 for non-infarcted control at 1 week, n=5 at 2 weeks). The fold-differences calculated using the ΔΔCT method are usually expressed as a range, which is a result of incorporating the error of the $\Delta\Delta C_T$ value into the fold difference calculation. The error bars represent the top and bottom range of the fold-difference. P-values were determined by a two-tailed paired Student's t test from the $\Delta C_T$ values.

Absolute Quantitation Method

Q-PCR was performed utilizing genomic DNA extracted from whole hearts. A sensitivity test (Fujiki et al., 2008; Su et al., 2008) was performed by mixing serial dilutions of DNA from GFP transgenic mouse hearts with each of three quantities of DNA from virgin female WT mouse hearts (0, 10,000, and 100,000 pg) and real-time PCR for amplification of GFP was performed. 1 GFP cell amongst 100,000 cells of WT background can be detected. GFP is present as two copies per cell in the transgenic mouse we are utilizing (Joshi et al., 2008) (See FIG. 8 legend for detailed description).

Immunofluorescence

Maternal heart ventricular 4-μm-thick sections were fixed for 20 minutes and then blocked with 10% donkey serum (Jackson Immunoresearch, West Grove, PA) for 1 hour (h) at room temperature (RT). Each section was incubated with the primary antibody for 1 hr at RT, followed by a secondary antibody for an additional 1 hat RT and counterstained with DAPI. Finally the sections were incubated for 5 minutes with Sudan Black (0.7% in 70% EtOH) and cover-slipped with mounting media (DAKO, Carpinteria, CA). Slides were imaged using a Zeiss® LSM-510 Meta confocal microscope (Carl Zeiss®, Munich Germany).

The following primary antibodies were used for staining: rabbit anti-GFP (ABCAM #AB6556, Cambridge, MA), mouse anti-alpha sarcomeric actin (Millipore Sigma® #A2172, St. Louis, MO), mouse anti-alpha sarcomeric actinin (Santa Cruz #15335, Santa Cruz, CA), mouse anti-cardiac troponin-T (ABCAM #AB45932), mouse anti-alpha-smooth muscle actin (Millipore Sigma® #A2547), mouse anti-smooth muscle myosin IgG (Biomedical Technologies Inc #BT562, Stoughton, MA), rat anti-CD3 1 (BD #553370, San Jose, CA), rat anti-VE-Cadherin (RDI #RDI-MCD144-1 1D4, Acton, MA). Alexa-488 and Alexa-568 (Alexa Fluor®) secondary antibodies were purchased from Molecular Probes® (Invitrogen®, Carlsbad, CA).

Isolation of Maternal Cardiac Cells

Chest wall was opened to expose heart which was perfused with 10 mL PBS, using a 23-gauge needle. Entire heart was dissected out (atria and ventricle) and extraneous tissue removed. Small amounts of serum-free medium (DMEM, Cellgro®, Manassas, VA) was added to prevent heart from drying out. Hearts from 3-4 adult mice were minced and placed in serum-free medium. Tissue was digested with Pronase at 1 mg/ml (Calbiochem®, Gibbstown, NJ) in a spinning incubator for 1 h at 37° C. Supernatant was removed and 5 mL of warm (37° C.) complete medium (DMEM supplemented with 10% fetal bovine serum [Cellgro®, Manassas, VA]) was added to the tube. (No glycine was added to inactivate the pronase, as the serum in the medium does this). Skeletal/cardiac muscle was triturated in the medium. During trituration, small aliquots of tendon-free solution were transferred to an empty 50 mL tube. Above procedure was repeated by adding 5 mL aliquots of medium to the tube every few triturations until a final tendon-free volume of 35-45 mL was achieved. Solution was filtered through a 70 micron mesh filter to remove small pieces of tendon. Filtered solution was spun at 3,000 rpm for 5 minutes. Pellet was resuspended in 3 mL of medium then 21 mL of red blood cell (RBC) lysis buffer (eBiosciences®, San Diego, CA) was added. After inverting a few times, filtered solution was spun at 3,000 rpm for 5 min. Supernatant was removed and the pellet was resuspended in 1 mL lx PBS with antibiotics. Cells were counted.

FACS

Cells were sorted utilizing a MoFlo® high speed cell sorter (Dako Cytomation, Carpinteria CA). Both eGFP+ (cells of fetal origin) and eGFP− (cells of maternal origin) populations were collected. Data analysis was performed using FlowJo® Software (Tree Star, Ashland, OR).

Flow Cytometry Cell Analysis

Analysis of specific cell markers on previously sorted eGFP+ cells was performed utilizing the BD LSR II (BD BIOSCIENCES, San Jose, CA). For intracellular cell markers cells were permeabilized using Triton®-X prior to antibody staining.

The following antibodies were used for staining: anti-Seal (eBioscience® #17-5981-81), anti-c-kit (eBioscience® #27-1171-81), anti-oct4 (eBioscience® #12-5841-80), anti-nanog (eBioscience® #51-5761-80), ant-sox2 (Millipore® #MAB4343, Billerica, MA), Isletl (Hybridoma bank #39.4D5-s, Iowa City, IO), anti-nkx2.5 (Santa Cruz #sc-14033), anti-CD3 1 (Santa Cruz #sc-1506), anti-CD34 (eBioscience® #56-0341-82), anti-cdx2 (Santa Cruz #194 78).

Cell Culture

Differentiation of eGFP+ Cells into Endothelial Cells and Smooth Muscle Cells

CMFs were prepared by isolating cardiac cells from 1 day old WT neonatal pups. Cells were enriched for CMFs by spinning at low speeds (800 rpm). The supernatant (which primarily contains CMFs) was plated for 1 hour on culture dishes to allow CMFs to attach. The supernatant, now containing residual cardiomyocytes, was discarded. CMFs were incubated at 37° C. until confluent. CMFs were treated with Mitomycin C (MP BIOMEDICALS, Solon, OH) to inhibit proliferation, incubated at 37° C. in complete medium for 24 hours and then used as feeders. FACS sorted eGFP+ cells were cultured on the CMFs and monitored for a period of 3-4 weeks. Live cell imaging was performed using an Olympus® IX-70 Live cell imaging system (Olympus®, Center Valley PA).

Differentiation of eGFP+ Cells into Cardiomyocytes

Cardiomyocyte feeders were prepared by isolating cardiac cells from 1 day old cyclin A2 transgenic mice as these cardiomyocytes can be passaged and remain viable in culture indefinitely. Cells were enriched for cardiomyocytes by spinning at low speeds (800 rpm).

The pellet (which primarily contains cardiomyocytes) was resuspended in complete medium and plated on culture dishes to allow residual CMFs to attach. The supernatant containing the cardiomyocytes was transferred to a new culture dish and then incubated at 37° C. Feeders were ready for experiments after 24 hours. EGFP+ cells were cultured on cardiomyocyte feeders and monitored over a 4-5 week period. Live cell imaging was performed using an Olympus® IX-70 Live cell imaging system (Olympus®, Center Valley PA).

Immunofluorescence

Cells were cultured in chamber slides for 4-5 weeks and fixed with 4% paraformaldehyde (PFA) for 20 minutes and then stained. Cells were incubated with primary antibody for 1 hour at RT, washed three times and then incubated with a secondary antibody for an additional hour at room temperature. After staining, the cells were washed three times, cover-slipped with Dako® mounting media and fluorescence was visualized using a Zeiss® Axiophot2 fluorescence microscope (Carl Zeiss®, Munich Germany).

Clonal Assay

Single eGFP+ cells isolated from injured maternal hearts were seeded in 96-well plates containing feeders (cardiomyocytes or CMF s) with complete medium. The FACSAria® BCL2 flow cytometer (BD BIOSCIENCES, San Jose, CA) was utilized to sort single eGFP+ cells into 96 well plates. Cells were monitored daily to assay clonal expansion. Medium was changed every 3 days. After 14 days in culture, cells were fixed using 4% PFA and subjected to analysis.

Spectral Profile

Spectral scanning was performed using a Leica® Microsystems (Leica®, Mannheim, Germany) TCS SP5 confocal microscope. Images were collected using the lambda scan mode from 545 nm-705 nm with a 10 nm bandwidth per image. The 543 nm HeNe laser was used for excitation and images were collected at 512×512 pixels using the 63$x$/1.4NA HCX PL APO oil lens. Regions of interest (ROis) were selected around both sample and control cells. The mean intensity vs. wavelength for each respective ROI was then plotted on a graph and compared to the Alexa Fluor® 568 spectral profile.

XY Chromosome Analysis

To prepare the slide containing interphase nuclei for FISH analysis, it was first rinsed in 2×SSC/0.1 3/4NP-40 for 2 min at room temperature. The slide was then dehydrated in an ethanol series and air-dried. Ready to Use (RTU) whole chromosome paint (WCP) mouse DNA probes for chromosomes X and Y (Cambio Ltd., Cambridge, UK) were mixed together and added to the slide. The interphase nuclei and probe were co-denatured for 5 minutes at 73° C. and hybridized for 48 hours at 37° C. The slide was then washed, to remove non-bound probe, in 0.4×SSC/0.3% NP-40 for 2 min at 72° C. and 2×SSC/0.1 3/4NP-40 for 2 min at room temperature and air-dried. The slide was mounted with a coverslip using DAPI II/Anti-fade (Abbott® Molecular, Des Plaines, Illinois). Images were obtained using Zeiss® Axioplan 2 fluorescent microscope with Cytovision® software (Genetix Corp, San Jose, CA). Cy3-Orange, Absorption Max →550 nm, Fluorescence Max →570 nm, FITC-Green, Absorption Max→494 nm, Fluorescence Max→520 nm.

TaqMan® Array for Pluripotent Genes

TaqMan® Array Gene Signature plates (Applied Biosystems®, Carlsbad, CA) contain 92 assays to stem cell associated genes. Total RNA was extracted from FACS isolated eGFP+ cells from placenta. Relative gene expression was determined using a two-step quantitative real-time PCR according to the manufacturer's instructions.

Data Analysis

Statistical analysis was performed with the student's t-test.

Example 1: Fetal Cells Home to and Engraft in Injured Maternal Myocardium

Wild-type (WT) virgin female mice, age 3-6 months, were crossed with heterozygous eGFP transgenic male mice. The female mice underwent ligation of the left anterior descending (LAD) artery in order to induce an anterolateral myocardial infarction (MI) at gestation day 12 (FIG. 1A). This results in approximately 50% left ventricular infarction. In accordance with Mendelian autosomal inheritance, approximately 50% of embryos were eGFP+.

Figure 1B:
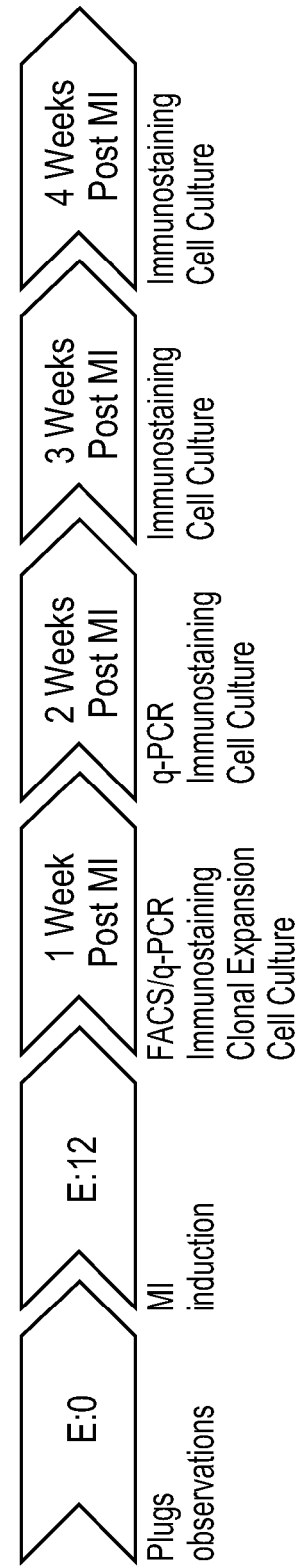
Figure 1C:
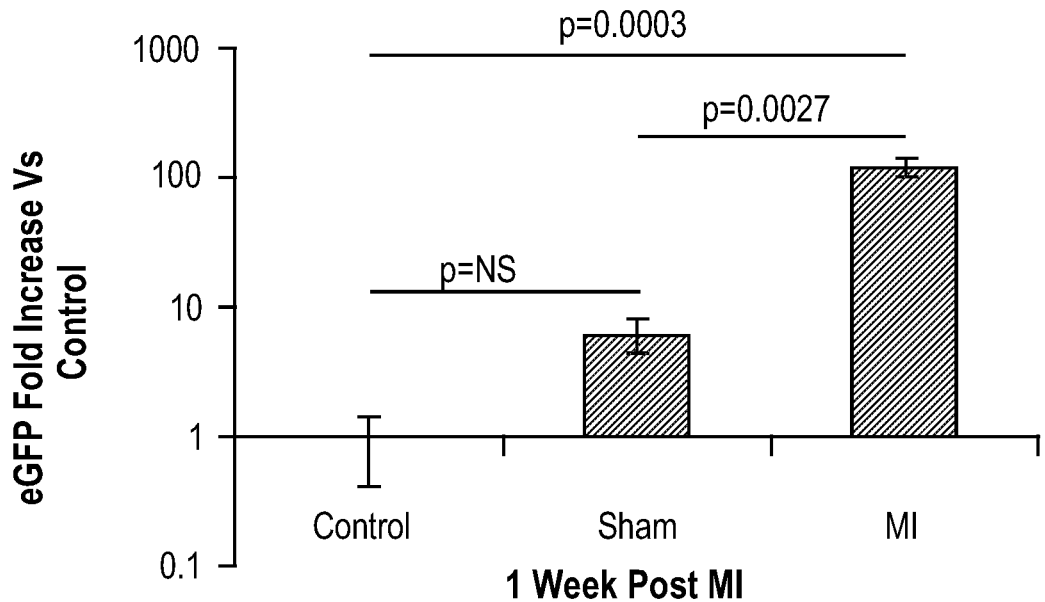
Figure 1D:
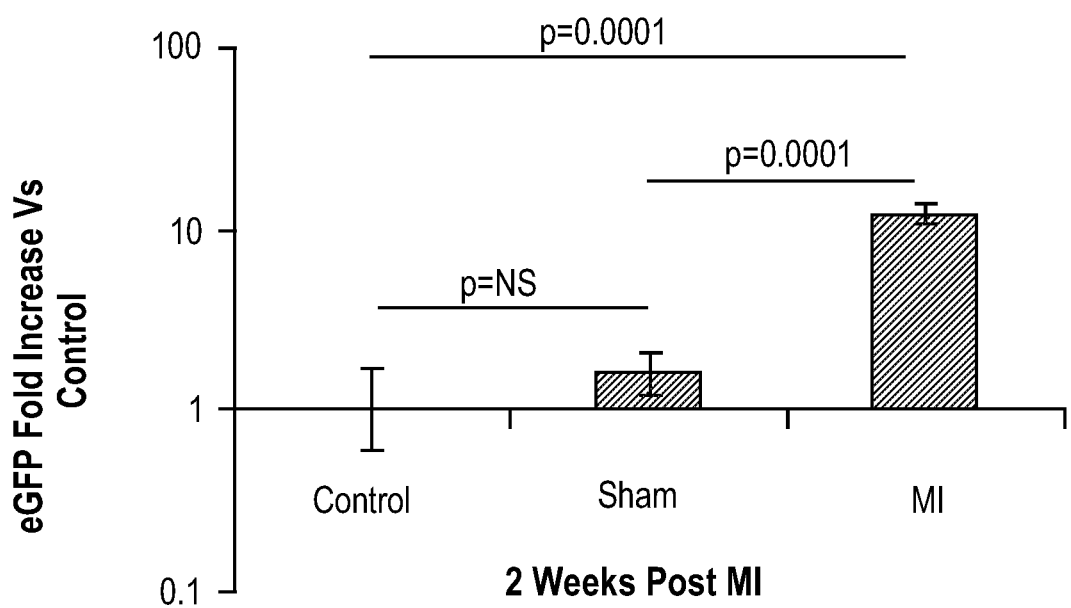

Initially, we quantified eGFP expression in injured maternal hearts relative to sham-operated pregnant mice and controls in which no injury was induced. Post-partum females were sacrificed at 1 or 2 weeks post-MI. Total DNA was extracted from each total heart and eGFP expression analyzed according to the methods described by Pfaffl, 2001 (FIG. 1B). Experimental infarcted hearts harvested at 1 week post-MI contained 120 times more eGFP than controls (p=0.0003) and 20 times more eGFP than shams (p=0.0027; FIG. 1C). Experimental infarcted hearts harvested at 2 weeks post-MI contained 12 times more eGFP than controls (p=0.0001) and 8 times more eGFP than shams (p=0.0001) (FIG. 1D). The absolute numbers of eGFP cells in control, sham-operated, and MI hearts were also computed based on qPCR (FIG. 8) and 1.7% of the total heart at 2 weeks post injury was composed of eGFP cells.

Example 2: Fetal Cells Adopt Diverse Cardiac Lineages In Vivo

In a separate group of infarcted and control mice, immunofluorescence analysis with confocal microscopy was utilized to detect eGFP+ cells in ventricular tissue sections of maternal hearts at various time points subsequent to myocardial injury (FIG. 1B and data not shown). EGFP+ cells were noted in infarct zones and peri-infarct zones of infarcted maternal hearts at 1, 2, 3, or 4 weeks post-MI (data not shown and Table 1A). Negligible numbers of eGFP cells were noted in non-infarct zones of the infarcted maternal hearts (Table 1B).

We further sought to determine whether the eGFP+ cells were differentiating into more mature cardiac cells as we noted a decrease in nuclear to cytoplasmic ratio with an increase in post-injury time (data not shown). Briefly, ventricular sections from maternal hearts analyzed at 1, 2, 3, and 4 weeks post-injury illustrated eGFP+ cells engrafting within infarct and peri-infarct zones. Fetal cells were positive for eGFP, nuclei were stained with DAPI, and light green background fluorescence was noted in maternal cardiomyocytes.

At 3 and 4 weeks post-MI, eGFP+ cells observed in the infarct zones of maternal hearts also expressed markers of cardiomyocytes (α-sarcomeric actin and α-actinin), smooth muscle cells (α-smooth muscle actin), and endothelial cells (CD31 and VE-cadherin) (data not shown). At 3 weeks post-MI, 50% of all eGFP-positive nuclei belonged to cells that also stained positive for -actinin, implying that 50% of eGFP cells homing to the heart may have differentiated to cardiomyocytes (Table 1C). These results suggest that fetal cells differentiated into diverse lineages within maternal cardiac tissue.

Table 1: cell quantification in ventricular tissue sections obtained from WT female mice mated with GFP transgenic mice, subjected to cardiac injury at mid-gestation, then sacrificed 3 weeks post-injury. 10 different sections in infarct zones and 10 different sections in non-infarct zones that comprised an area of 25 sq. mm each were utilized for this analysis. All nuclei (detected by DAPI staining) were counted in each section. All eGFP+ nuclei were also counted and the ratios are presented in Table 1A. This was repeated in non-infarct zones and the ratios are presented in Table 1B. Alpha-actinin stained cells were counted in the infarct zones (mononuclear) and the ratio of eGFP+ nuclei that were present in alpha-actinin stained cells is presented in Table 1C.

| A | | | |
|---|---|---|---|
| | Total nuclei infarct zone | eGFP+ nuclei | % eGFP+/ total nuclei |
| 1 | 64 | 6 | 9.3 |
| 2 | 81 | 3 | 3.7 |
| 3 | 112 | 3 | 2.7 |

-continued

| | | | |
|---|---|---|---|
| 4 | 123 | 2 | 1.6 |
| 5 | 81 | 3 | 3.7 |
| 6 | 105 | 4 | 3.8 |
| 7 | 127 | 1 | 0.8 |
| 8 | 71 | 1 | 1.4 |
| 9 | 85 | 1 | 1.2 |
| 10 | 79 | 2 | 2.5 |

B

| | Total nuclei Non-infarct zone | eGFP+ nuclei Non-Infarct Zone | % eGFP+ nuclei Non-Infarct Zone |
|---|---|---|---|
| 1 | 72 | 1 | 1.4 |
| 2 | 93 | 0 | 0 |
| 3 | 84 | 0 | 0 |
| 4 | 101 | 0 | 0 |
| 5 | 147 | 0 | 0 |
| 6 | 62 | 1 | 1.6 |
| 7 | 55 | 0 | 0 |
| 8 | 80 | 0 | 0 |
| 9 | 81 | 0 | 0 |
| 10 | 64 | 0 | 0 |
| Avg | 83.9 | 0.2 | 0.2 |

C

| | Total eGFP+ nuclei | eGFP+ Actinin+ nuclei | % eGFP+ Actinin+/ eGFP nuclei |
|---|---|---|---|
| 1 | 6 | 4 | 66.7 |
| 2 | 3 | 1 | 33.3 |
| 3 | 3 | 2 | 66.7 |
| 4 | 2 | 1 | 50 |
| 5 | 3 | 1 | 33.3 |
| 6 | 4 | 2 | 50 |
| 7 | 1 | 0 | 0 |
| 8 | 1 | 0 | 0 |
| 9 | 1 | 0 | 0 |
| 10 | 2 | 2 | 100 |
| Avg | 2.6 | 1.3 | 50 |

Figure 2:
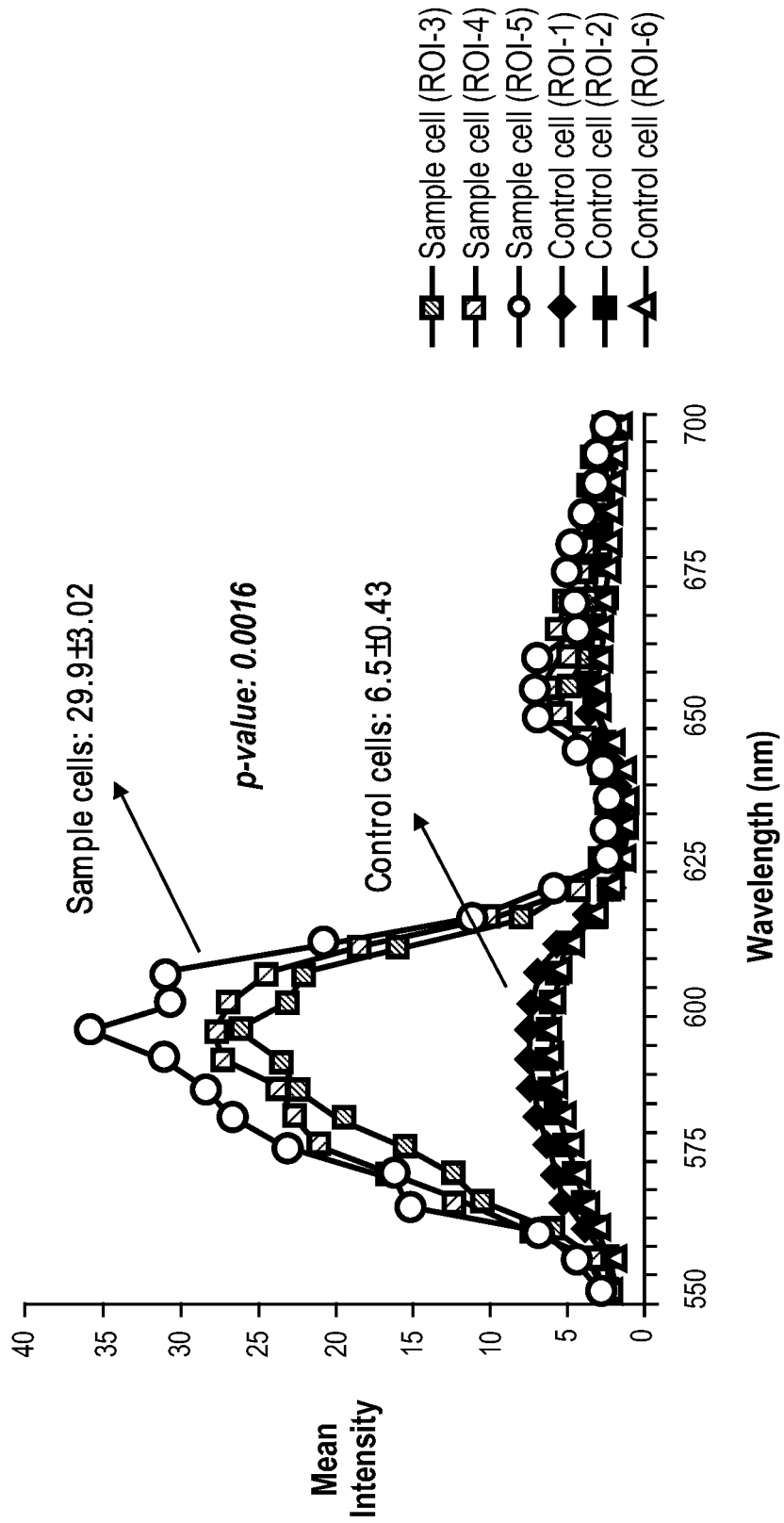
FIG. 2. Fetal cells differentiate into diverse cardiac lineages after homing to maternal heart. Mean intensities of the spectral profiles from ROIs 1-6 where ROIs 1, 2, and 6 are control areas and ROIs 3, 4, and 5 represent eGFP+ cells.

Spectral profiles were obtained from paraffin embedded ventricular tissue sections of infarcted maternal hearts. This measure was taken, in addition to the use of Sudan Black, to ensure that native autofluorescence of cardiomyocytes was not affecting fluorescence images (data not shown). In vivo analysis demonstrated that fetal cells (eGFP+) differentiated into cardiomyocytes expressing α-sarcomeric actin (α-sarc) and α-actinin, smooth muscle cells expressed α-smooth muscle actin (α-SMA) and endothelial cells expressed CD31 and VE-Cadherin (VE-cad). Paraffin embedded ventricular sections were obtained from infarcted hearts of pregnant mice 1 week after injury; stained with rabbit anti-GFP primary antibody and donkey anti-rabbit Alexa Fluor 568 secondary antibody (data not shown). Regions that represent regions of interest (ROIs) 1-6 were circled and subjected to spectral scanning. The mean intensities of the spectral scans for this section are plotted versus wavelength in FIG. 2. The mean intensities of the sample regions are significantly higher than the mean intensities of the control regions.

Example 3: Fetal Cells Isolated from Injured Maternal Hearts Differentiate to Endothelial Cells, Smooth Muscle Cells, and Spontaneously Beating Cardiomyocytes In Vitro We next used fluorescence activated cell sorting (FACS) to isolate fetal eGFP+ cells that had homed to maternal hearts and analyzed their in vitro behavior. When plated on CMFs, we noted clonal expansion of the fetal cells, their differentiation into smooth muscle cells and endothelial cells, and the formation of vascular structures (data not shown). Other cellular phenotypes, some of which have the appearance of neuronal cells, were also observed in these in vitro experiments with CMFs (data not shown).

Briefly, in vitro analysis of fetal cells isolated from maternal hearts demonstrated clonal expansion on CMFs. 14 days after plating, vascular tube formation was noted in a 3-dimensional collagen matrix. Fetal cells isolated from maternal hearts and plated on CMFs underwent differentiation into smooth muscle cells (α-SMA) and endothelial cells (CD31). Vascular tube formation was noted from fetal cells isolated from maternal hearts and plated on CMFs with expression of α-SMA and CD31. Fetal cells isolated from maternal hearts and plated on Cyclin A2 neonatal cardiomyocytes differentiated into beating cardiomyocytes. Cardiomyocytes arising from fetal cells isolated from maternal hearts expressed cardiac troponin T (cTnT) and connexin 43 (Cx43).

As we did not observe differentiation of fetal cells into cardiomyocytes on CMFs, we utilized cardiomyocytes isolated from neonatal cyclin A2 transgenic mice (Cheng et al., 2007) as feeders. When plated on these feeders with standard medium consisting of DMEM supplemented with FBS, the isolated eGFP+ fetal cells differentiated into spontaneously beating cardiomyocytes (about 48 beats/minute, data not shown). The resulting lineages also expressed cardiac troponin T (data not shown). Further analysis of eGFP+ fetal cells cultured for 5 weeks in chamber slides indicated expression of the gap junction marker connexin 43 (data not shown). This provides compelling evidence for formation of electromechanical connections between the cardiomyocytes derived from eGFP+ fetal cells and the feeder cardiomyocytes.

Figure 3A:
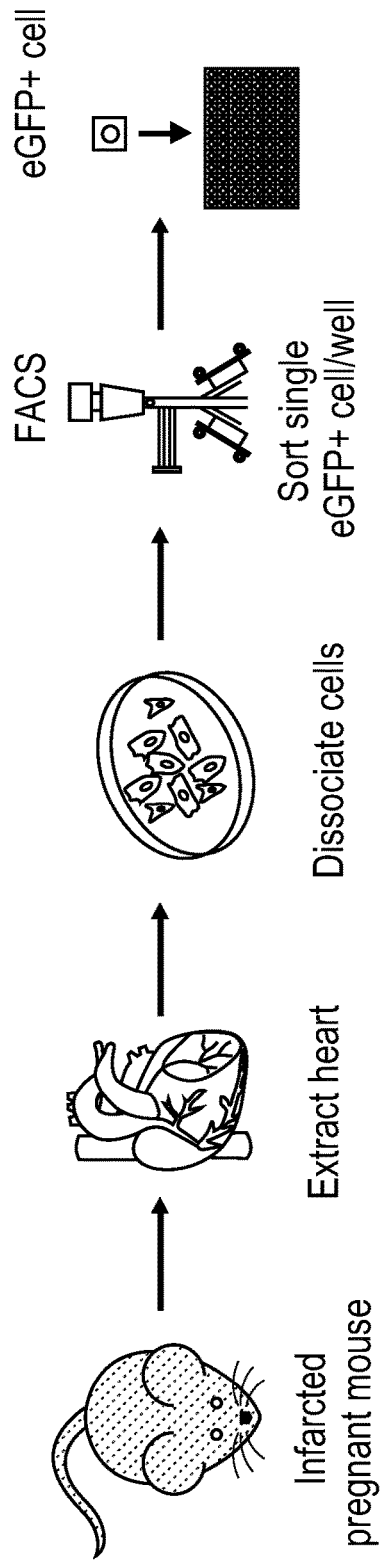
FIGS. 3A-B. Fetal cells exhibit clonality and undergo cardiac differentiation in a fusion-independent manner.
Figure 3B:
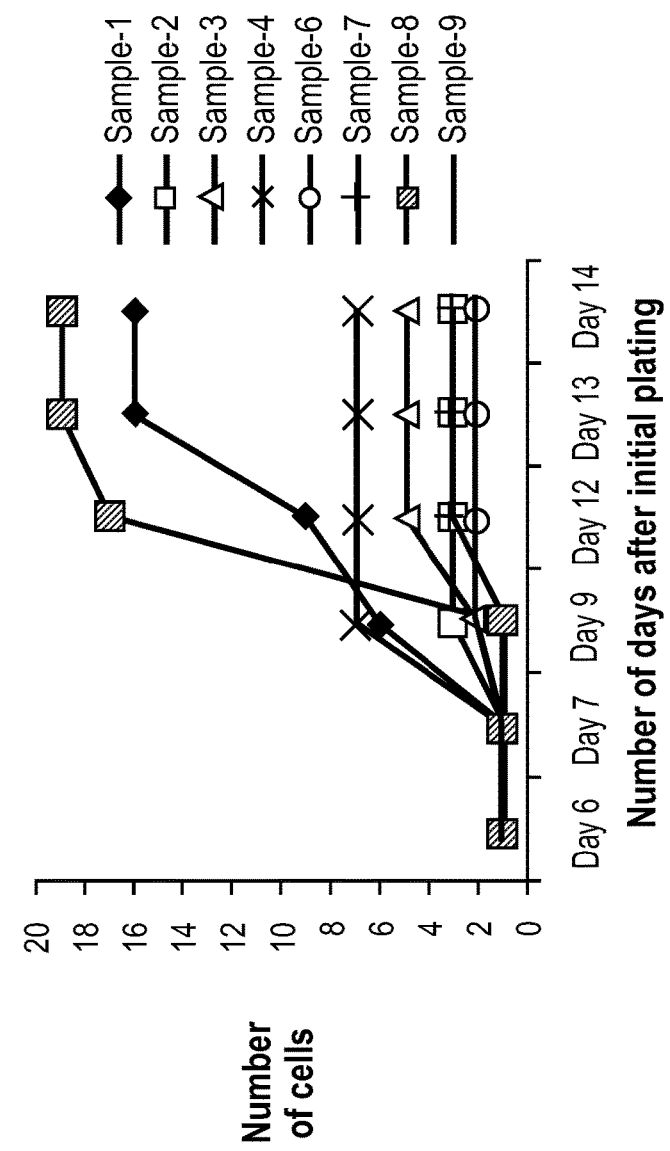

Example 4: Fetal Cells Exhibit Clonality and Undergo Cardiac Differentiation in a Fusion-Independent Manner Clonal analysis was performed to confirm the 'sternness' of the fetal cells giving rise to cardiac cells (FIG. 3A). FACS for eGFP+ cells was performed and single cells were seeded in 96-well plates containing WT neonatal cardiomyocytes as feeders. Clones derived from eGFP+ fetal cells were expanded for 14 days and total clones counted in each colony. Two 96-well plates were utilized and 4 wells in each plate gave rise to colonies after 7 days (approximately 50% of the wells in each plate contained viable cells at this time point) yielding an approximate cloning efficiency of 8.3%. The number of cells identified on days 6, 7, 9, 12, 13 and 14 is provided in FIG. 3B.

In order to mechanistically assess whether fusion, rather than differentiation, was the cause of the appearance of eGFP+ cardiomyocytes in our in vitro assays, we analyzed the number of nuclei present within our fetal cell-derived cardiomyocytes and consistently noted that these cardiomyocytes were mononuclear (data now shown). Where only GFP and DAPI staining was seen, still pictures were taken depicting the beating of these cells (data not shown). Cardiomyocytes derived in vitro from fetal cells isolated from maternal heart were found to be mononuclear.

Furthermore, fluorescence in situ hybridization (FISH) for X- and Y-chromosomes revealed one set of sex chromosomes within the eGFP+ cardiomyocyte nuclei, establishing the diploid nature of these nuclei and effectively ruling out fusion between eGFP+ fetal cells and feeder cardiomyocytes as the source of eGFP+ cardiomyocytes (data not shown).

Briefly, fetal cell-derived cardiomyocytes had diploid nuclei with one set of sex chromosomes detected per cell. eGFP+ cells (488 nm) that differentiated into cardiomyocytes as determined with cTNT staining (568 nm) were observed. The same cells were observed with different red and green wavelength filters to detect the X chromosome (520 nm) and the Y chromosome (550 nm). A tetraploid nucleus was observed in a non-eGFP cell. Only the nuclei of the cells and as the X, Y probes exhibited fluorescence at different wavelengths (FITC: 520 nm, Cy3: 550 nm) and their signals could be easily distinguished from the green fluorescence of the GFP (Alexa 488: 488 nm) and the secondary antibody to cardiac troponin T (Texas Red: 568 nm). The ability to detect tetraploid nuclei with this assay was demonstrated by identifying cells that were found in a region where GFP cells were not detected.

Figure 4A:
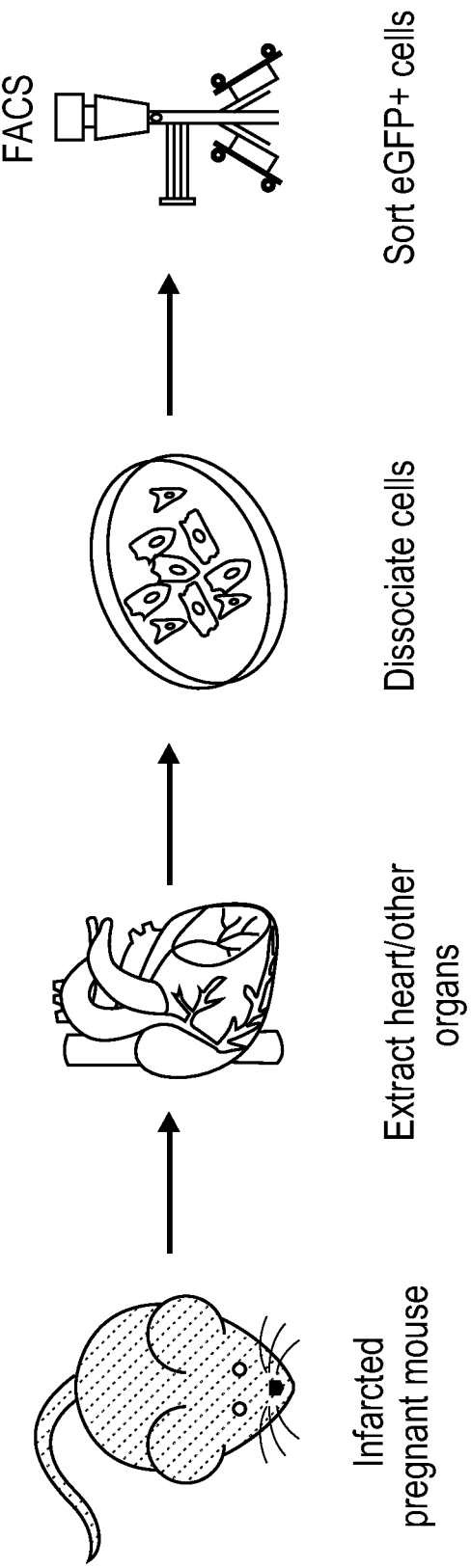
FIGS. 4A-C. Fetal cells selectively home to injured maternal hearts and not to non-injured organs; fetal cells express various stem cell markers, including Cdx2.

Example 5: Fetal Cells Selectively Home to the Injured Maternal Heart and Not to Non-Injured Organs To assess whether eGFP+ cells from the fetus were homing selectively to the injured heart, we utilized FACS to sort eGFP+ cells from a variety of organs and tissues harvested from pregnant mice subjected to cardiac injury. These organs and tissues were minced and triturated to generate cell suspensions (FIG. 4A). Corresponding cell populations were obtained from age-matched pregnant WT female mice mated with WT males and used as controls to establish the appropriate FACS gates to select eGFP+ cells. Cells were isolated from the injured heart, blood, skeletal muscle, chest wall, eGFP-littermates, liver, lung, and placenta.

Figure 4B:
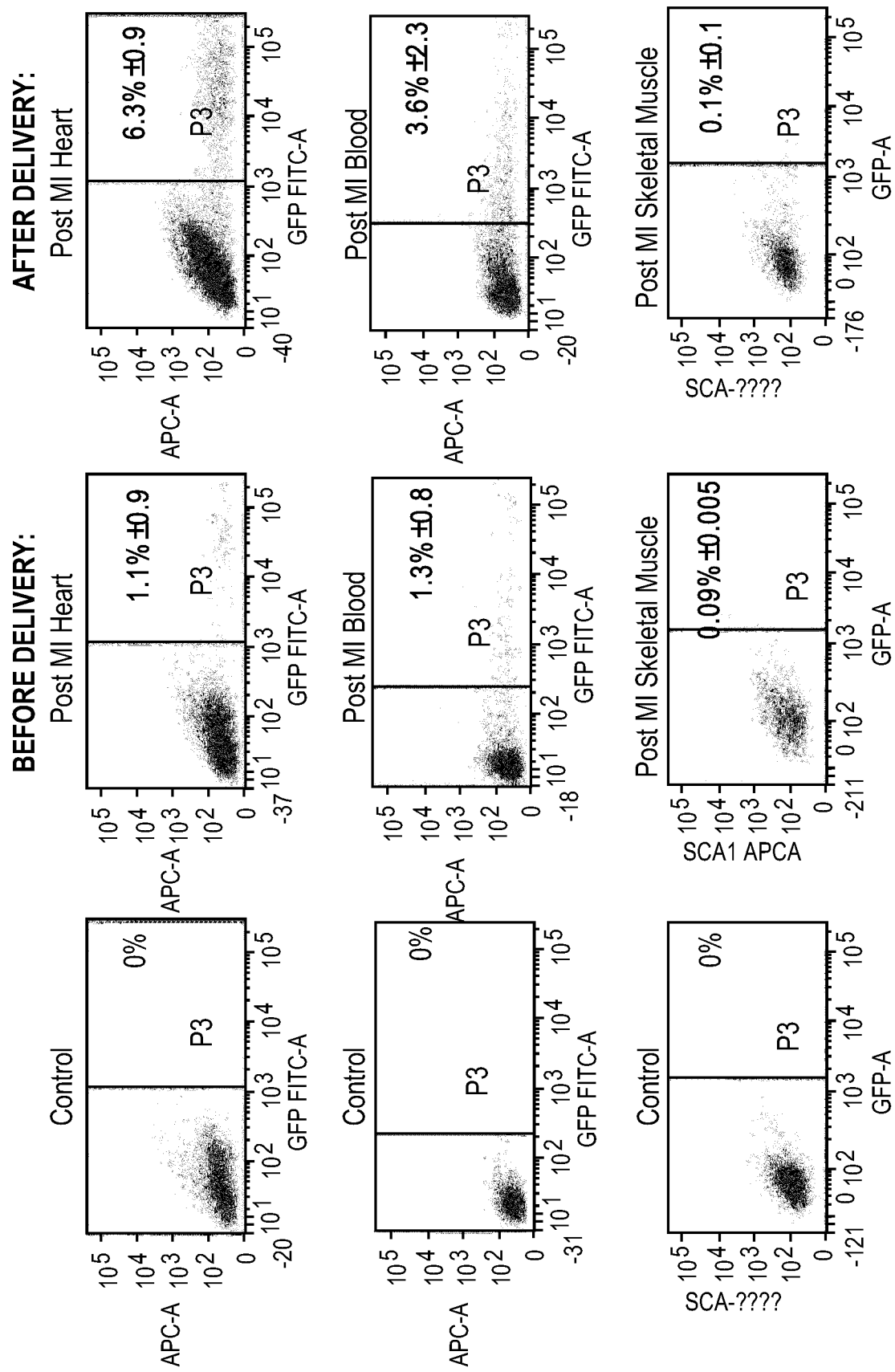
Figure 4B:
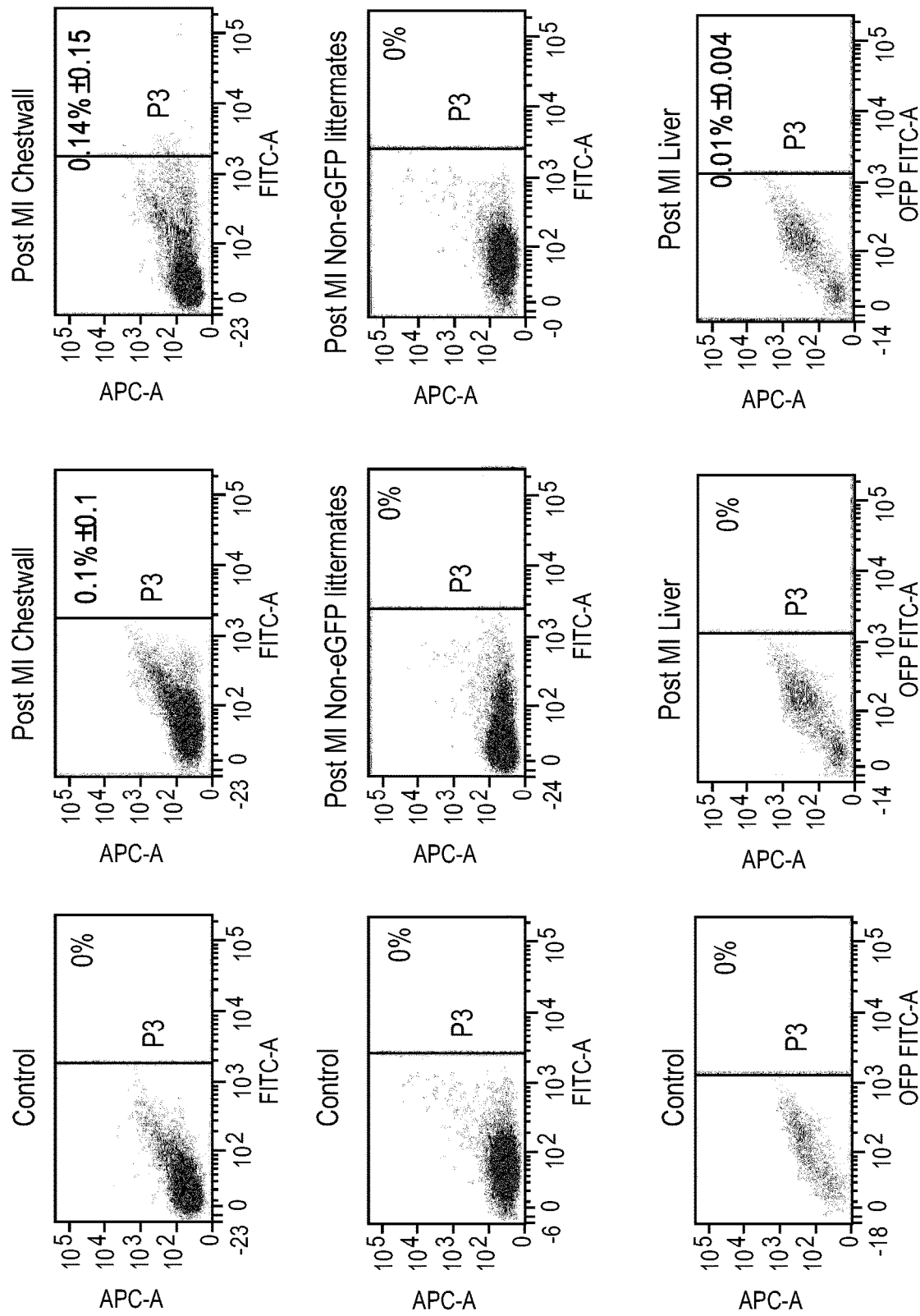
Figure 4B:
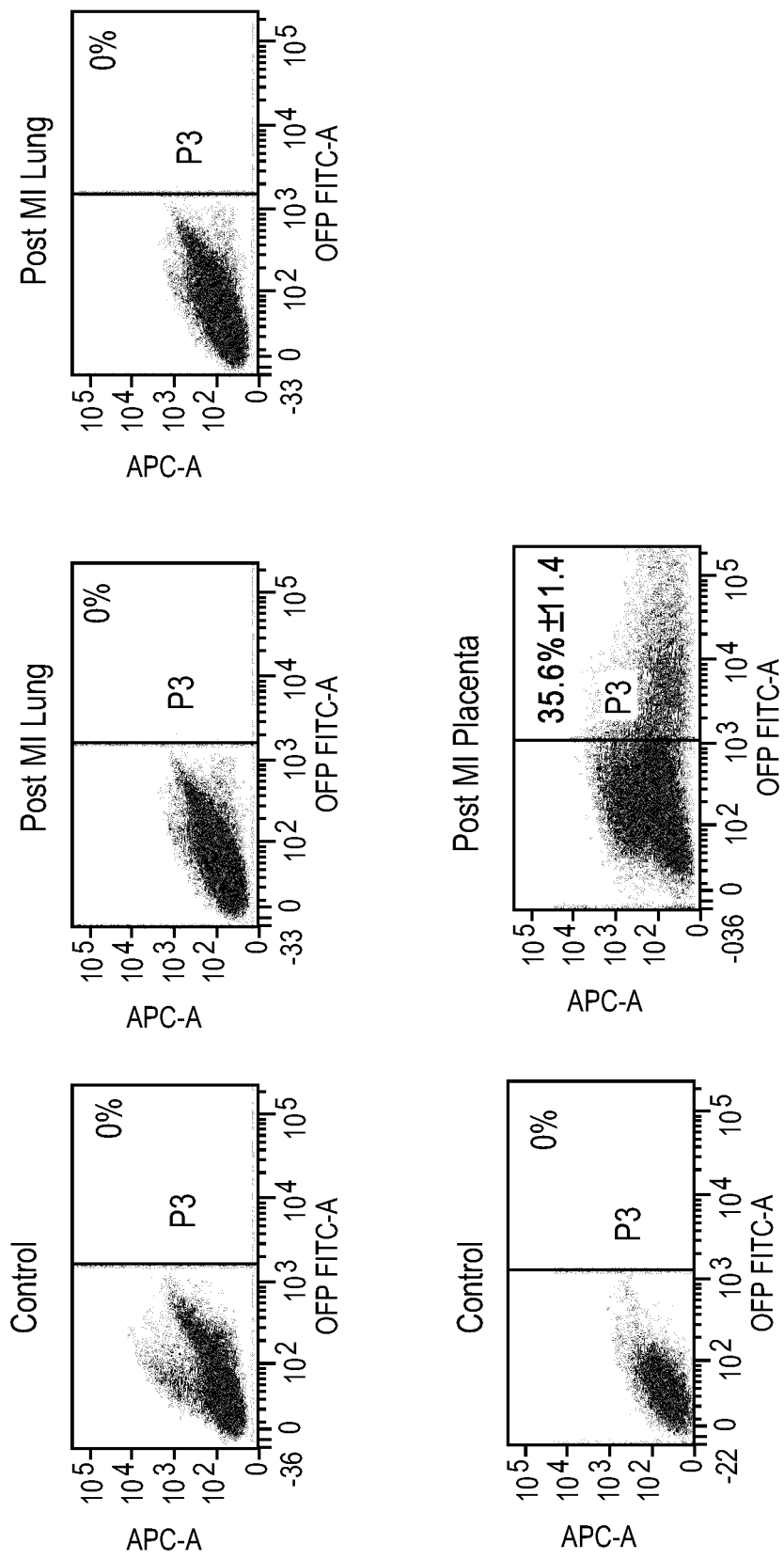

FACS to select eGFP+ cells was performed at two time points, 4.5 days post-injury (prior to delivery) and 7 days post-injury (after delivery) for all of these tissues except placenta (analyzed before delivery only) as it is resorbed by the mother in mice at time of delivery (FIG. 4B). The low quantity of eGFP+ cells in all tissues, including injured heart, prior to 4.5 days post injury precluded any detailed phenotypic analyses. Therefore, it appears that mobilization of fetal cells in response to maternal injury takes approximately 4.5 days. In the injured heart, ~1.1% of the cells were eGFP+ prior to delivery and this number rose significantly to ~6.3% just after delivery. In blood, ~1.3% of cells were eGFP+ before delivery and this number rose to ~3.6% after delivery, although this increase was not statistically significant.

Figure 4C:
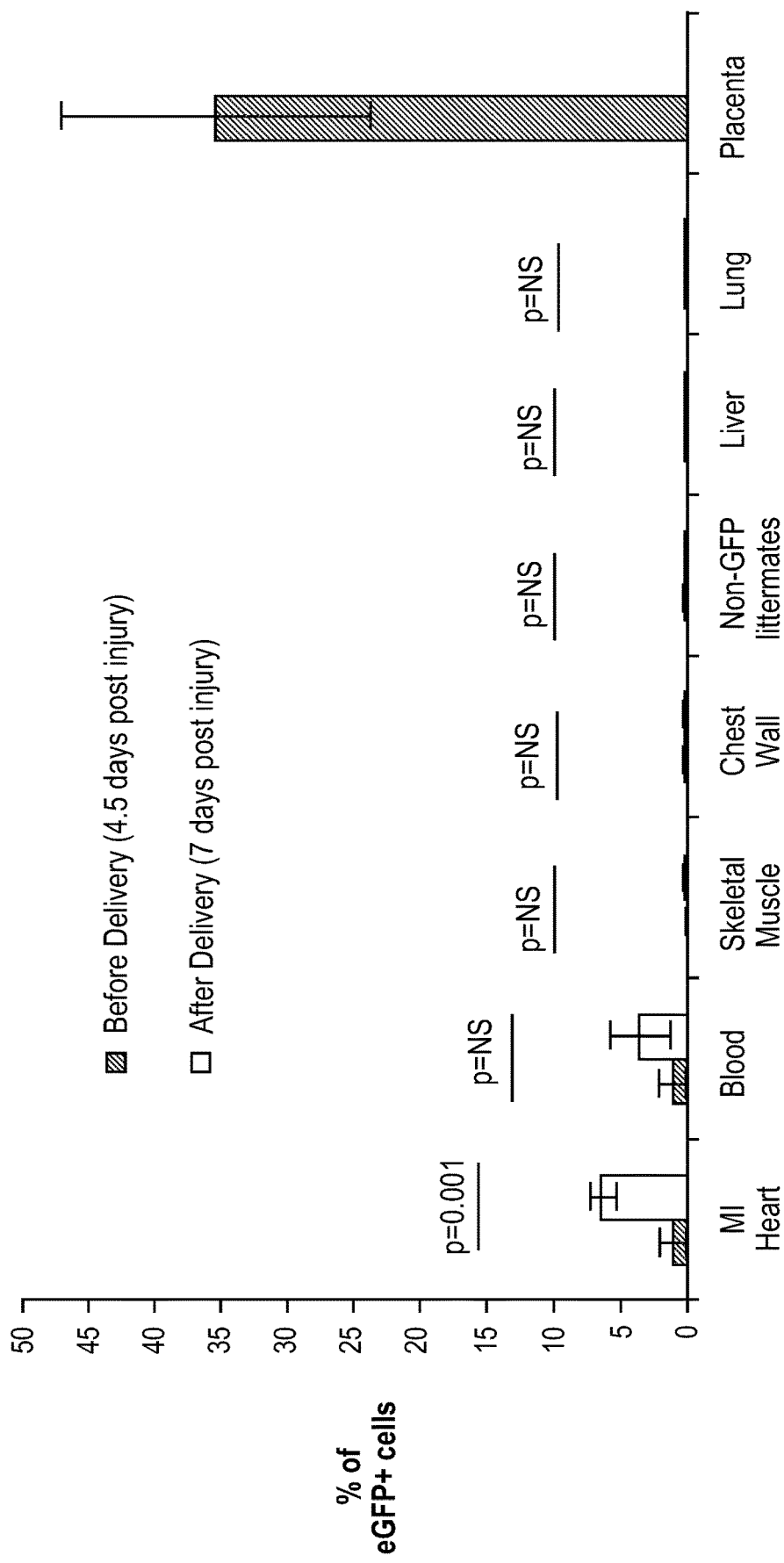

Delivery therefore seems to cause the numbers of fetal cells entering the maternal circulation to rise, and this corresponds with a significant increase in fetal cells homing to the injured heart. There were negligible numbers of eGFP+ cells noted in skeletal muscle before and after delivery. The chest wall, where a lesser degree of injury was induced as an incision had to be performed to induce cardiac injury, exhibited a relatively smaller percentage of fetal cells compared with heart and blood. There was no increase in the number of fetal cells homing to the chest wall after delivery, likely due to healing in the seven days post-injury. EGFP-littermates were also examined for the presence of eGFP+ cells. Although a few cells were noted prior to delivery likely due to the shared circulation with the eGFP+ littermates, eGFP cells were not detected in these littermates after delivery. Liver and lung exhibited negligible numbers of fetal cells. As expected, placenta exhibited the largest percentage of eGFP cells with approximately 36% of placenta cells expressing eGFP. Overall, the results provide clear evidence for the selective and specific homing of eGFP+ fetal cells to the injured heart of the mother, and not to other non-injured maternal tissues (FIG. 4B and FIG. 4C).

Example 6: Fetal Cells Isolated from Maternal Hearts Express a Variety of Progenitor Markers, Most Notably Cdx2

To establish the identity of the cell type(s) involved in fetal maternal transfer, we analyzed FACS-sorted, eGFP+ cells isolated from maternal hearts 1 week post-injury for stem/progenitor cell markers (FIG. 5A). 80% of these cells expressed Nkx2. (Komuro and Izumo, 1993; Lints et al., 1993; Ueyama et al., 2003) implying that cardiomyogenic differentiation had begun as soon as these cells entered the injured maternal heart. Consistent with this, very small numbers, <1%, of placental cells from pregnant mice expressed Nkx2.5 (FIG. 9). Additionally, 46% of cells homing to the maternal heart expressed CD31, which was not surprising given the degree of fetal cell-mediated vasculogenesis we observed in injured maternal hearts. The marker Cdx2 was found in 38% of fetal cells.

Cdx2 regulates trophoblast stem (TS) cell development and proliferation (Niwa et al., 2005; Strumpf et al., 2005), but the present inventors identified for the first time that Cdx2 is associated with cardiomyogenic differentiation. This finding raises the possibility that, in the setting of acute injury, TS cells from placenta can give rise to various cardiac lineages in addition to forming placenta. Fetal cells isolated from maternal hearts also displayed lower levels of several markers of endogenous cardiac progenitors, namely Sca-1 28, 29 (21%), cKit (25%) and Islet1 (3%), as well as embryonic stem (ES) cell markers Pou5f1 (2%), Nanog (3%) and Sox2 (24%). The higher expression of Sox2 is consistent with its expression in non-ES cells as well. Finally, hematopoietic stem cell factor CD34 was expressed in 15% of the eGFP+ cells which is consistent with placenta acting as a rich source of hematopoietic stem cells (FIG. 5A).

As the eGFP+ cells were traversing through or derived from the placenta, we analyzed gene expression of known 'sternness' factors in eGFP+ cells. We sorted eGFP+ cells from end-gestation placentas from three different pregnant mice that had been subjected to myocardial injury. RNA expression of 92 known pluripotency genes was analyzed (Table 2), and gene expression relative to GAPDH expression for the most prevalent transcripts is plotted in FIG. 5B. These mRNA array studies confirmed the presence of Cdx2 and Eomesodermin (Eomes), another marker of TS cells, in the eGFP+ placenta cells.

Example 7: Discussion

Figure 6:
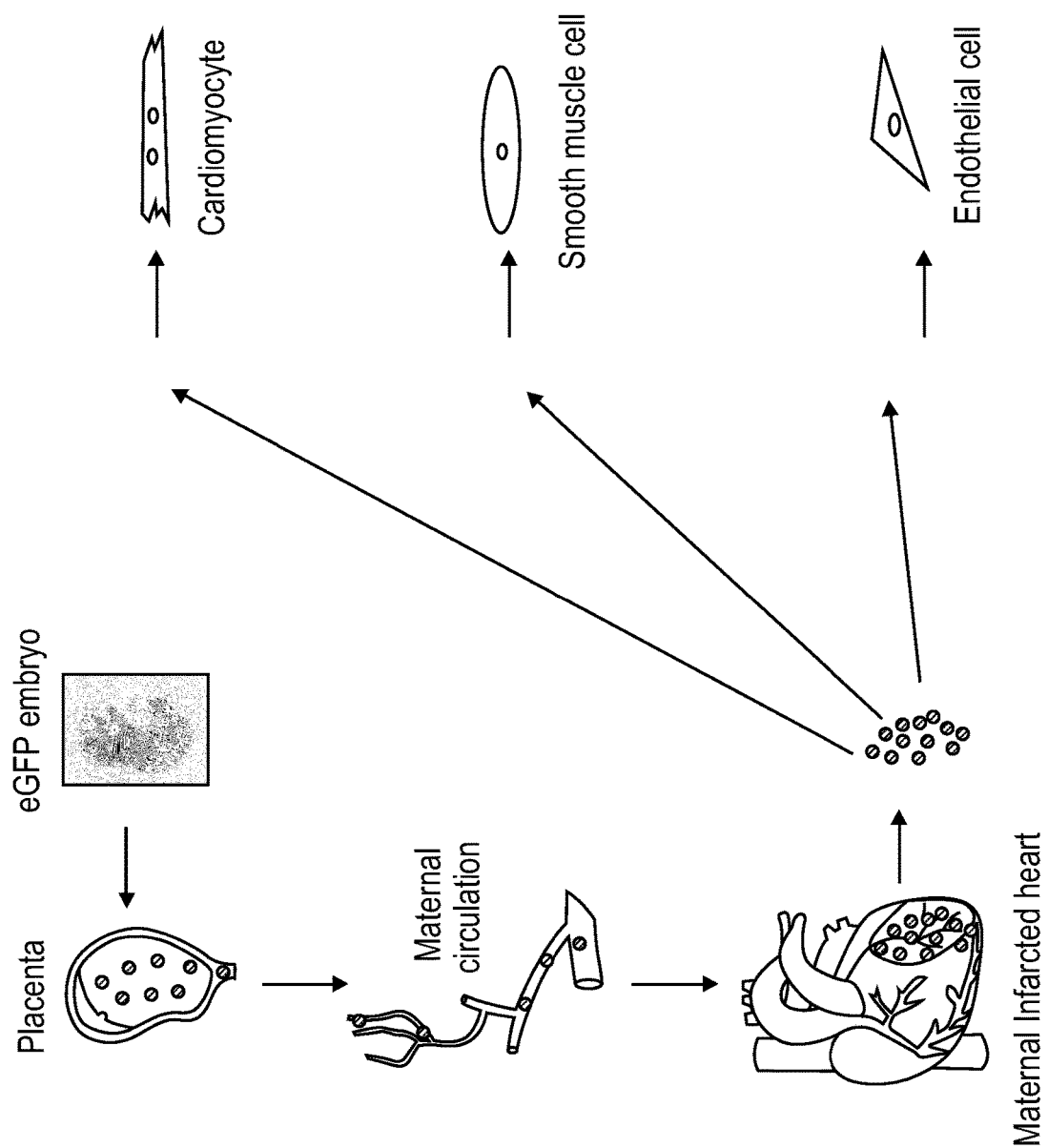
FIG. 6. Model depicting trafficking of cells from fetus across placenta into maternal circulation to injury and peri-injury zones of the maternal heart. Cells of fetal origin engraft within maternal heart and give rise to diverse cardiac lineages including cardiomyocytes, smooth muscle cells and endothelial cells.
Figure 7:
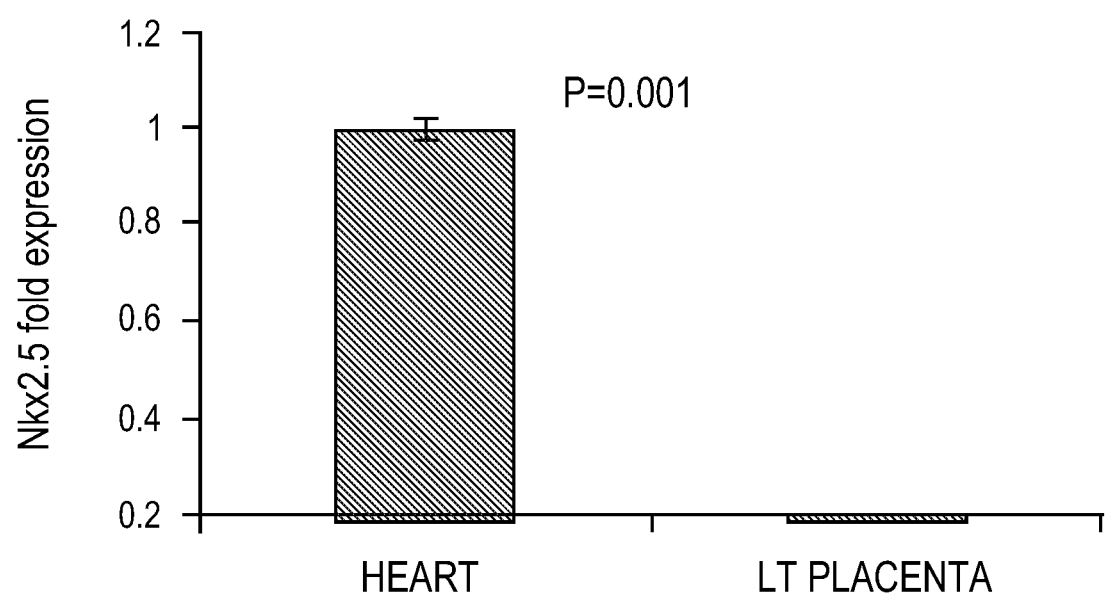
FIG. 7. Negligible Nkx2.5 expression was observed in late term placenta of mouse with cardiac injury relative to positive control (E16.5 heart). Nkx2.5 expression by q-PCR above was plotted relative to Nkx2.5 expression in E16.5 heart.

The selective homing of eGFP+ cells in our model to the site of maternal cardiac injury with lack of such homing to non-injured tissues points to the presence of precise signals sensed by cells of fetal origin that target them to diseased myocardium specifically, and to differentiate into diverse cardiac lineages (FIG. 6). Most notable is their differentiation into functional cardiomyocytes that are able to beat in syncytium with neighboring cardiomyocytes (data not shown), thus a fetus may assist in protecting the mother's heart during and after pregnancy. The present studies were inspired by the recovery noted in peripartum cardiomyopathy, whereby a remarkable 50% of women spontaneously recover from heart failure. Peripartum cardiomyopathy has the highest rate of recovery amongst all etiologies of heart failure It was this observation that prompted us to hypothesize that there may be a fetal or placental contribution to counteract maternal cardiac injury. The mouse injury model presented herein serves as a model system of murine feto-maternal microchimerism that can help identify appropriate cell types for cardiac regeneration.

To this end, a far greater spectrum of potential applications to the field of heart disease emerges from the present studies. The challenge of cardiovascular regenerative medicine is to develop novel therapeutic strategies to facilitate regeneration of normally functioning cardiomyocytes in the diseased heart. Utilizing live imaging, we have demonstrated that fetal cells differentiate into spontaneously beating cardiomyocytes after homing to the heart.

Our identification of Cdx2 as a unique and highly prevalent marker expressed on fetal cells in the maternal myocardium offers a new perspective regarding the appropriate cell type that may be used for therapeutic purposes. The Cdx family of transcription factors consist of three mouse homologues (Cdx 1, 2, and 4) of the *Drosophila* caudal homeobox genes, which are involved in specifying cell position along the anteroposterior axis, with similar functions in the later developmental stages of the mouse embryoas well as morphological specification of murine gut endoderm. Cdx2 is also involved in trophectoderm fate commitment in the developing blastocyst. The trophectoderm gives rise to the trophoblast stem cells which have previously been associated solely with differentiation to the placenta lineage.

Our results point towards the transfer of several populations of progenitor cells, and our finding of Cdx2 cells of fetal or placental origin in the heart indicates a new method of treating cardiac conditions with a Cdx2 cell type that is capable of cardiac differentiation under injury conditions that can be readily isolated from placenta.

TABLE 2

| Gene ID | Raw Ct Values | | | Values Normalized to | | |
|---|---|---|---|---|---|---|
| | Placenta1 | Placenta2 | Placenta3 | Placenta1 | Placenta2 | Placenta3 |
| 18S-Hs99999901_s1 | 6.3705 | 8.47053 | 16.0094 | | | |
| Gapdh-Mm99999915_g1 | 20.9696 | 18.8751 | 13.6232 | 0 | 0 | 0 |
| Hprt1-Mm00446968_m1 | 25.9639 | 23.6467 | 33.147 | 4.9943 | 4.7716 | 19.5238 |
| Gusb-Mm00446953_m1 | 26.4595 | 24.424 | 33.4364 | 5.4899 | 5.5489 | 19.8132 |
| Actc1-Mm01333821_m1 | 28.8881 | 25.4953 | 22.127 | 7.9185 | 6.6202 | 8.5038 |
| Afp-Mm00431715_m1 | 20.0476 | 18.6008 | 12.1797 | −0.922 | −0.2743 | −1.4435 |
| Bxdc2-Mm00503229_m1 | 27.1527 | 24.3709 | 20.021 | 6.1831 | 5.4958 | 6.3978 |
| Cd34-Mm00519283_m1 | 26.2739 | 23.7997 | 18.4277 | 5.3043 | 4.9246 | 4.8045 |
| Cd9-Mm00514275_g1 | 24.2361 | 21.3352 | 17.3176 | 3.2665 | 2.4601 | 3.6944 |
| Cdh5-Mm00486938_m1 | 23.3841 | 20.926 | 15.4999 | 2.4145 | 2.0509 | 1.8767 |
| Cdx2-Mm00432449_m1 | 27.8661 | 27.2999 | 21.1473 | 6.8965 | 8.4248 | 7.5241 |
| Col1a1-Mm00801666_g1 | 20.7192 | 18.2277 | 13.2472 | −0.2504 | −0.6474 | −0.376 |
| Col2a1-Mm00491889_m1 | 26.1934 | 27.0833 | 19.0532 | 5.2238 | 8.2082 | 5.43 |
| Commd3-Mm00521684_m1 | 30.2898 | 27.3424 | 24.3104 | 9.3202 | 8.4673 | 10.6872 |
| Crabp2-Mm00801693_g1 | 29.5281 | 27.8679 | 22.113 | 8.5585 | 8.9928 | 8.4898 |
| Ddx4-Mm00802445_m1 | 33.419 | 31.4264 | 27.0787 | 12.4494 | 12.5513 | 13.4555 |
| Des-Mm00802455_m1 | 27.1446 | 26.0115 | 20.7865 | 6.175 | 7.1364 | 7.1633 |
| Dnmt3b-Mm01240113_m1 | 29.001 | 27.4062 | 22.5412 | 8.0314 | 8.5311 | 8.918 |
| Lefty1-Mm00438615_m1 | UD | 36.3593 | 31.8521 | UD | 17.4842 | 18.2289 |
| Eomes-Mm01351985_m1 | 34.1758 | 32.7162 | 27.0058 | 13.2062 | 13.8411 | 13.3826 |
| Fgf4-Mm00438917_m1 | UD | UD | UD | UD | UD | UD |
| Fgf5-Mm00438919_m1 | 35.3186 | 36 | 30.7142 | 14.349 | 17.1249 | 17.091 |
| Flt1-Mm00438980_m1 | 26.067 | 24.1073 | 19.1198 | 5.0974 | 5.2322 | 5.4966 |
| Fn1-Mm01256744_m1 | 21.7467 | 19.7424 | 14.3723 | 0.7771 | 0.8673 | 0.7491 |
| Foxa2-Mm01976556_s1 | 28.0793 | 25.4683 | 25.0441 | 7.1097 | 6.5932 | 11.4209 |
| Foxd3-Mm02384867_s1 | UD | 30.8118 | UD | UD | 11.9367 | UD |
| Gabrb3-Mm00433473_m1 | 35.8833 | 32.5907 | 28.297 | 14.9137 | 13.7156 | 14.6738 |
| Gal-Mm00439056_m1 | 33.0773 | 29.2917 | 24.8623 | 12.1077 | 10.4166 | 11.2391 |
| Gata4-Mm00484689_m1 | 26.0794 | 25.4503 | 19.0996 | 5.1098 | 6.5752 | 5.4764 |
| Gata6-Mm00802636_m1 | 26.988 | 24.3801 | 19.2929 | 6.0184 | 5.505 | 5.6697 |
| Gbx2-Mm00494578_m1 | UD | 31.4816 | 27.8815 | UD | 12.6065 | 14.2583 |
| Gcg-Mm00801712_m1 | UD | 38.1937 | 33.0883 | UD | 19.3186 | 19.4651 |
| Gcm1-Mm00492310_m1 | 31.5349 | 31.052 | 23.4502 | 10.5653 | 12.1769 | 9.827 |
| Gdf3-Mm00433563_m1 | 36.7057 | 34.4247 | 29.3908 | 15.7361 | 15.5496 | 15.7676 |
| Gfap-Mm00546086_m1 | 36.3519 | 35.458 | 28.0648 | 15.3823 | 16.5829 | 14.4416 |
| Grb7-Mm01306734_m1 | 28.2935 | 26.5652 | 21.7775 | 7.3239 | 7.6901 | 8.1543 |
| Hbb-b2-Mm00731743_mH | 20.7765 | 20.2892 | 13.2353 | −0.1931 | 1.4141 | −0.3879 |
| Hba-x-Mm00439255_m1 | 23.6843 | 25.7335 | 16.204 | 2.7147 | 6.8584 | 2.5808 |
| Mnx1-Mm00658300_g1 | 37.833 | 33.6542 | 29.1002 | 16.8634 | 14.7791 | 15.477 |
| Iapp-Mm00439403_m1 | UD | UD | 34.065 | UD | UD | 20.4418 |
| Ifitm1-Mm00850040_g1 | 26.5783 | 23.0079 | 21.176 | 5.6087 | 4.1328 | 7.5528 |
| Ifitm2-Mm00850080_g1 | 27.9784 | 24.3113 | 24.372 | 7.0088 | 5.4362 | 10.7488 |
| Il6st-Mm00439668_m1 | 26.2689 | 24.1603 | 19.5894 | 5.2993 | 5.2852 | 5.9662 |
| Igfbp2-Mm00492632_m1 | 26.9526 | 25.3066 | 20.1445 | 5.983 | 6.4315 | 6.5213 |
| Ins2-Mm00731595_gH | UD | 30.2597 | 28.4544 | UD | 11.3846 | 14.8312 |
| Pdx1-Mm00435565_m1 | UD | 35.5069 | 31.2635 | UD | 16.6318 | 17.6403 |
| Isl1-Mm00627860_m1 | 38.4946 | 33.7686 | 28.5575 | 17.525 | 14.8935 | 14.9343 |
| Kit-Mm00445212_m1 | 26.2121 | 25.2267 | 19.107 | 5.2425 | 6.3516 | 5.4838 |
| Krt1-Mm00492992_g1 | 30.9432 | 33.8954 | 24.0382 | 9.9736 | 15.0203 | 10.415 |
| Lama1-Mm00439445_m1 | 23.3831 | 23.2048 | 15.6915 | 2.4135 | 4.3297 | 2.0683 |
| Lamb1-1-Mm00801853_m1 | 24.1153 | 21.8563 | 16.8898 | 3.1457 | 2.9812 | 3.2666 |
| Lamc1-Mm00711820_m1 | 23.7416 | 21.9146 | 16.7137 | 2.772 | 3.0395 | 3.0905 |
| Lefty2-Mm00774547_m1 | UD | 37.5112 | 30.8274 | UD | 18.6361 | 17.2042 |
| Lifr-Mm00442940_m1 | 24.8734 | 23.0875 | 17.5635 | 3.9038 | 4.2124 | 3.9403 |

TABLE 2-continued

| | Raw Ct Values | | | Values Normalized to | | |
|---|---|---|---|---|---|---|
| Gene ID | Placenta1 | Placenta2 | Placenta3 | Placenta1 | Placenta2 | Placenta3 |
| Lin28-Mm00524077_m1 | 30.6329 | 30.7133 | 23.7301 | 9.6633 | 11.8382 | 10.1069 |
| Myf5-Mm00435125_m1 | UD | UD | UD | UD | UD | UD |
| Myod1-Mm00440387_m1 | 36.7214 | 33.2402 | 33.0302 | 15.7518 | 14.3651 | 19.407 |
| Nanog-Mm02019550_s1 | 37.0344 | 26.5706 | 27.9819 | 16.0648 | 7.6955 | 14.3587 |
| Nes-Mm00450205_m1 | 28.063 | 27.425 | 21.2942 | 7.0934 | 8.5499 | 7.671 |
| Neurod1-Mm01946604_s1 | UD | 28.183 | 30.9275 | UD | 9.3079 | 17.3043 |
| Nodal-Mm00443040_m1 | 33.4446 | 32.016 | 26.1958 | 12.475 | 13.1409 | 12.5726 |
| Nog-Mm00476456_s1 | 27.4575 | 25.9114 | 20.7441 | 6.4879 | 7.0363 | 7.1209 |
| Nppa-Mm01255747_g1 | 35.4623 | 33.6554 | 29.1081 | 14.4927 | 14.7803 | 15.4849 |
| Nr5a2-Mm00446088_m1 | 34.1867 | 33.3681 | 27.3547 | 13.2171 | 14.493 | 13.7315 |
| Nr6a1-Mm00599848_m1 | 30.1965 | 28.0504 | 23.2667 | 9.2269 | 9.1753 | 9.6435 |
| Olig2-Mm01210556_m1 | 36.607 | 37.1301 | 29.3012 | 15.6374 | 18.255 | 15.678 |
| Pax4-Mm01159036_m1 | UD | UD | UD | UD | UD | UD |
| Pax6-Mm00443072_m1 | 36.5576 | 34.7341 | 30.4868 | 15.588 | 15.859 | 16.8636 |
| Pecam1-Mm00476702_m1 | 24.4944 | 22.4209 | 17.2251 | 3.5248 | 3.5458 | 3.6019 |
| Podxl-Mm00449829_m1 | 24.7904 | 24.0435 | 17.0374 | 3.8208 | 5.1684 | 3.4142 |
| Pou5f1-Mm00658129_gH | 35.2662 | 32.652 | 29.28 | 14.2966 | 13.7769 | 15.6568 |
| Pten-Mm00477210_m1 | 27.204 | 24.7365 | 20.3668 | 6.2344 | 5.8614 | 6.7436 |
| Ptf1a-Mm00479622_m1 | UD | UD | UD | UD | UD | UD |
| Rest-Mm00803268_m1 | 27.8035 | 25.3074 | 20.7451 | 6.8339 | 6.4323 | 7.1219 |
| Runx2-Mm00501578_m1 | UD | 36.1486 | 31.7123 | UD | 17.2735 | 18.0891 |
| Sema3a-Mm00436469_m1 | 32.1638 | 29.0252 | 25.3798 | 11.1942 | 10.1501 | 11.7566 |
| Serpina1a-Mm02748447_g1 | 31.0904 | 26.3099 | 25.5911 | 10.1208 | 7.4348 | 11.9679 |
| Sfrp2-Mm00485986_m1 | 29.387 | 26.3426 | 22.2145 | 8.4174 | 7.4675 | 8.5913 |
| Sox17-Mm00488363_m1 | 27.3797 | 27.152 | 20.0432 | 6.4101 | 8.2769 | 6.42 |
| Sox2-Mm00488369_s1 | UD | 27.3828 | 26.4852 | UD | 8.5077 | 12.862 |
| Sycp3-Mm00488519_m1 | 36.7673 | 32.6623 | 29.1498 | 15.7977 | 13.7872 | 15.5266 |
| Syp-Mm00436850_m1 | 33.0295 | 30.0902 | 24.2542 | 12.0599 | 11.2151 | 10.631 |
| T-Mm00436877_m1 | UD | UD | 39.9782 | UD | UD | 26.355 |
| Tat-Mm01244282_m1 | 35.7324 | 37.7088 | 30.4848 | 14.7628 | 17.8337 | 16.8616 |
| Tdgf1-Mm00783944_g1 | UD | 27.1602 | 28.2507 | UD | 8.2851 | 14.6275 |
| Tert-Mm00436931_m1 | 32.5026 | 30.957 | 26.0882 | 11.533 | 12.0819 | 12.465 |
| Tcfcp2l1-Mm00470119_m1 | 31.0598 | 30.9915 | 24.7141 | 10.0902 | 12.1164 | 11.0909 |
| Th-Mm00447546_m1 | UD | 37.1873 | 30.4919 | UD | 18.3122 | 16.8687 |
| Utf1-Mm00447703_g1 | 31.1389 | 28.538 | 25.2141 | 10.1693 | 9.6629 | 11.5909 |
| Wt1-Mm00460570_m1 | 31.4399 | 30.056 | 24.2453 | 10.4703 | 11.1809 | 10.6221 |
| Xist-Mm01232884_m1 | 27.0304 | 24.1311 | 19.2598 | 6.0608 | 5.256 | 5.6366 |
| Zfp42-Mm01194090_g1 | 29.3088 | 25.9252 | 23.1699 | 8.3392 | 7.0501 | 9.5467 |
| Eras-Mm01345955_s1 | UD | 28.1246 | 28.6338 | UD | 9.2495 | 15.0106 |
| Raf1-Mm00466513_m1 | 27.2131 | 25.4176 | 19.9228 | 6.2435 | 6.5425 | 6.2996 |
| Ctnnb1-Mm00483033_m1 | 23.5056 | 21.6847 | 15.913 | 2.536 | 2.8096 | 2.2898 |
| Eef1a1-Mm01966109_u1 | 19.9088 | 16.648 | 13.2675 | −1.0608 | −2.2271 | −0.3557 |

UD = Undetermined

The following example describes isolation of Cdx2 cells from end-gestation mouse and human placentas utilizing lentiviral vectors and testing their differentiation properties in vitro. A lentivirus was constructed in which the murine Cdx2 promoter drives expression of the reporter gene tdTomato. The control lentivirus employs a cytomegalovirus promoter driving tdTomato. Cell suspensions of placenta tissues are made and Cdx2 cells are sorted based on the red fluorescence of tdTomato. Single cell sorting into 96-well plates is performed to confirm clonality. These are then be cultured on cardiac mesenchymal fibroblasts and neonatal cardiomyocytes to test their ability to differentiate into endothelial cells, smooth muscle cells, and cardiomyocytes. Live-imaging microscopy is utilized to assess spontaneous beating of Cdx2 cell-derived cardiomyocytes.

The following example describes testing the ability of Cdx2 cells isolated from placenta to form cardiomyocytes and blood vessels in vivo via transplantation experiments in the post-myocardial infarction setting. We will first test Cdx2 cells' cardiovascular differentiation potential in vivo and their ability to restore cardiac function in a rodent model. Immunohistochemical approaches are utilized to detect formation of endothelial cells, smooth muscle cells, and cardiomyocytes in infarcted hearts. Cardiac function enhancement is detected with magnetic resonance imaging (MRI). If transplantation of Cdx2 cells into infarcted rodent hearts demonstrates evidence of cardiac regeneration with improvement in ejection fraction, a large animal study is to be performed in an art-recognized porcine infarct model. Porcine (pig) infarct models include those described by, for example, Hayase et al. (2005) Heart Cir. Physiol. 288: H2995-H3000. Briefly, hearts of living pigs are treated a cell population containing Cdx2 cells by injection into one or more sites surrounding an infarction. Alternatively, hearts of living pigs are injected with a vector (e.g., a lentiviral vector or adenoviral vector) encoding Cdx2 by injection into one or more sites surrounding an infarction.

The following example describes isolation of Cdx2 cells from human placenta tissues and determination of new cell surface markers useful for sorting of these cells for further translational studies. Cells may be sorted based on unique cell surface markers instead of reporter genes. Cdx2 cells may be isolated from human placenta tissues and proteomic approaches employed to identify cell surface markers that may be utilized for FACS sorting. Membrane fractionation of Cdx2 cells sorted using the lentiviruses constructed above may be carried out followed by mass spectrometry to identify new peptides. Antibodies to these peptides are designed and tested for their ability to identify and sort Cdx2 cells.

Figure 10A:
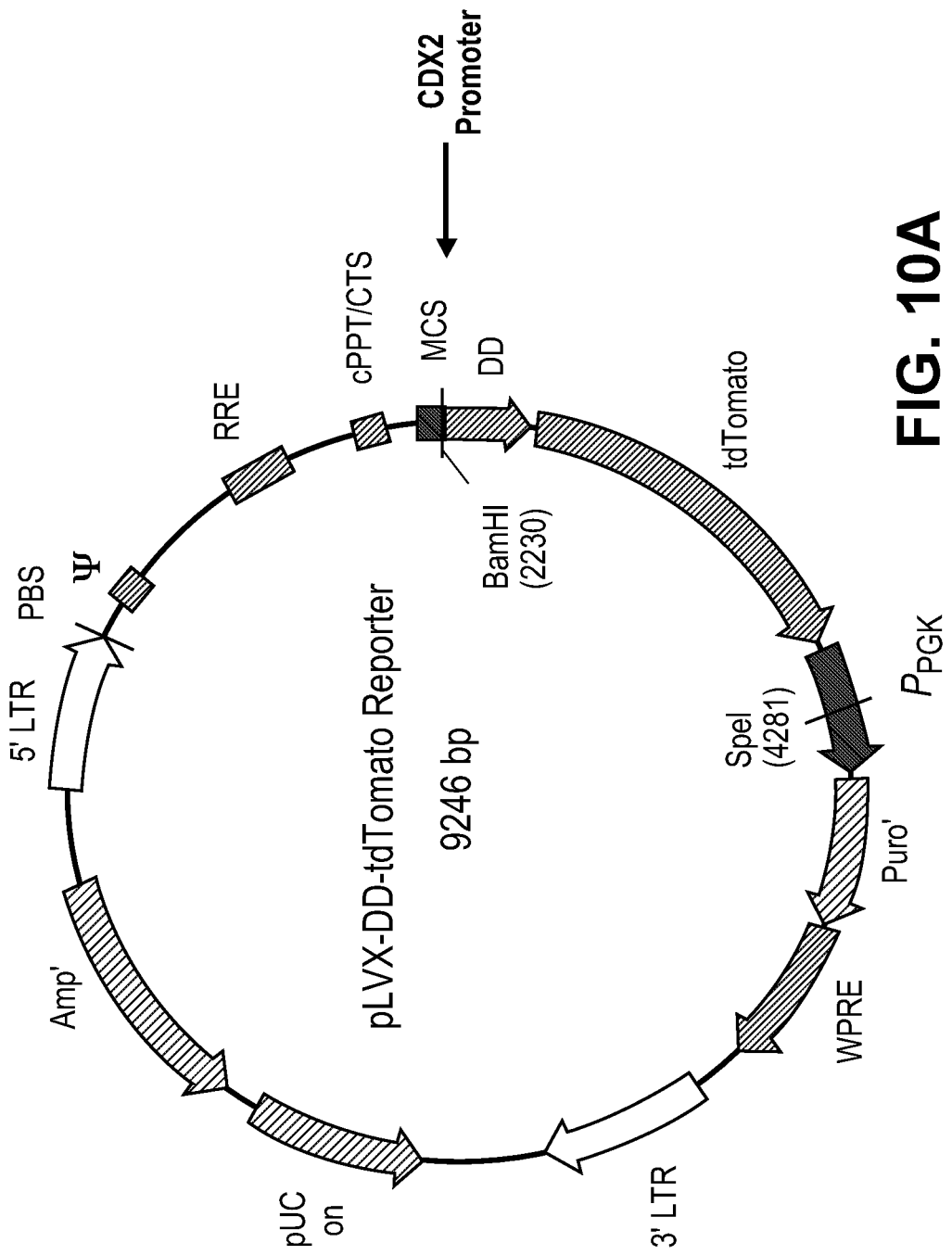
FIG. 10A-D.
Figure 10B:
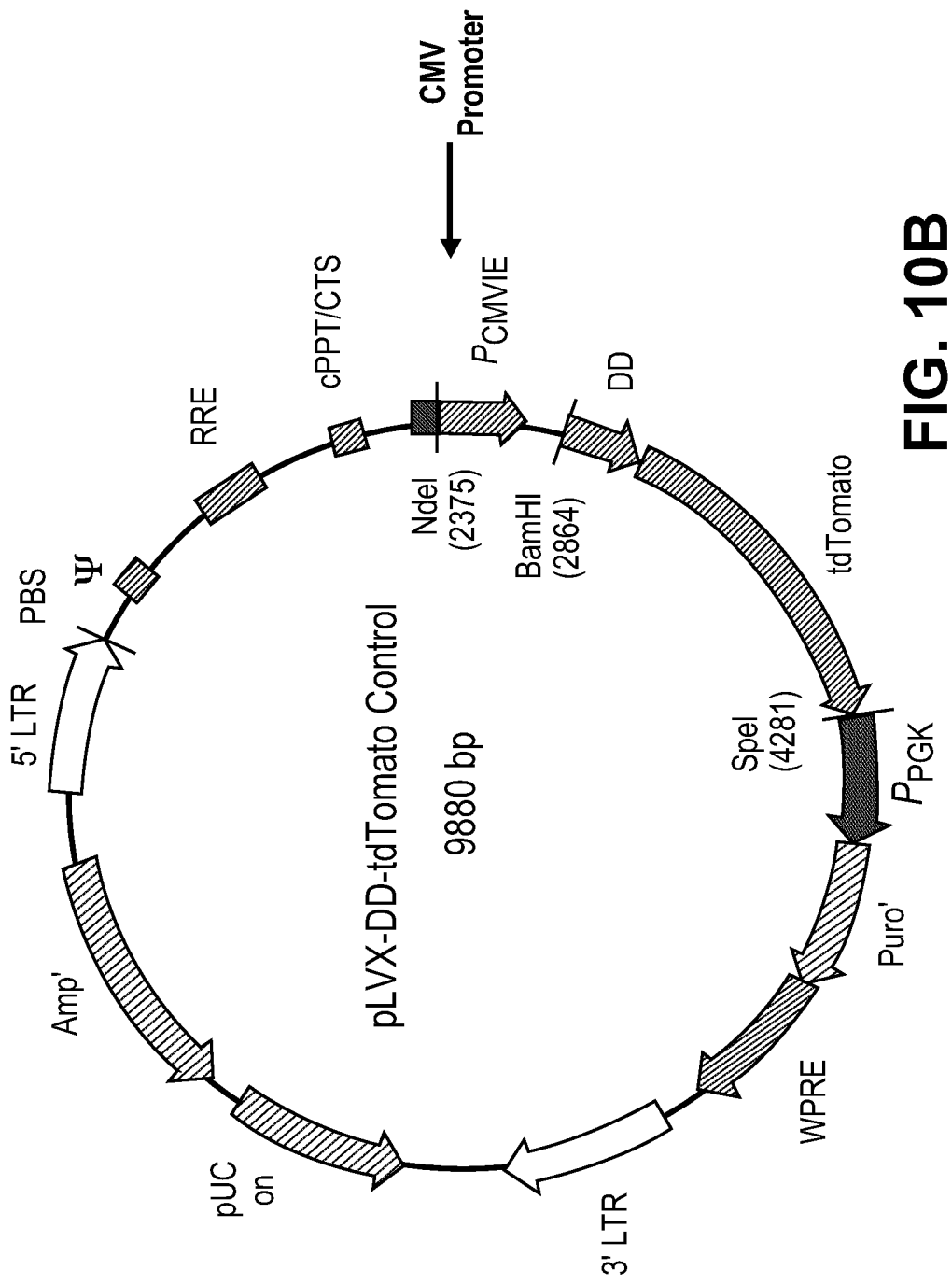

Example 8: Isolation of Cdx2 Cells and a Heterogeneous Mix of Fetal-Derived Placenta Cells from End-Gestation Mouse and Human Placentas, Testing of their Differentiation Properties In Vitro, and Identification of New Cell Surface Markers that Facilitate Further Sorting A lentivirus has been constructed in which the murine Cdx2 promoter drives the expression of tdTomato, and the corresponding control lentivirus utilizes the CMV promoter to drive expression of tdTomato (FIG. 10A, 10B). As there is no definitive characterization of known cell surface markers distinctly associated with the transcription factor Cdx2 in placenta stem cells, FACS sorting is conducted utilizing a lentivirus driving a fluorescent reporter.

Figure 10C:
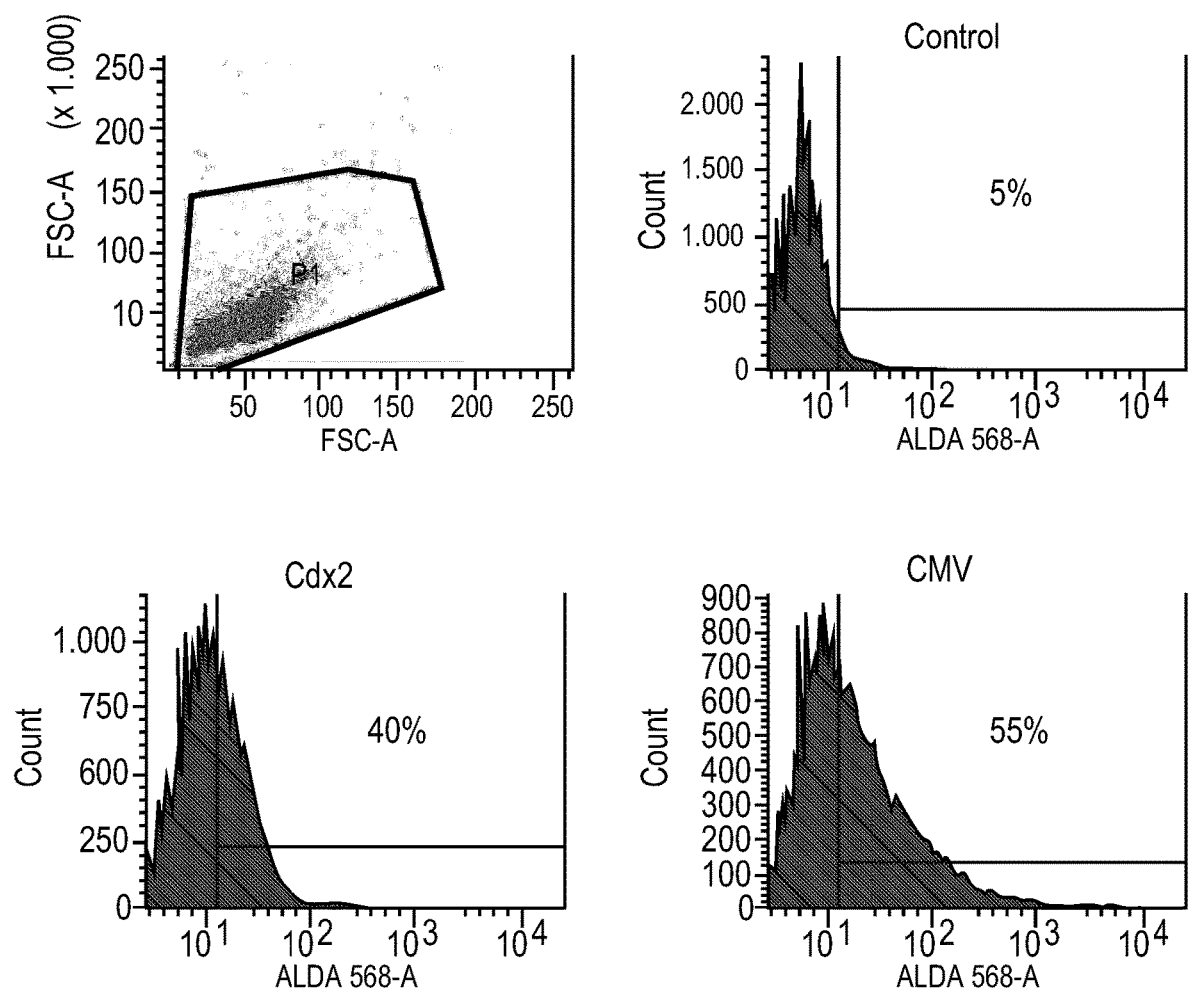
Figure 10D:
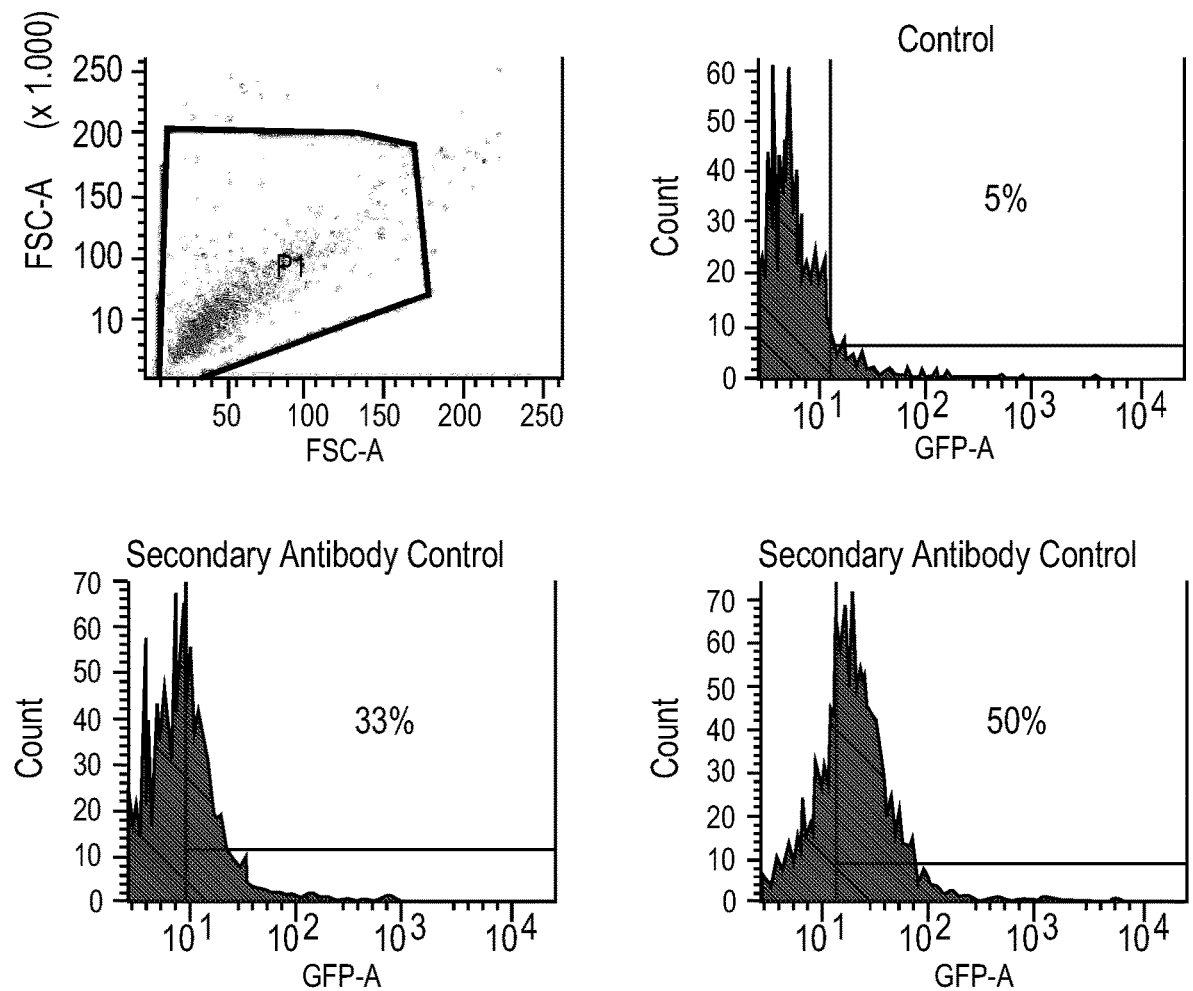

In prior studies, permeabilized GFP cells were isolated from maternal hearts in order to assay the presence of Cdx2 by FACS. The efficacy of our lentivirus in its ability to select Cdx2 cells has been demonstrated in FIG. 10C. When the CT26. A wild type (WT) murine colon carcinoma cell line which expresses Cdx2 was transduced with the lentivirus; 40% of cells expressed TdTomato. This is more efficient than the 17% of cells identified by the Cdx2 monoclonal antibody through FACS sorting depicted in FIG. 10D.

The expression of Cdx2 and Eomesodermin, two markers of TS cells, have been confirmed by RNA microarray in fetal cells isolated from end-gestation placentas (see FIG. 5C).

Cdx2 cells may be specifically selected from end-gestation placentas from both mouse and human species and their differentiation properties in vitro may be compared to a heterogeneous mix of fetal-derived placenta stem cells (hfpcs). Interestingly, the RNA array data indicates that fetal cells in the placenta express high levels of CD9 (FIG. 5C), a cell surface molecule and a member of the transmembrane-4 family that has been associated with Cdx2 expression in intestinal epithelial cells. Membrane fractionation of Cdx2 cells from placenta sorted using the lentiviruses described above is performed, using an antibody to CD9 to confirm its expression on the surface of these cells, and utilizing mass spectrometry to identify other novel peptides, if needed.

End-gestation placenta from both mice and humans isminced and a homogeneous cell suspension prepared according to established protocols. The cell suspension is mixed with lentivirus for a period of at least 24 hrs and then FACS is utilized to collect cells expressing tdTomato. The control lentivirus is utilized in separate tubes of the corresponding cell suspension to set the appropriate gates for FACS. Cdx2-positive cells are then co-cultured on feeder layers of cardiac mesenchymal fibroblasts (CMF) and separately, on feeder layers of neonatal cardiomyocytes. Live-imaging microscopy is utilized to document the differentiation pathways of the Cdx2 cells. Immunofluorescence staining with antibodies to VE-Cadherin, CD31, alpha-smooth muscle actin, alpha-actinin, and cardiac troponin T is performed to assay for differentiation to the endothelial cell, smooth muscle cell, or cardiomyocyte fate once the cells are fixed.

Hfpcs are sorted from cell suspensions of end-gestation mouse placentas utilizing the GFP marker by mating wild-type virgin mice with GFP-expressing male transgenic mice, thus assuring that approximately 50% of fetuses express GFP. These are also co-cultured with the feeder layers described above and their differentiation characteristics are monitored also as described above. These experiments allow for determination of the precise cell type(s) that is(are) capable of differentiating to spontaneously beating cardiomyocytes in vitro as recently demonstrated.

This is important to the field of regenerative biology given the technical difficulties of inducing true cardiomyogenesis in vitro.

Antibodies to CD9 will be used as described above to confirm its expression on Cdx2 cells isolated from murine and human placenta, and to exclude its expression on the cell surfaces of other stem cell types isolated from placenta. High throughput proteomics studies, such as two dimensional gel electrophoresis, liquid chromatography, and mass spectrometry, will also be used in order to identify cell surface markers of Cdx2 cells if CD9 does not appear to be a unique cell surface marker expressed by Cdx2 cells from placenta.

Example 9: Testing the Ability of Cdx2 Cells Versus a Heterogeneous Mix of Fetal-Derived Cells Isolated from Placenta to Form Cardiomyocytes and Blood Vessels In Vivo and Restoring Cardiac Function Via Transplantation Experiments in the Post-Myocardial Infarction Setting a) Experimental Plan-Studies in the Rat MI Model Nude, athymic, female rats are utilized for these experiments with four groups to be tested as follows: 1) Group 1 will undergo MI via ligation of the left anterior descending artery (LAD). This results in a 30% infarction of the left ventricle as previously demonstrated (Woo et al, 2006). After allowing one week of recovery, the chest will be re-opened and the animals will receive Cdx2 cells that have been collected utilizing the Cdx2 lentivirus from end-gestation rat placentas obtained from a different group of female rats. $10^6$ cells will be injected into the peri-infarct border zone at ten distinct, equally spaced sites. Cell delivery will be performed in a blinded manner. The chest will be closed, and the animals will be monitored over a 3-month period. Echocardiography will be utilized to assess cardiac function at baseline, 1 week after MI prior to cell injection, 1 month post cell injection, and at 3 months post-cell injection. The animals will then undergo hemodynamic studies with LV pressure catheters prior to sacrifice at 3 months post cell injection. Hearts will be collected and infarction sizes will be measured using Masson Trichrome staining according to conventional methods (Woo et al, 2006). Tissue sections will be prepared from infarct zone, peri-infarct border zone and remote zones; and cellular differentiation will be analyzed using immunofluorescence. Antibodies to VE-Cadherin, CD31, alpha-smooth muscle actin, alpha-actinin, and cardiac troponin T will be utilized to assay differentiation to endothelial, smooth muscle and cardiac lineages. Co-immunostaining with antibody to tdTomato will be performed to ascertain whether the Cdx2 cells give rise to these diverse cardiac lineages in the in vivo infarct model. All echocardiographic, hemodynamic, and histologic studies will be performed in a blinded manner. 2) Group 2 will undergo MI via LAD ligation. One week later, they will receive $10^6$ hfpcs via direct injection in the peri-infarct border as described above. The hfpcs will be obtained from the end-gestation placentas of a different group of female rats, and mononuclear cells will be isolated utilizing FACS sorting based on the presence of the Y-chromosome to ensure they are of fetal origin. Echocardiographic, hemodynamic, and histologic analyses will be performed as described above. 3) Group 3 will undergo MI via LAD ligation and one week later, will receive $10^6$ rat cardiac fibroblasts. This will ensure that any evidence of cardiac repair we note in Groups 1 and 2 is due to the presence of stem or progenitor cells and not due to nonspecific cell effects of preventing scar expansion. Echocardiography, hemodynamic, and histologic analyses will be performed as describe above. 4) Group 4 will undergo MI via LAD ligation and one week later, will receive PBS control injections in ten (10) distinct peri-infarct sites. Echocardiography, hemodynamic, and histologic analyses will be performed as describe above.

Power Analysis:

Power for balanced, one-way ANOVA for 4 groups (Control, Fibroblast Control Cells, Mixed Placental Cells and Cdx2 Placental Cells) with N=12 in each group at a fixed alpha level of 0.05 using the Omnibus Overall F Test for One-Way ANOVA. The power is 0.875 or 87.5% for the Omnibus Test that at least one group mean is different from the others. The power to detect differences in (specific) pair-wise group means is 0.816 or 81.6%.

b) Experimental Plan-Studies in the Porcine MI Model

Porcine infarction model: Forty (40) Yorkshire swine weighing 20-25 kg will undergo surgical instrumentation for subsequent noninvasive measurement of LV pressure and dimension and myocardial oxygen consumption according to conventional methods (Amado et al., 2005;1 Ekelund et al., 1999; and Saavedra et al., 2002). The animals will be instrumented, via median sternotomy, with indwelling catheters in the descending aorta, right atrial appendage, and great cardiac vein. Endocardial ultrasound crystals (SONOMETRICS, Ontario, Canada) will be inserted to measure short-axis dimension, and a pneumatic occluder will be placed around the inferior vena cava for graded preload reduction to assess LY-pressure-dimension relations. A 4-5 mm flow probe (TRANSONICS, Ithaca, NY) will be placed around the mid-LAD to measure coronary volume flow. A solid-state miniature pressure transducer (P22, Konigsberg Instruments®, Pasadena, CA) will be placed in the L V apex for high-fidelity recordings of L V pressure. Additional pacing leads will be secured in the left atrial appendage for pacing during hemodynamic measurements. During surgery, MI will be induced by a 60-min occlusion of the LAD, followed by reperfusion. There will be 12 animals per group and three groups will be tested. Animals will be randomized to receive intramyocardial injections of either human Cdx2 cells or human hfpcs (depending on the best results group from rat study) [106 cells]. The second group of animals will receive 106 human fibroblasts, and the third will receive PBS control injections. All injections will be performed in a blinded manner. In order to preclude the possibility of immune rejection for the purposes of this study, an immunosuppressive regimen of IV prednisone and IV tacrolimus/cyclosporine will be utilized according to prior experience of the SJTRI team in a different stem cell therapy study. Four additional animals will undergo surgical preparation and instrumentation without coronary occlusion for the assessment of hemodynamic values in the absence of MI. Hemodynamics in the infarcted animals will be re-assessed six weeks post-MI.

Power Analysis:

Power for balanced, one-way ANOVA for 3 groups (Control Vehicle, Control Cells, Cdx2 Cells) with N=12 in each group at a fixed alpha level of 0.05 using the Omnibus Overall F Test for One-Way ANOVA. The power is 0.902 or 90.2% for the Omnibus Test that at least one group mean is different from the others. The power to detect differences in (specific) one group mean is different from the other group mean is 0.856 or 85.6%.

Measures of Hemodynamics and Cardiac Function:

Pressure-dimension data will be recorded at steady state and during transient inferior vena cava occlusion. Myocardial contractility and/or work will be indexed by the maximal rate of isovolumetric contraction (+dP/dt), stroke work (SW), and ventricular elastance, the slope of the end-systolic pressure—dimension relationship (Ees) (Hare et al., 1999). Preload will be analyzed as end-diastolic dimension and pressure, and afterload will be evaluated as effective arterial elastance (Kelly et al., 1992), the ratio of LV end-systolic pressure to stroke dimension. Hemodynamic pressure-dimension data will be digitized at 200 Hz and stored for subsequent analysis on a personal computer by using custom software. Myocardial oxygen consumption per cardiac cycle (MVO2) will be calculated from the arteriovenous difference of oxygen saturation in simultaneously sampled coronary sinus and aortic blood, multiplied by LAD flow and divided by heart rate. Cardiac mechanical efficiency will be calculated as the SW/MVO2 ratio (Ekelund et al., 1999). Transthoracic echocardiography (SONOS 5500) and MRI (GE 1.5 T Cardiac Magnetic Resonance stand with a short 1.2 meter bore and body coils optimized for F-19) will be utilized to assess ventricular function prior to MI and six weeks post-MI.

Immunofluorescence Studies for Detection of Progenitor Cells and Cellular Differentiation:

Three (3) animals from each group will be sacrificed two weeks post-MI and the remainder will be sacrificed six-weeks post-MI. Their hearts will be analyzed at both microscopic and gross levels. Myocardial tissue will be prepared for immunohistochemistry according to conventional methods (Kawamoto et al, 2004; and Shake et al., 2002). Tissue samples will be obtained from three specific areas: infarct zone, peri-infarct border zone, and remote tissue. Antibodies to VE-Cadherin, CD31, alpha-smooth muscle actin, alpha-actinin, and cardiac troponin T will be utilized to assay differentiation to endothelial, smooth muscle and cardiac lineages. Antibody to tdTomato will be utilized to identify the Cdx2 cells to determine if these cells engraft and differentiate to diverse cardiac lineages after transplantation. Phosphohistone H3 staining will be performed to assess the presence of active dividing cells.

Infarct size assessment and myofilament density measurement: Myocardial fibrosis will be determined as a percentage of the left ventricle from whole-heart slices. For this purpose, hearts will be excised and sectioned into 8-mm-thick short-axis slices. Each slice will be weighed and digitally photographed. Analysis will be performed using Masson trichrome staining using conventional methods (Cheng et al., 2007). Infarcted areas and LV borders will be manually traced for each slice by using a custom research software package IMAGE ANALYSIS 4.0.2 beta version (Scion®, Frederick, MD). Infarct size will be determined, in a blinded fashion, as percentage of L V mass from the digital pictures and normalized by the weight of the slice. Myofilament density will be measured at the border zones by counting the numbers of cardiomyocytes (delineated by immunostaining for a-actinin) per high-power field and averaging over at least three mid-ventricular transverse sections per heart (Woo et al., 2006).

Statistical Analyses:

All values will be expressed as mean±SE. Student's paired t test will be used to compare data before and after treatment. A value of p<0.5 will be considered as statistically significant.

While preferred embodiments have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Abbreviations and Acronyms eGFP enhanced green fluorescent protein; TS trophoblast stem; Cdx2 Caudal-related homeobox2; ES embryonic stem; RT room temperature; WT wild type; MI myocardial infarction; FACS fluorescence activated cell sorting; CMFs cardiac mesenchymal feeders; VE-cad VE-Cadherin; ROIs regions of interest; α-sarc alpha-sarcomeric actin; cTnT cardiac troponin T; Cx43 connexin 43; and α-SMA alpha-smooth muscle actin.

REFERENCES CITED

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

Albelda, S. M., Muller, W. A., Buck, C. A., and Newman, P. J. (1991). Molecular and cellular properties of PECAM-1 (endoCAM/CD31): a novel vascular cell-cell adhesion molecule. *J Cell Biol* 114, 1059-1068.

Bayes-Genis, A., Bellosillo, B., de la Calle, O., Salido, M., Roura, S., Ristol, F. S., Soler, C., Martinez, M., Espinet, B., Serrano, S., et al. (2005). Identification of male cardiomyocytes of extracardiac origin in the hearts of women with male progeny: male fetal cell microchimerism of the heart. *J Heart Lung Transplant* 24, 2179-2183.

Beck, F., and Stringer, E. J. (2010). The role of Cdx genes in the gut and in axial development. *Biochem Soc Trans* 38, 353-357.

Beltrami, A. P., Barlucchi, L., Torella, D., Baker, M., Limana, F., Chimenti, S., Kasahara, H., Rota, M., Musso, E., Urbanek, K., et al. (2003). Adult cardiac stem cells are multipotent and support myocardial regeneration. *Cell* 114, 763-776.

Bianchi, D. W., Zickwolf, G. K., Weil, G. J., Sylvester, S., and DeMaria, M. A. (1996). Male fetal progenitor cells persist in maternal blood for as long as 27 years postpartum. *Proc Natl Acad Sci USA* 93, 705-708.

Bolli, P., and Chaudhry, H. W. (2010). Molecular physiology of cardiac regeneration. *Ann N Y Acad Sci* 1211, 113-126.

Campagnoli, C., Roberts, I. A., Kumar, S., Bennett, P. R., Bellantuono, I., and Fisk, N. M. (2001). Identification of mesenchymal stem/progenitor cells in human first-trimester fetal blood, liver, and bone marrow. *Blood* 98, 2396-2402.

Chawengsaksophak, K., de Graaff, W., Rossant, J., Deschamps, J., and Beck, F. (2004). Cdx2 is essential for axial elongation in mouse development. *Proc Natl Acad Sci USA* 101, 7641-7645. Chawengsaksophak, K., James, R., Hammond, V. E., Kontgen, F., and Beck, F. (1997). Homeosis and intestinal tumours in Cdx2 mutant mice. *Nature* 386, 84-87.

Chen, J., Sanberg, P. R., Li, Y., Wang, L., Lu, M., Willing, A. E., Sanchez-Ramos, J., and Chopp, M. (2001). Intravenous administration of human umbilical cord blood reduces behavioral deficits after stroke in rats. *Stroke* 32, 2682-2688.

Cheng, R. K., Asai, T., Tang, H., Dashoush, N. H., Kara, R. J., Costa, K. D., Naka, Y., Wu, E. X., Wolgemuth, D. J., and Chaudhry, H. W. (2007). Cyclin A2 induces cardiac regeneration after myocardial infarction and prevents heart failure. *Circ Res* 100, 1741-1748.

Civin, C. I., Almeida-Porada, G., Lee, M. J., Olweus, J., Terstappen, L. W., and Zanjani, E. D. (1996). Sustained, retransplantable, multilineage engraftment of highly purified adult human bone marrow stem cells in vivo. *Blood* 88, 4102-4109.

Felker, G. M., Thompson, R. E., Hare, J. M., Hruban, R. H., Clemetson, D. E., Howard, D. L., Baughman, K. L., and Kasper, E. K. (2000). Underlying causes and long-term survival in patients with initially unexplained cardiomyopathy. *N Engl J Med* 342, 1077-1084.

Fujiki, Y., Johnson, K. L., Peter, I., Tighiouart, H., and Bianchi, D. W. (2009). Fetal cells in the pregnant mouse are diverse and express a variety of progenitor and differentiated cell markers. *Biol Reprod* 81, 26-32.

Gekas, C., Dieterlen-Lievre, F., Orkin, S. H., and Mikkola, H. K. (2005). The placenta is a niche for hematopoietic stem cells. *Dev Cell* 8, 365-375.

He, J. Q., Ma, Y., Lee, Y., Thomson, J. A., and Kamp, T. J. (2003). Human embryonic stem cells develop into multiple types of cardiac myocytes: action potential characterization. Circ Res 93, 32-39.

James, P. R. (2004). A review of peripartum cardiomyopathy. *Int J Clin Pract* 58, 363-365.

Khosrotehrani, K., Johnson, K. L., Cha, D. H., Salomon, R. N., and Bianchi, D. W. (2004). Transfer of fetal cells with multilineage potential to maternal tissue. *JAMA* 292, 75-80.

Khosrotehrani, K., Leduc, M., Bachy, V., Nguyen Huu, S., Oster, M., Abbas, A., Uzan, S., and Aractingi, S. (2008). Pregnancy allows the transfer and differentiation of fetal lymphoid progenitors into functional T and B cells in mothers. *J Immunol* 180, 889-897.

Kleeberger, W., Versmold, A., Rothamel, T., Glockner, S., Bredt, M., Haverich, A., Lehmann, U., and Kreipe, H. (2003). Increased chimerism of bronchial and alveolar epithelium in human lung allografts undergoing chronic injury. *Am J Pathol* 162, 1487-1494.

Klonisch, T., and Drouin, R. (2009). Fetal-maternal exchange of multipotent stem/progenitor cells: microchimerism in diagnosis and disease. *Trends Mol Med* 15, 510-518.

Komuro, I., and Izumo, S. (1993). Csx: a murine homeobox-containing gene specifically expressed in the developing heart. *Proc Natl Acad Sci USA* 90, 8145-8149.

Laugwitz, K. L., Moretti, A., Lam, J., Gruber, P., Chen, Y., Woodard, S., Lin, L. Z., Cai, C. L., Lu, M. M., Reth, M., et al. (2005a). Postnatal isl1+ cardioblasts enter fully differentiated cardiomyocyte lineages. *Nature* 433, 647-653.

Laugwitz, K. L., Moretti, A., Lam, J., Gruber, P., Chen, Y., Woodard, S., Lin, L. Z., Cai, C. L., Lu, M. M., Reth, M., et al. (2005b). Postnatal isl1+ cardioblasts enter fully differentiated cardiomyocytes lineages. *Nature* 433, 647-653.

Liegeois, A., Escourrou, J., Ouvre, E., and Charreire, J. (1977). Microchimerism: a stable state of low-ratio proliferation of allogeneic bone marrow. *Transplant Proc* 9, 273-276.

Lints, T. J., Parsons, L. M., Hartley, L., Lyons, I., and Harvey, R. P. (1993). Nkx-2.5: a novel murine homeobox gene expressed in early heart progenitor cells and their myogenic descendants. *Development* 119, 969.

Martin, C. M., Meeson, A. P., Robertson, S. M., Hawke, T. J., Richardson, J. A., Bates, S., Goetsch, S. C., Gallardo, T. D., and Garry, D. J. (2004). Persistent expression of the ATP-binding cassette transporter, Abcg2, identifies cardiac SP cells in the developing and adult heart. *Dev Biol* 265, 262-275.

Mehta, N.J., Mehta, R. N., and Khan, I. A. (2001). Peripartum cardiomyopathy: clinical and therapeutic aspects. *Angiology* 52, 759-762.

Mikhail, M. A., M'Hamdi, H., Welsh, J., Levicar, N., Marley, S. B., Nicholls, J. P., Habib, N. A., Louis, L. S., Fisk, N. M., and Gordon, M. Y. (2008). High frequency of fetal cells within a primitive stem cell population in maternal blood. *Hum Reprod* 23, 928-933.

Newman, P. J., Berndt, M. C., Gorski, J., White, G. C., 2nd, Lyman, S., Paddock, C., and Muller, W. A. (1990). PECAM-1 (CD31) cloning and relation to adhesion molecules of the immunoglobulin gene superfamily. *Science* 247, 1219-1222.

Nguyen Huu, S., Dubernard, G., Aractingi, S., and Khosrotehrani, K. (2006). Feto-maternal cell trafficking: a transfer of pregnancy associated progenitor cells. *Stem Cell Rev* 2, 111-116.

Nguyen Huu, S., Oster, M., Uzan, S., Chareyre, F., Aractingi, S., and Khosrotehrani, K. (2007). Maternal neoangiogenesis during pregnancy partly derives from fetal endothelial progenitor cells. *Proc Natl Acad Sci USA* 104, 1871-1876.

Niwa, H., Toyooka, Y., Shimosato, D., Strumpf, D., Takahashi, K., Yagi, R., and Rossant, J. (2005). Interaction between Oct3/4 and Cdx2 determines trophectoderm differentiation. *Cell* 123, 917-929.

Nussbaum, J., Minami, E., Laflamme, M. A., Virag, J. A., Ware, C. B., Masino, A., Muskheli, V., Pabon, L., Reinecke, H., and Murry, C. E. (2007). Transplantation of undifferentiated murine embryonic stem cells in the heart: teratoma formation and immune response. *FASEB J* 21, 1345-1357.

O'Donoghue, K., Choolani, M., Chan, J., de la Fuente, J., Kumar, S., Campagnoli, C., Bennett, P. R., Roberts, I. A., and Fisk, N. M. (2003). Identification of fetal mesenchymal stem cells in maternal blood: implications for noninvasive prenatal diagnosis. *Mol Hum Reprod* 9, 497-502.

Oh, H., Bradfute, S. B., Gallardo, T. D., Nakamura, T., Gaussin, V., Mishina, Y., Pocius, J., Michael, L. H., Behringer, R. R., Garry, D. J., et al. (2003). Cardiac progenitor cells from adult myocardium: homing, differentiation, and fusion after infarction. *Proc Natl Acad Sci USA* 100, 12313-12318.

Oh, H., Chi, X., Bradfute, S. B., Mishina, Y., Pocius, J., Michael, L. H., Behringer, R. R., Schwartz, R. J., Entman, M. L., and Schneider, M. D. (2004). Cardiac muscle plasticity in adult and embryo by heart-derived progenitor cells. *Ann N Y Acad Sci* 1015, 182-189.

Orlic, D., Kajstura, J., Chimenti, S., Jakoniuk, I., Anderson, S. M., Li, B., Pickel, J., McKay, R., NadalGinard, B., Bodine, D. M., et al. (2001). Bone marrow cells regenerate infarcted myocardium. *Nature* 410, 701-705.

Osada, H., Doi, S., Fukushima, T., Nakauchi, H., Seki, K., and Sekiya, S. (2001). Detection of fetal HPCs in maternal circulation after delivery. *Transfusion* 41, 499-503.

Pfaffl, M. W. (2001). A new mathematical model for relative quantification in real-time RT-PCR. *Nucleic Acids Res* 29, e45.

Ralston, A., Cox, B. J., Nishioka, N., Sasaki, H., Chea, E., Rugg-Gunn, P., Guo, G., Robson, P., Draper, J. S., and Rossant, J. (2010). Gata3 regulates trophoblast development downstream of Tead4 and in parallel to Cdx2. *Development* 137, 395-403.

Ralston, A., and Rossant, J. (2005). Genetic regulation of stem cell origins in the mouse embryo. *Clin Genet* 68, 106-112.

Ro, A., and Frishman, W. H. (2006). Peripartum cardiomyopathy. *Cardiol Rev* 14, 35-42.

Sperger, J. M., Chen, X., Draper, J. S., Antosiewicz, J. E., Chon, C. H., Jones, S. B., Brooks, J. D., Andrews, P. W., Brown, P. O., and Thomson, J. A. (2003). Gene expression patterns in human embryonic stem cells and human pluripotent germ cell tumors. *Proc Natl Acad Sci USA* 100, 13350-13355.

Strumpf, D., Mao, C. A., Yamanaka, Y., Ralston, A., Chawengsaksophak, K., Beck, F., and Rossant, J. (2005). Cdx2 is required for correct cell fate specification and differentiation of trophectoderm in the mouse blastocyst. *Development* 132, 2093-2102.

Tan, X. W., Liao, H., Sun, L., Okabe, M., Xiao, Z. C., and Dawe, G. S. (2005). Fetal microchimerism in the maternal mouse brain: a novel population of fetal progenitor or stem cells able to cross the blood-brain barrier? *Stem Cells* 23, 1443-1452.

Tanaka, S., Kunath, T., Hadjantonakis, A. K., Nagy, A., and Rossant, J. (1998). Promotion of trophoblast stem cell proliferation by FGF4. *Science* 282, 2072-2075.

Terstappen, L. W., Huang, S., Safford, M., Lansdorp, P. M., and Loken, M. R. (1991). Sequential generations of hematopoietic colonies derived from single nonlineage-committed CD34+CD38-progenitor cells. *Blood* 77, 1218-1227.

Ueyama, T., Kasahara, H., Ishiwata, T., Nie, Q., and Izumo, S. (2003). Myocardin expression is regulated by Nkx2.5, and its function is required for cardiomyogenesis. *Mol Cell Biol,* 23, 9222-9232.

van Laake, L. W., Passier, R., Monshouwer-Kloots, J., Verkleij, A. J., Lips, D. J., Freund, C., den Ouden, K., Ward-van Oostwaard, D., Korving, J., Tertoolen, L. G., et al. (2007). Human embryonic stem cell-derived cardiomyocytes survive and mature in the mouse heart and transiently improve function after myocardial infarction. *Stem Cell Res* 1, 9-24.

Wang, Y., Iwatani, H., Ito, T., Horimoto, N., Yamato, M., Matsui, I., Imai, E., and Hori, M. (2004). Fetal cells in mother rats contribute to the remodeling of liver and kidney after injury. *Biochem Biophys Res Commun* 325, 961-967.

Wu, S. M., Chien, K. R., and Mummery, C. (2008). Origins and fates of cardiovascular progenitor cells. *Cell* 132, 537-543.

Xu, C., Police, S., Rao, N., and Carpenter, M. K. (2002). Characterization and enrichment of cardiomyocytes derived from human embryonic stem cells. *Circ Res* 91, 501-508.

Yang, L., Soonpaa, M. H., Adler, E. D., Roepke, T. K., Kattman, S. J., Kennedy, M., Henckaerts, E., Bonham, K., Abbott, G. W., Linden, R. M., et al. (2008). Human cardiovascular progenitor cells develop from a KDR+ embryonic-stem-cell-derived population. *Nature* 453, 524-528.

Cheng R K, Asai T, Tang H, et al. Cyclin A2 induces cardiac regeneration after myocardial infarction and prevents heart failure. *Circ Res*. Jun. 22 2007; 100(12):1741-1748.

Pfaffl M W. A new mathematical model for relative quantification in real-time RT-PCR. *Nucleic Acids Res*. May 1 2001; 29(9):e45.

Fujiki Y, Johnson K L, Tighiouart H, Peter I, Bianchi D W. Fetomaternal trafficking in the mouse increases as delivery approaches and is highest in the maternal lung. *Biol Reprod*. November 2008; 79(5):841-848.

Su E C, Johnson K L, Tighiouart H, Bianchi D W. Murine maternal cell microchimerism: analysis using real-time PCR and in vivo imaging. *Biology of reproduction*. 2008; 78(5): 883-887.

Joshi M, Keith Pittman H, Haisch C, Verbanac K. Real-time PCR to determine transgene copy number and to quantitate the biolocalization of adoptively transferred cells from EGFP-transgenic mice. *BioTechniques*. 2008; 45(3): 247-258.

Amado L C, Saliaris A P, Schuleri K H, St John M, Xie J S, Cattaneo S, Durand D J, Fitton T, Kuang J Q, Stewart G, Lehrke S, Baumgartner W W, Martin B J, Heldman A W, Hare J M. Cardiac repair with intramyocardial injection of allogeneic mesenchymal stem cells after myocardial infarction. *Proc Natl Acad Sci USA*. 2005; 102: 11474-11479.

Boyd M, Hansen M, Jensen T G, Perearnau A, Olsen A K, Bram L L, Bak M, Tommerup N, Olsen J, Troelsen J T. Genome-wide analysis of cdx2 binding in intestinal epithelial cells (caco-2). *J Biol Chem*. 2010; 285: 25115-25125.

Carlson B M. *Human embryology and developmental biology*. Philadelphia, PA: Mosby/Elsevier; 2009.

Ekelund U E, Harrison R W, Shokek O, Thakkar R N, Tunin R S, Senzaki H, Kass D A, Marban E, Hare J M. Intravenous allopurinol decreases myocardial oxygen consumption and increases mechanical efficiency in dogs with pacing-induced heart failure. *Circ Res*. 1999; 85: 437-445.

Fujiki Y, Johnson K L, Tighiouart H, Peter I, Bianchi D W. Fetomaternal trafficking in the mouse increases as delivery approaches and is highest in the maternal lung. *Biol Reprod*. 2008; 79: 841-848.

Hare J M, Kass D A, Stamler J S. The physiological response to cardiovascular 'orphan' g protein-coupled receptor agonists. *Nat Med*. 1999; 5: 1241-1242.

Kara R J, Bolli P, Karakikes I, Matsunaga I, Tripodi J, Tanweer O, Altman P, Shachter N S, Nakano A, Najfeld V, Chaudhry H W. Fetal cells traffic to injured maternal myocardium and undergo cardiac differentiation. *Circ Res*. 2012; 110: 82-93.

Kawamoto A, Murayama T, Kusano K, Ii M, Tkebuchava T, Shintani S, Iwakura A, Johnson I, von Samson P, Hanley A, Gavin M, Curry C, Silver M, Ma H, Kearney M, Losordo D W. Synergistic effect of bone marrow mobilization and vascular endothelial growth factor-2 gene therapy in myocardial ischemia. *Circulation*. 2004; 110: 1398-1405.

Kelly R P, Ting C T, Yang $T_M$, Liu C P, Maughan W L, Chang M S, Kass D A. Effective arterial elastance as index of arterial vascular load in humans. *Circulation*. 1992; 86: 513-521.

Saavedra W F, Paolocci N, St John M E, Skaf M W, Stewart G C, Xie J S, Harrison R W, Zeichner J, Mudrick D, Marban E, Kass D A, Hare J M. Imbalance between xanthine oxidase and nitric oxide synthase signaling pathways underlies mechanoenergetic uncoupling in the failing heart. *Circ Res*. 2002; 90: 297-304.

Shake J G, Gruber P J, Baumgartner W A, Senechal G, Meyers J, Redmond J M, Pittenger M F, Martin B J. Mesenchymal stem cell implantation in a swine myocardial infarct model: Engraftment and functional effects. *Ann Thorac Surg*. 2002; 73: 1919-1925; discussion 1926.

Woo Y J, Panlilio C M, Cheng R K, Liao G P, Atluri P, Hsu V M, Cohen J E, Chaudhry H W. Therapeutic delivery of cyclin a2 induces myocardial regeneration and enhances cardiac function in ischemic heart failure. *Circulation*. 2006; 114: 1206-213.

---

What is claimed is:

1. A method for restoring cardiac function comprising introducing an effective amount of a composition comprising a population of placenta-derived cells into a heart of a subject in need thereof, wherein at least about 75% of the cells in the population of placenta-derived cells express caudal type homeobox 2 (Cdx2).

2. The method of claim 1, wherein said cells are progenitor cells or stem cells.

3. The method of claim 1, wherein said cells express one or more of cluster of differentiation (Cd9), Eomesodermin (Eomes), CD34, CD31, and c-kit.

4. The method of claim 1, wherein the composition increases cardiomyocyte formation, increases cardiomyocyte proliferation, increases cardiomyocyte cell cycle activation, increases mitotic index of cardiomyocytes, increases myofilament density, increases borderzone wall thickness, or a combination thereof.

5. The method of claim 1, wherein the cells that express Cdx2 are fetal stem cells.

6. The method of claim 1, wherein the cells that express Cdx2 are isolated cells.

7. The method of claim 1, wherein the subject is diagnosed with, or at risk for, myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy.

8. The method of claim 1, wherein introducing or contacting the composition comprises implanting the composition into cardiac tissue of the subject.

9. The method of claim 1, wherein introducing or contacting the composition comprises injecting the composition into the subject.

10. The method of claim 8, wherein the cardiac tissue is selected from the group consisting of myocardium, endocardium, epicardium, connective tissue in the heart, and nervous tissue in the heart.

11. The method of claim 1, wherein the amount of composition comprises from about $1\times10^8$ to about $1\times10^2$ cells.

12. The method of claim 1, wherein the amount of introduced composition comprises from about $1\times10^6$ to about $1\times10^5$ cells.

* * * * *